US012747297B2

(12) United States Patent
Kim et al.

(10) Patent No.: US 12,747,297 B2
(45) Date of Patent: Sep. 29, 2026

(54) BISPECIFIC ANTIBODY SIMULTANEOUSLY BINDING TO INTERLEUKIN-4 RECEPTOR ALPHA SUBUNIT AND INTERLEUKIN-5 RECEPTOR ALPHA SUBUNIT, ENCODING NUCLEIC ACIDS THEREOF AND METHODS OF USE THEREOF FOR TREATMENT

(71) Applicant: AJOU UNIVERSITY INDUSTRY-ACADEMIC COOPERATION FOUNDATION, Suwon-si (KR)

(72) Inventors: Yong Sung Kim, Suwon-si (KR); Hae-Sim Park, Seoul (KR); Jung Eun Kim, Suwon-si (KR); Keunok Jung, Seoul (KR); Dong-Hyun Lee, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 731 days.

(21) Appl. No.: 18/024,143

(22) PCT Filed: Sep. 10, 2021

(86) PCT No.: PCT/KR2021/012344

§ 371 (c)(1),
(2) Date: Mar. 1, 2023

(87) PCT Pub. No.: WO2022/055299

PCT Pub. Date: Mar. 17, 2022

(65) Prior Publication Data

US 2023/0357415 A1 Nov. 9, 2023

(30) Foreign Application Priority Data

Sep. 14, 2020 (KR) ........................ 10-2020-0117667

(51) Int. Cl.

| | |
|---|---|
| ***C07K 16/28*** | (2006.01) |
| ***A61K 39/00*** | (2006.01) |

(52) U.S. Cl.

CPC .......... *C07K 16/2866* (2013.01); *A61K 39/00* (2013.01); *C07K 2317/24* (2013.01); *C07K 2317/30* (2013.01); *C07K 2317/31* (2013.01); *C07K 2317/35* (2013.01); *C07K 2317/522* (2013.01); *C07K 2317/526* (2013.01); *C07K 2317/622* (2013.01); *C07K 2317/732* (2013.01); *C07K 2317/92* (2013.01)

(58) Field of Classification Search

CPC ............ C07K 16/2866; C07K 2317/24; C07K 2317/30; C07K 2317/31; C07K 2317/35; C07K 2317/522; C07K 2317/526; C07K 2317/622; C07K 2317/732; C07K 2317/92; C07K 2317/73; C07K 2317/76; C07K 2317/565; A61K 39/00; A61K 2039/505; A61P 37/08; A61P 29/00

See application file for complete search history.

(56) References Cited

U.S. PATENT DOCUMENTS 5,453,491 A * 9/1995 Takatsu .............. C07K 14/7155
530/395
7,605,237 B2 * 10/2009 Stevens ................... A61P 29/00
530/387.9

FOREIGN PATENT DOCUMENTS

KR 10-2007-0057709 A 6/2007
KR 10-2007-0114765 A 12/2007

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*
Scheffer L, et al. (Nov. 2024) Briefings in Bioinformatics. 25(6):1-10. (https://doi.org/10.1093/bib/bbae537).*
Valdes-Trescano MS, et al. (2023) Molecules. 28(10):3991. pp. 1-7. (https://doi.org/10.3390/molecules28103991).*
Ye C, et al. JMIR Bioinform Biotechnol. Oct. 28, 2022;3(1):e29404. pp. 1-7. (doi: 10.2196/29404).*

(Continued)

*Primary Examiner* — Robert S Landsman
(74) *Attorney, Agent, or Firm* — Sughrue Mion, PLLC

(57) ABSTRACT

An IL-4Rα×IL-5Rα bispecific antibody that simultaneously binds to interleukin (IL)-4 receptor a (IL-4Rα, CD124) and IL-5 receptor a (IL-5Rα, CD125) is provided. A multispecific antibody including the bispecific antibody, a nucleic acid encoding the bispecific antibody or multispecific antibody, a vector including the nucleic acid, and cells transformed by the vector are disclosed. Additionally, a method for producing the bispecific antibody and therapeutic uses of the multispecific antibody in preventing or treating allergic diseases, inflammatory diseases, and eosinophilic diseases associated with IL-4, IL-13 and/or IL-5 are disclosed.

11 Claims, 38 Drawing Sheets

Specification includes a Sequence Listing.

(56) References Cited

OTHER PUBLICATIONS

Godar M, et al. (Oct. 1, 2018) J Allergy Clin Immunol. 142(4):1185-1193. (doi:10.1016/j.jaci.2018.06.002).*
Lee CV, et al. (May/Jun. 2014) mAbs. 6(3):622-627. (http://dx.doi.org/10.4161/mabs.28483).*
Patino E, et al. (Dec. 7, 2011) Structure 19:1864-1875. (DOI 10.1016/j.str.2011.08.015).*
Orcutt KD, et al. (2010) Protein Engineering, Design & Selection. 23(4):221-228. (Published online Dec. 17, 2009 doi:10.1093/protein/gzp077).*
Egan TJ, et al. (2017) MABS. 9(1):68-84. (doi: 10.1080/19420862.2016.1248012).*
Hern-Tze Tina Tan, et al., "Novel Biologicals for the Treatment of Allergic Diseases and Asthma", Current Allergy Asthma Reports, Sep. 9, 2016, vol. 16, No. 70, pp. 1-14 (14 pages).
European Search Report dated Sep. 10, 2024 in Application No. 21867164.2.
GenBank: BAD97311.1, "interleukin 4 receptor alpha chain isoform a precursor variant, partial [*Homo sapiens*]", Jul. 26, 2016, [[http://www.ncbi.nlm.nih.gov/protein/bad97311.1]](2 pages total).
GenBank: CAA43484.1, "interleukin-5 receptor type 2 precursor [*Homo sapiens*]", May 26, 1992, [[https://www.ncbi.nlm.nih.gov/protein/CAA43484.1]] (2 pages total).
Marie Godar, MSc, et al., "A bispecific antibody strategy to target multiple type 2 cytokines in asthma", J Allergy Clin Immunol, 2018, pp. 1-9, and 9e1-9e4 (13 pages total).
Communication issued Jul. 10, 2024, in Korean Application No. 10-2020-0117667.

* cited by examiner

【FIG. 1】
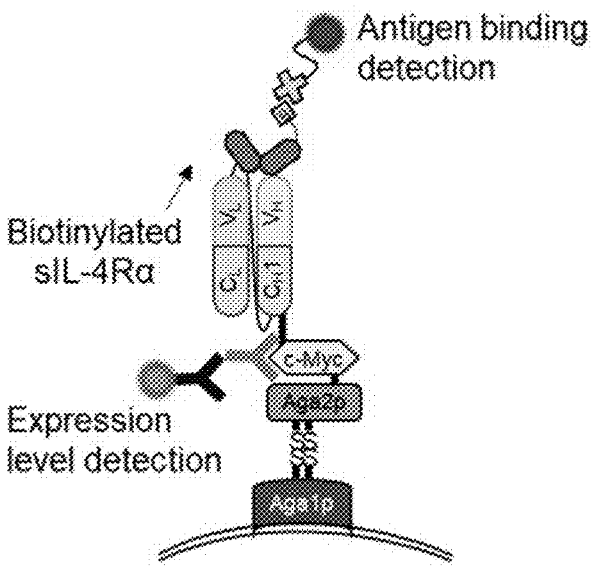
4R34.1.19 scFab Library
| | VH-CDR2 | | | | | | | | | | | | | | | | |
|---|---|---|---|---|---|---|---|---|---|---|---|---|---|---|---|---|---|
| Kabat No. | 50 | 51 | 52 | 52a | 53 | 54 | 55 | 56 | 57 | 58 | 59 | 60 | 61 | 62 | 63 | 64 | 65 |
| 4R34.1.19 | A | I | T | S | S | G | R | S | I | Y | Y | A | D | S | V | K | G |
| Designed codon | | | | X | X | X | R | X | X | X | | X | X | X | X | | |
| | VL-CDR3 | | | | | | | | | | |
|---|---|---|---|---|---|---|---|---|---|---|---|
| Kabat No. | 89 | 90 | 91 | 92 | 93 | 94 | 95 | 95a | 95b | 96 | 97 |
| 4R34.1.19 | G | T | W | D | Y | S | L | S | G | Y | V |
| Designed codon | | | X | X | X | X | X | X | X | X | |
X : maintaining the original amino acids of 4R34.1.19 at a level of ~50% at each residue, using spiked oligonucleotide 【FIG. 2A】
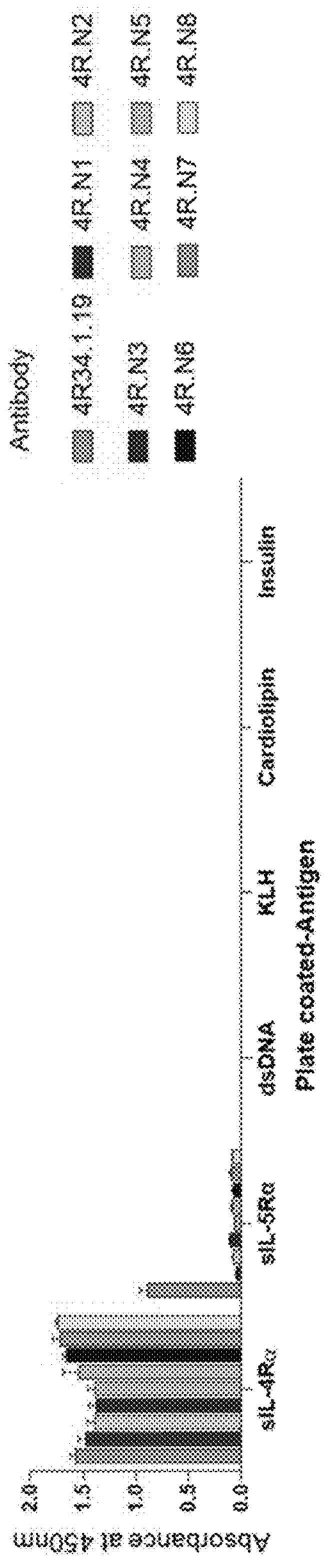
【FIG. 2B】
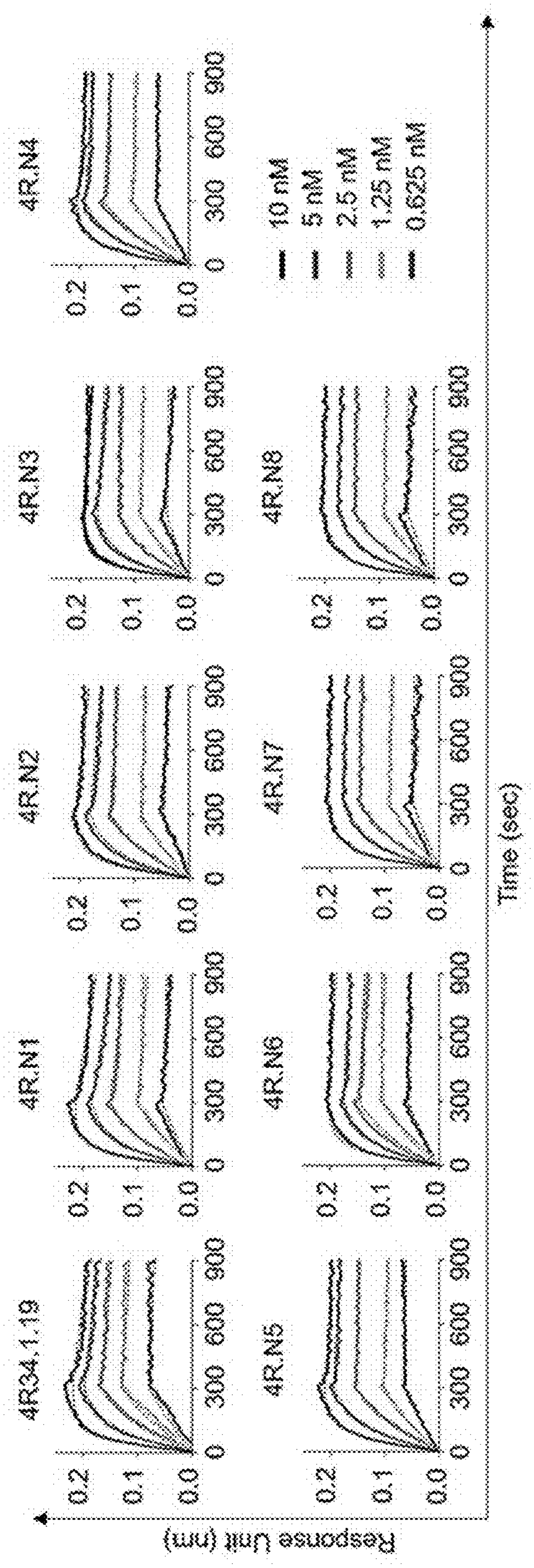

【FIG. 3】
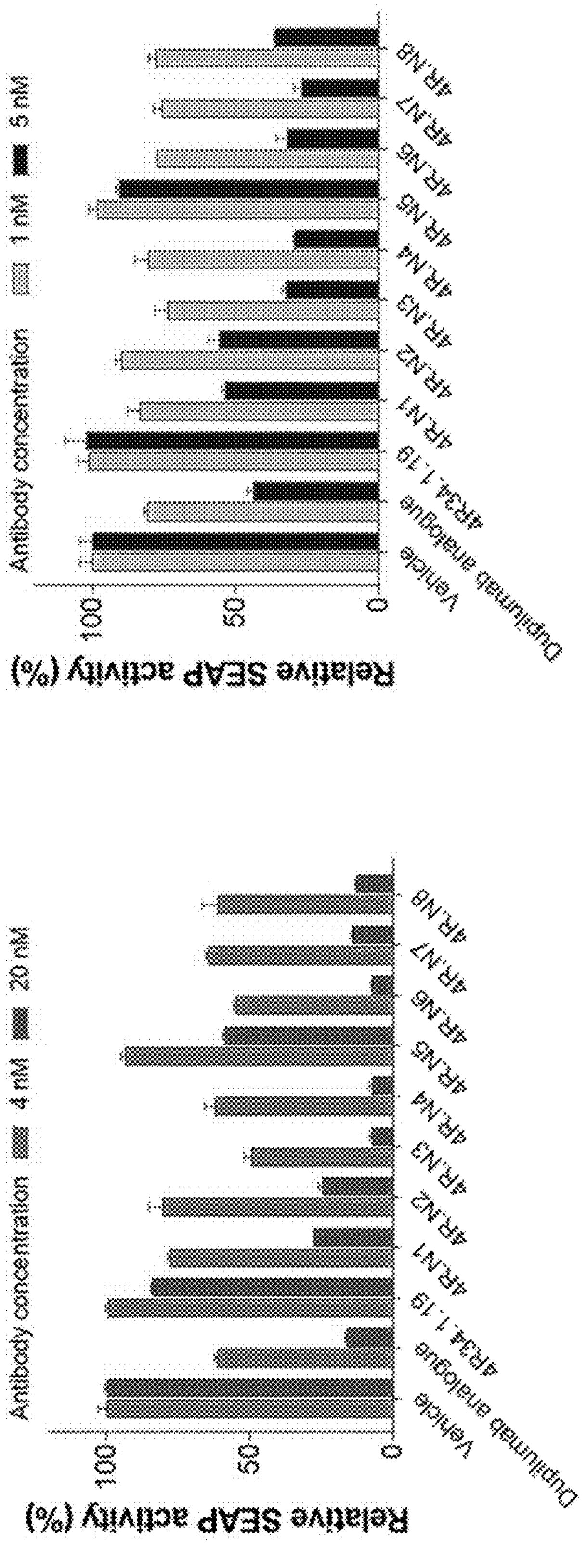

【FIG. 4A】
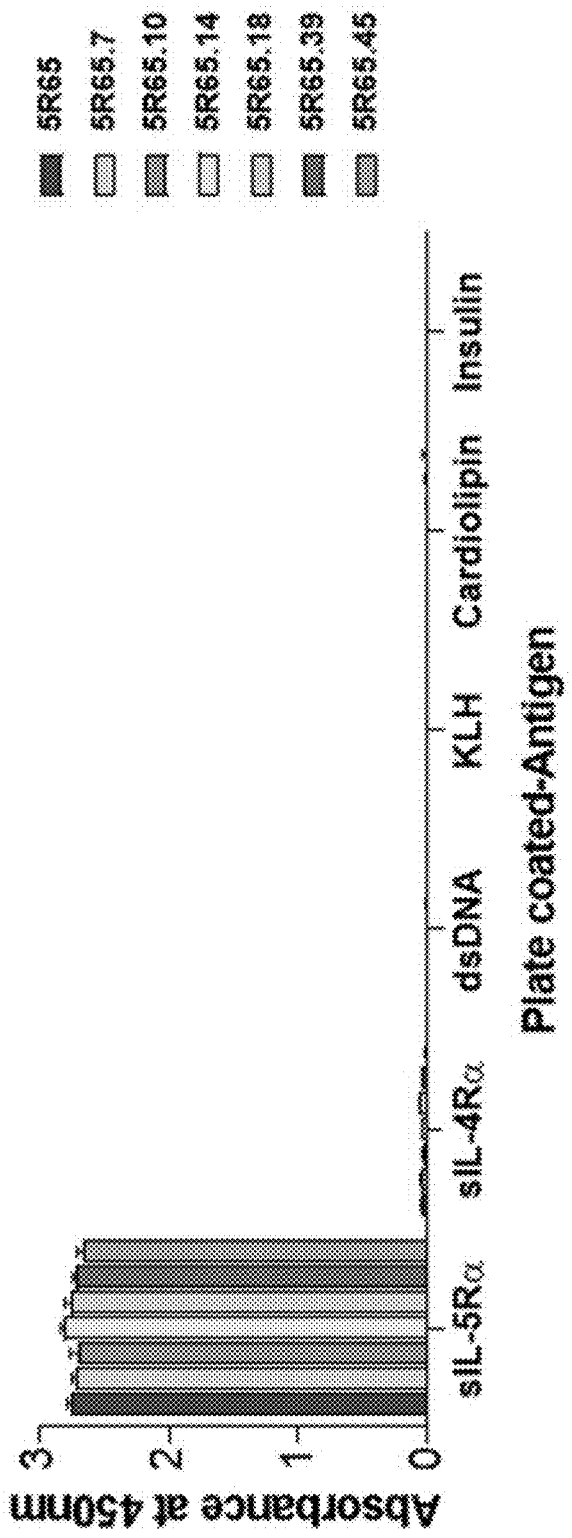

【FIG. 4B】
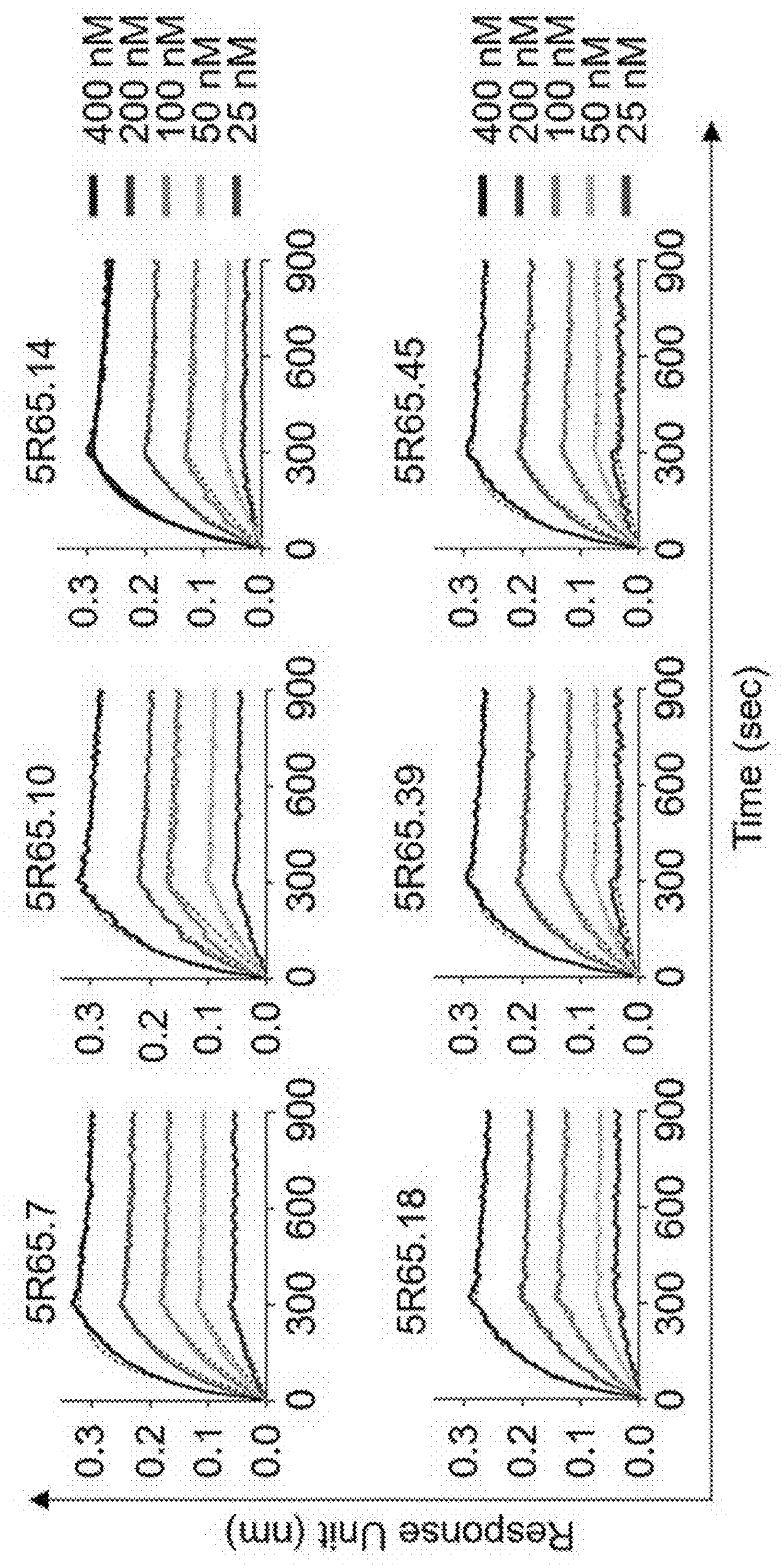

【FIG. 5A】
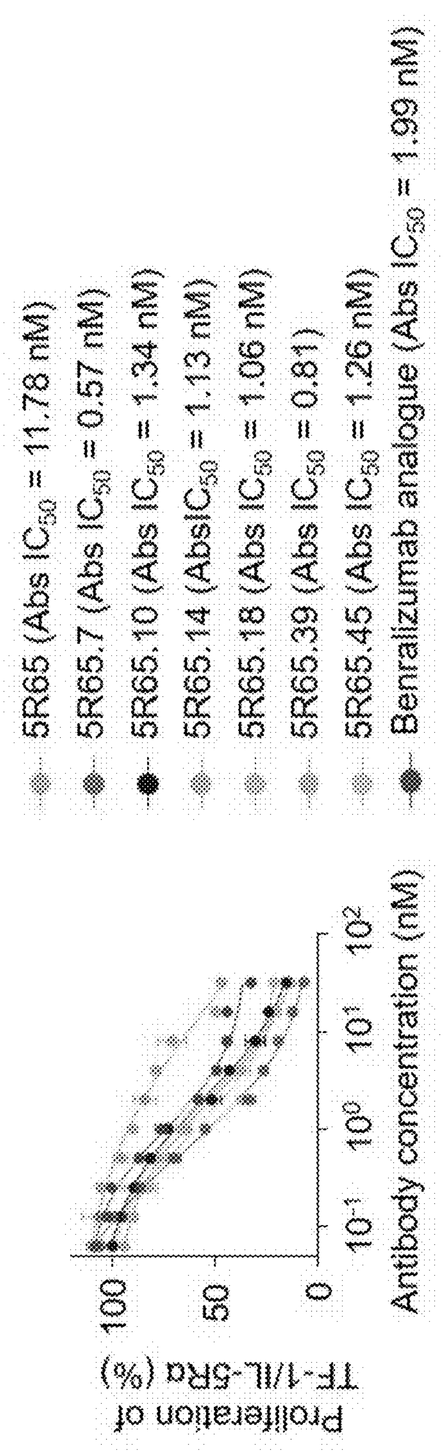
【FIG. 5B】
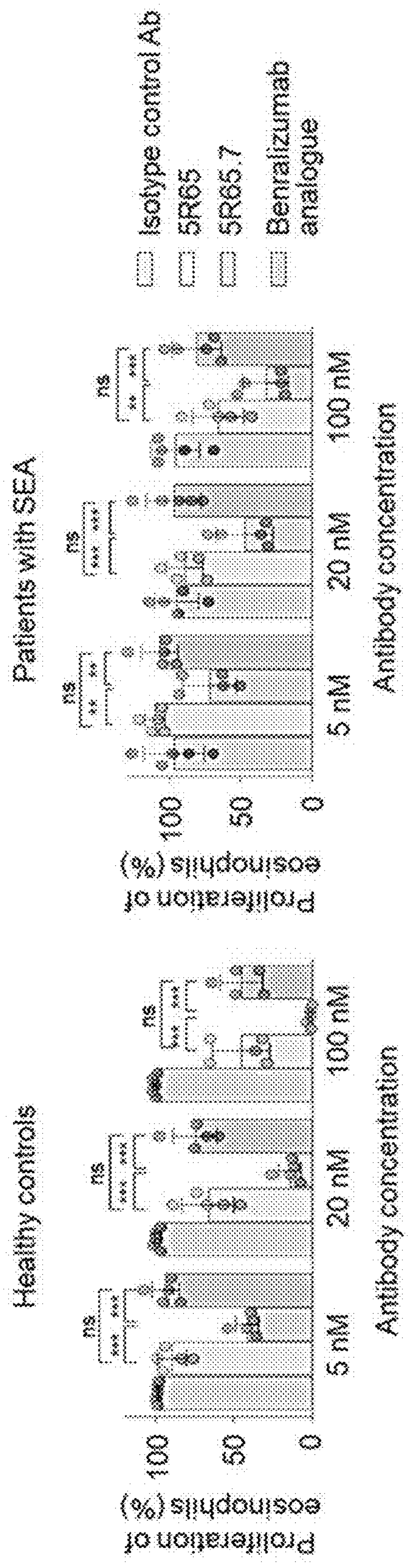

【FIG. 5C】
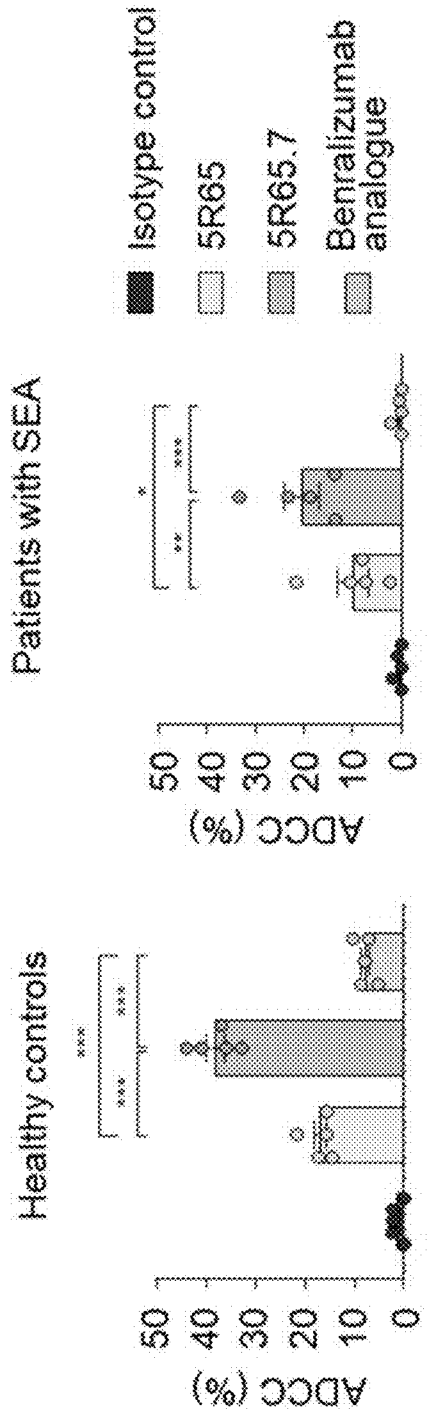

【FIG. 6】

| Schematic diagram | BiAb Format | Feature | Clone |
|---|---|---|---|
| 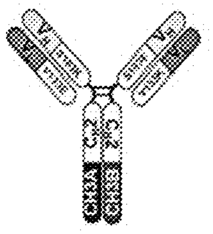 | IgG like bispecific antibody | -1+1 antigen-binding valency<br>- Heterodimer Fc | scIgG |
| | | | BsIgG |
| 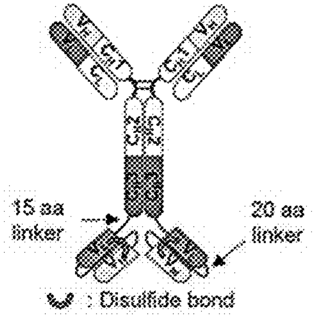 | IgG-scFv (IgG single chain Fv) | - 2+2 antigen-binding valency<br>- Opposite position of variable domain | 4R-IgG-5R-$_{HL}$scFv |
| | | | 4R-IgG-5R-$_{LH}$scFv |
| | | | 5R-IgG-4R-$_{HL}$scFv |
| | | | 5R-IgG-4R-$_{LH}$scFv |
| 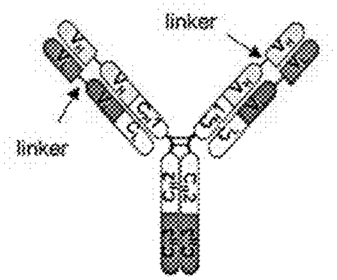 | Dual variable domain IgG (DVD-Ig) | - 2+2 antigen-binding valency<br>- Juxtaposition of variable domain | 4R-LL-5R |
| | | | 4R-SL-5R |
| | | | 5R-LL-4R |
| | | | 5R-SL-4R |

- 4R : IL-4Rα targeting Ab
- 5R : IL-5Rα targeting Ab
- HL : VH-VL
- LH : VL-VH
- LL : long linker
- SL : short linker 【FIG. 7A】
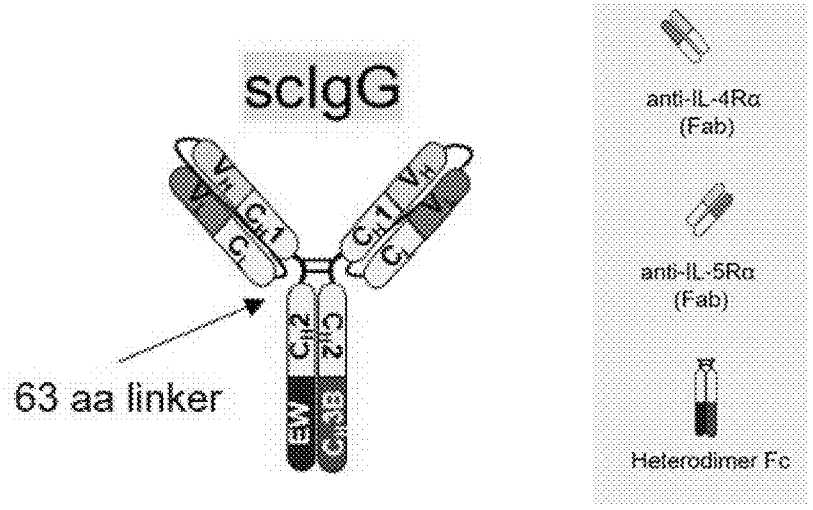
【FIG. 7B】
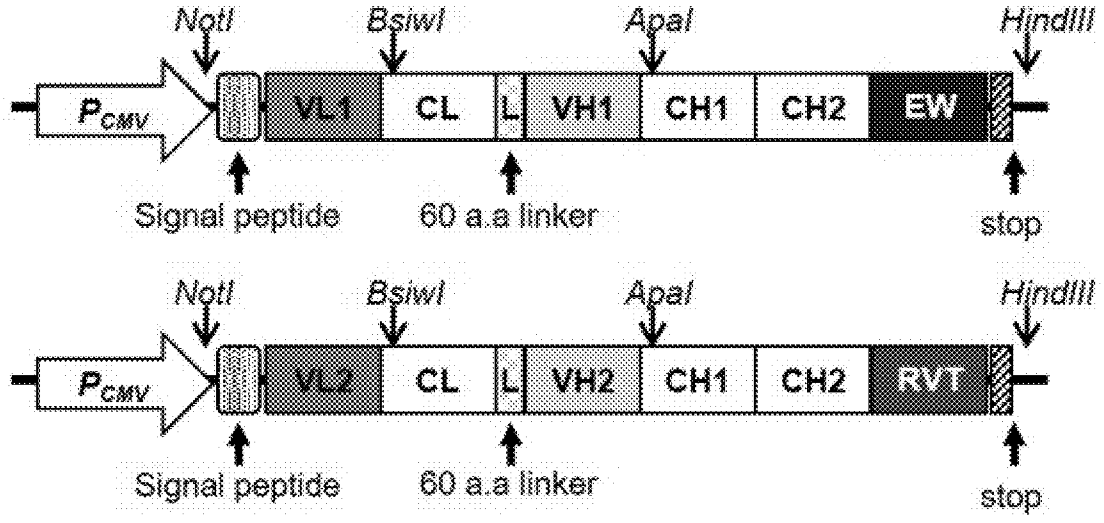

【FIG. 7C】
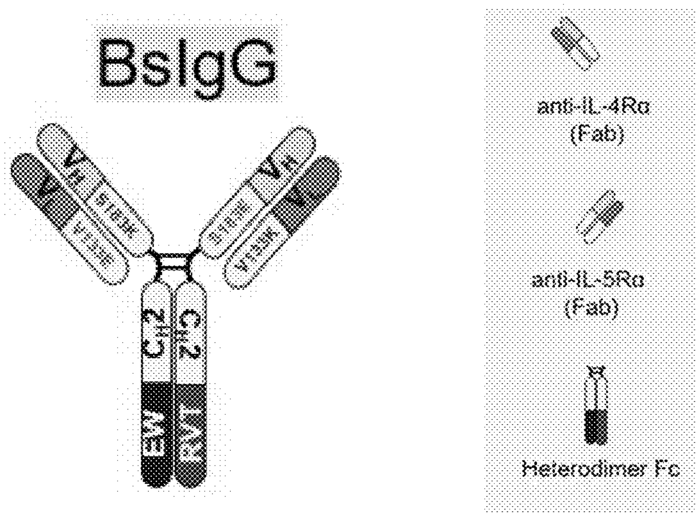

【FIG. 7D】
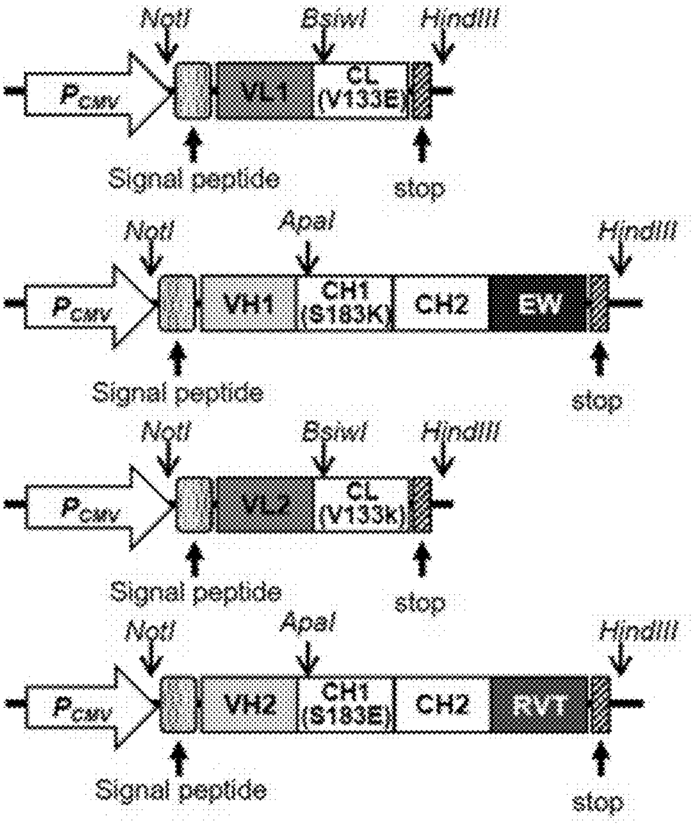

【FIG. 8A】
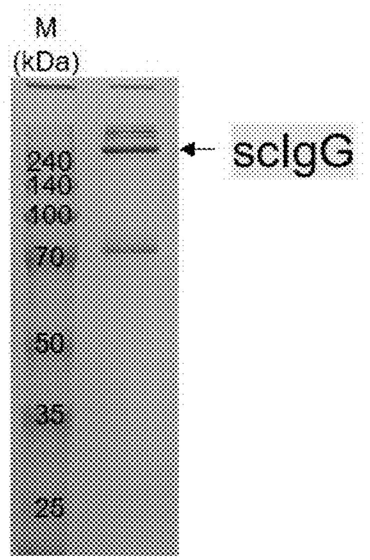
【FIG. 8B】
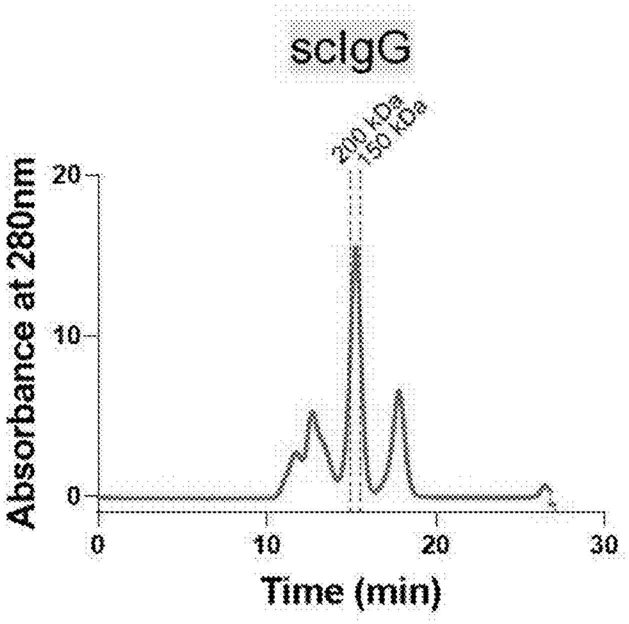

【FIG. 8C】
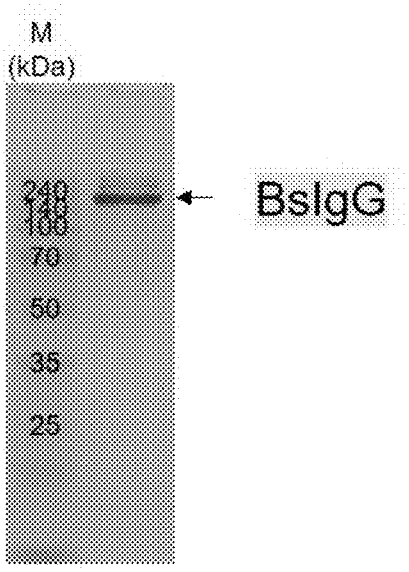
【FIG. 8D】
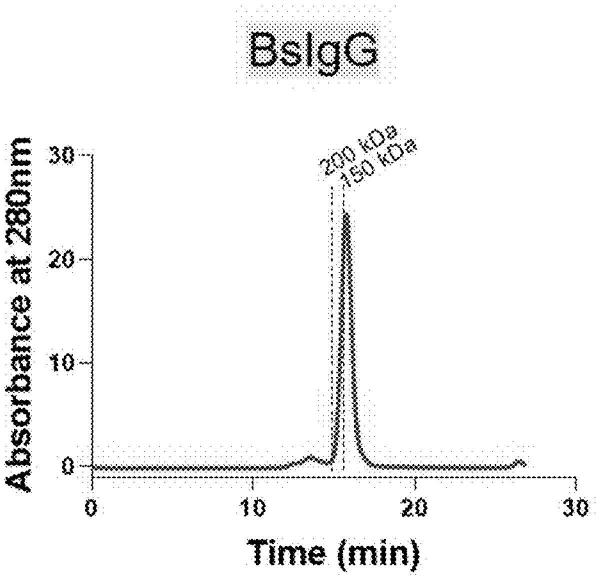

【FIG. 9A】
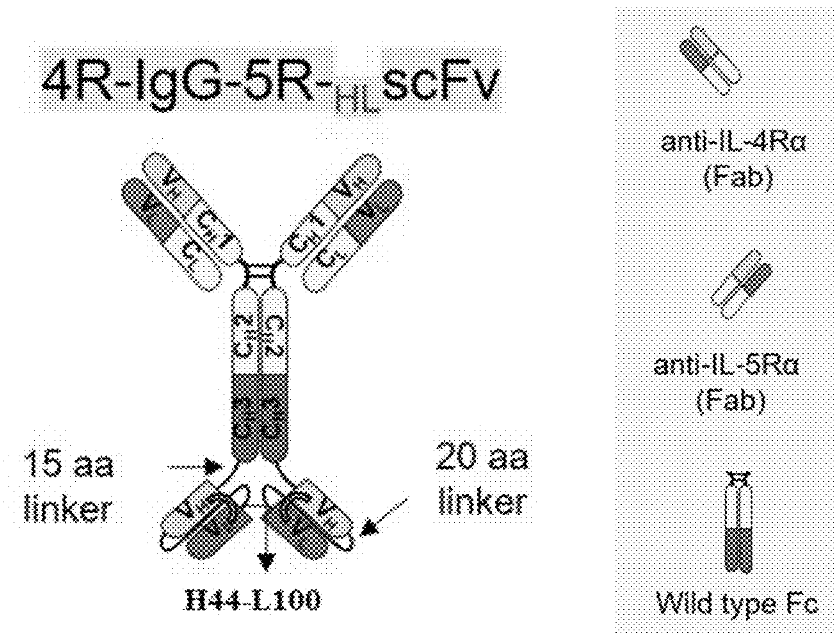

【FIG. 9B】
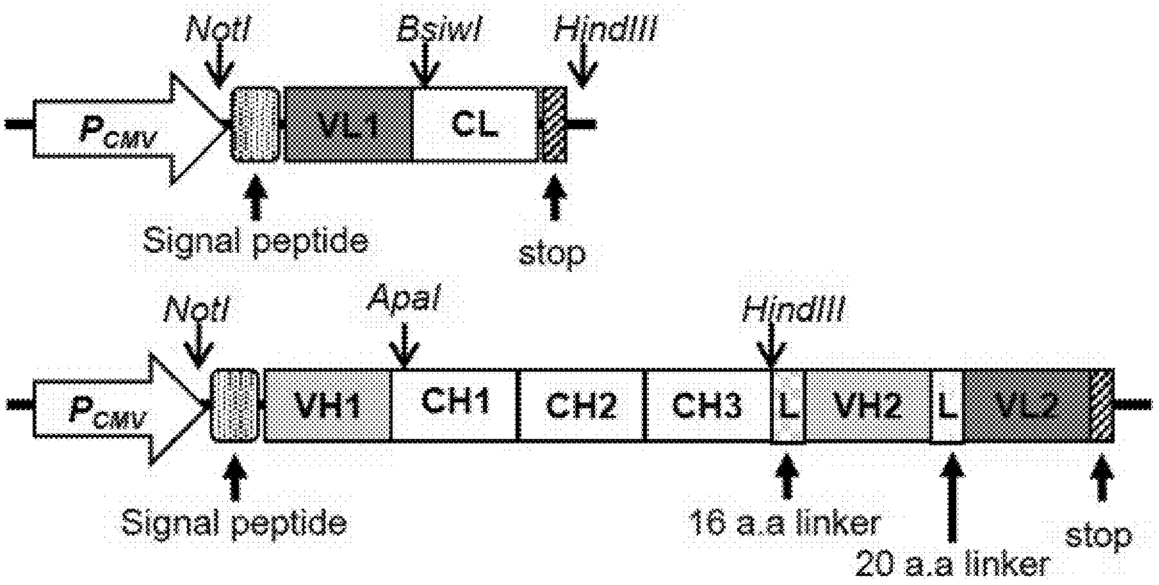

【FIG. 9C】
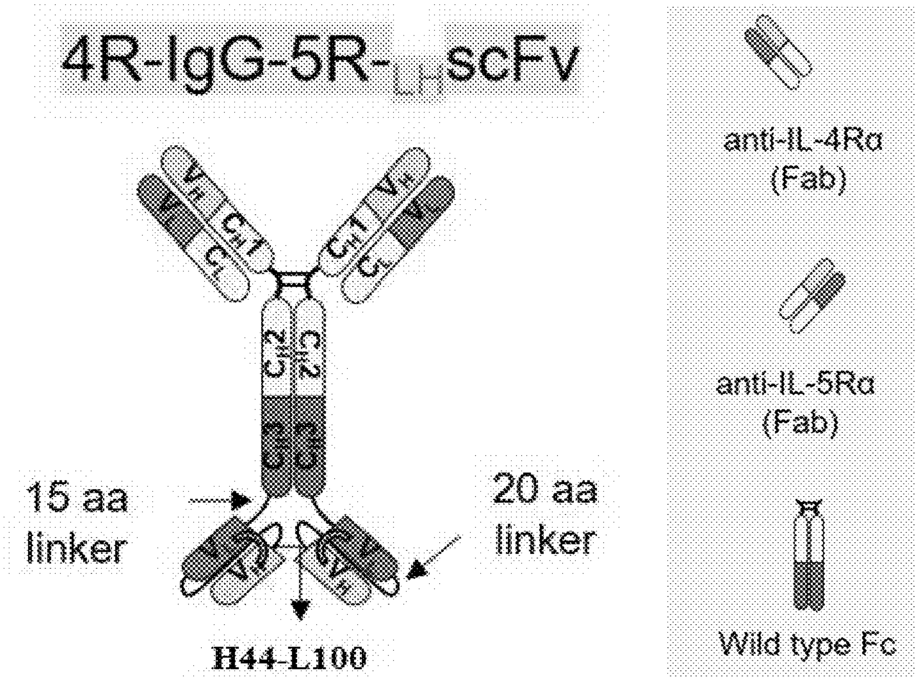

【FIG. 9D】
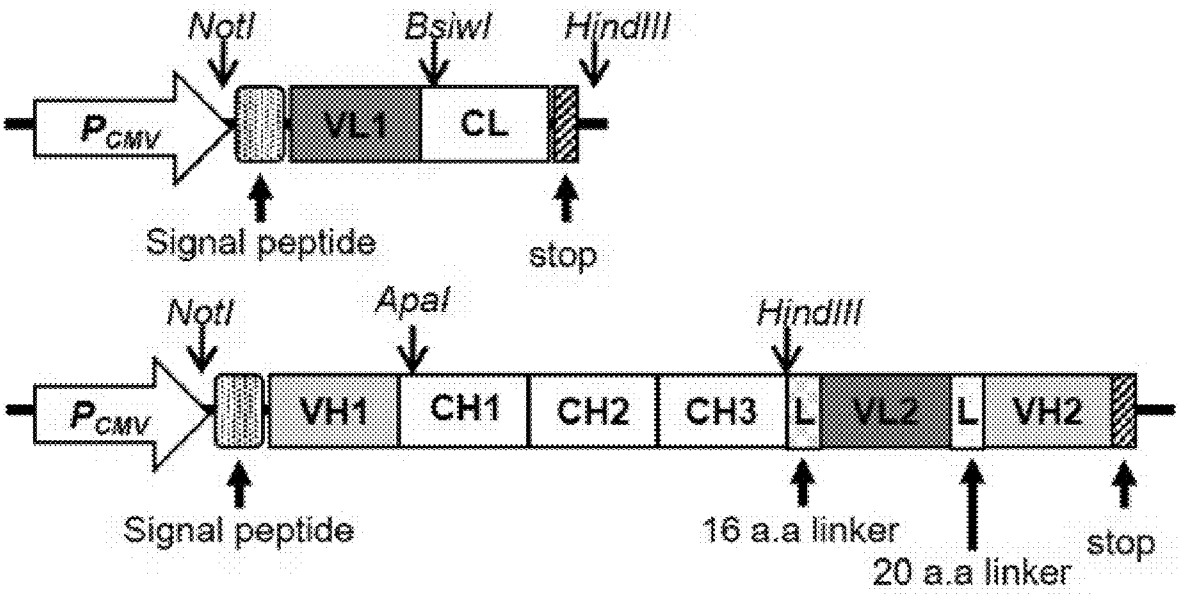

【FIG. 10A】
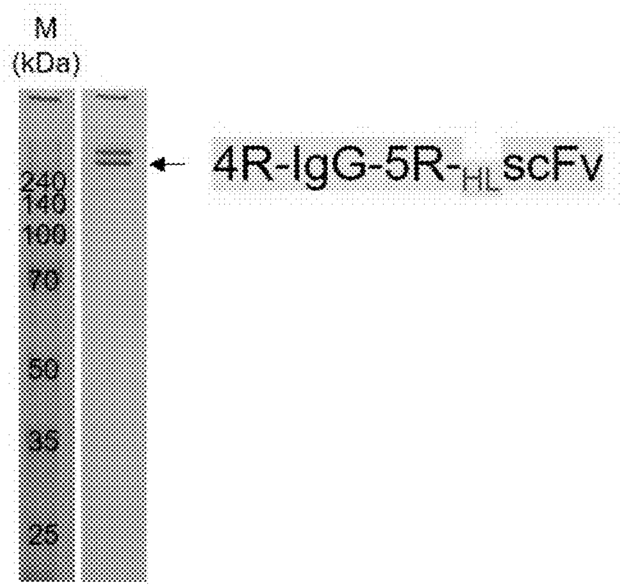
【FIG. 10B】
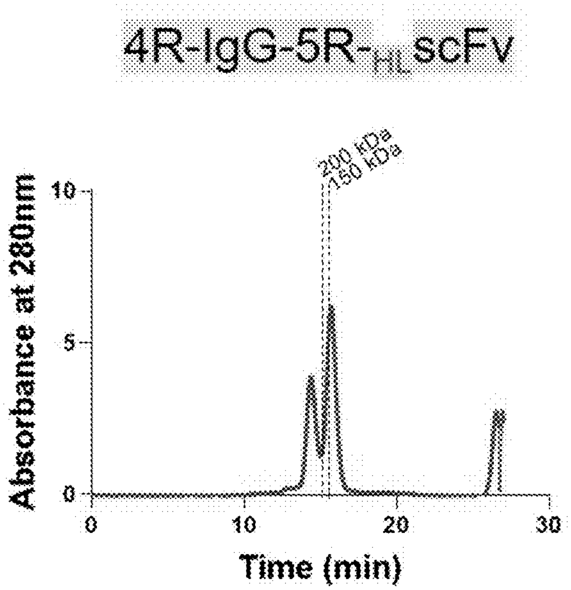

【FIG. 10C】
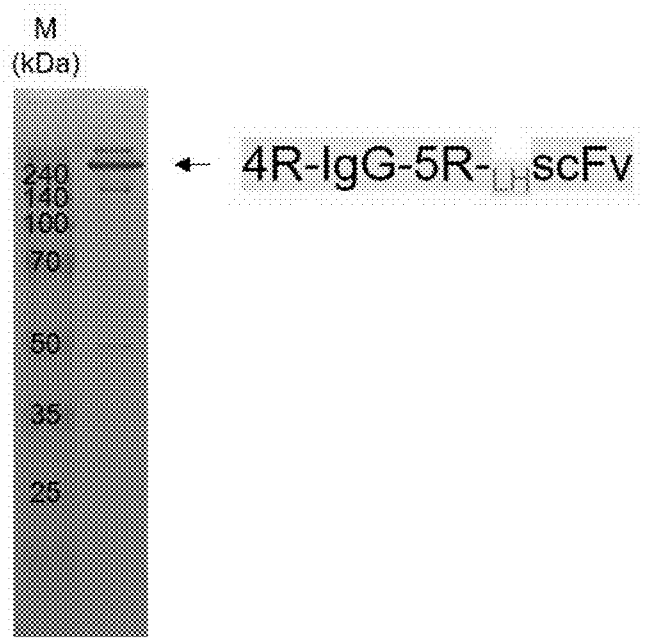
【FIG. 10D】
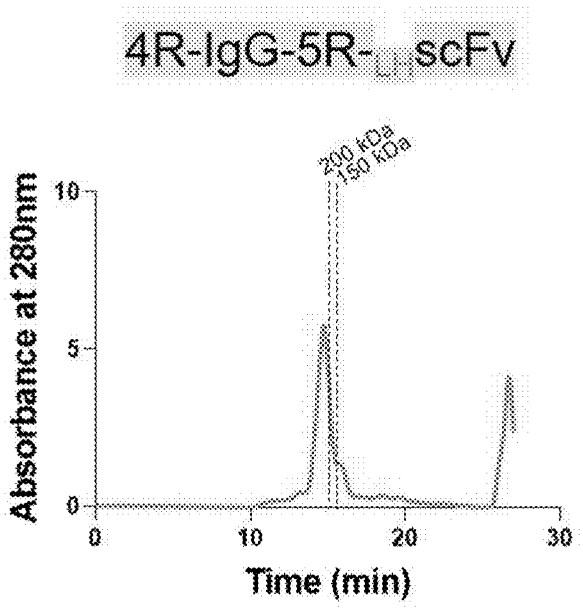

【FIG. 11A】
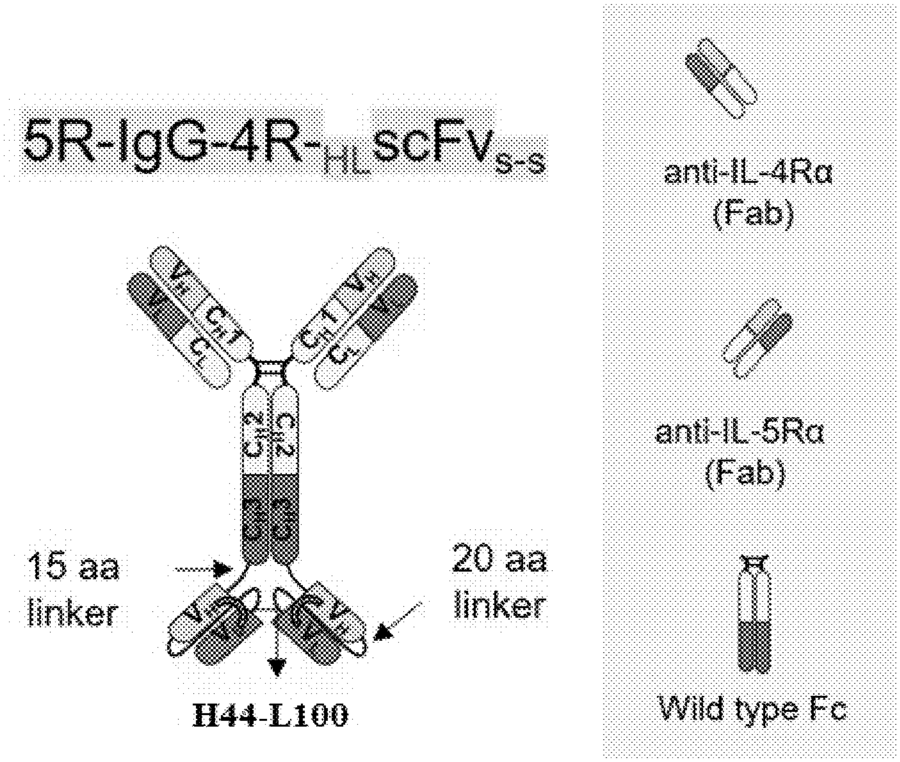
【FIG. 11B】
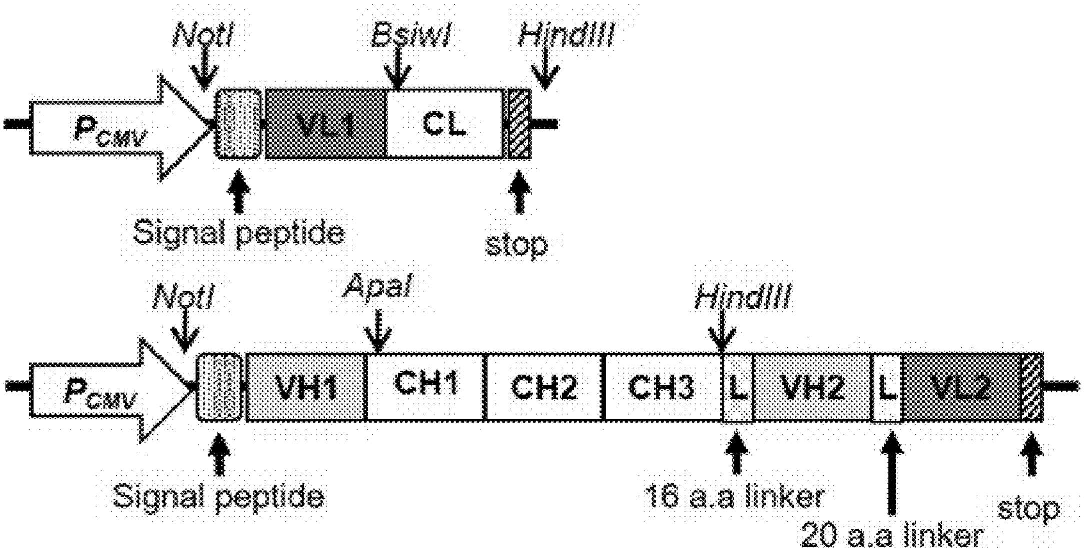

【FIG. 11C】
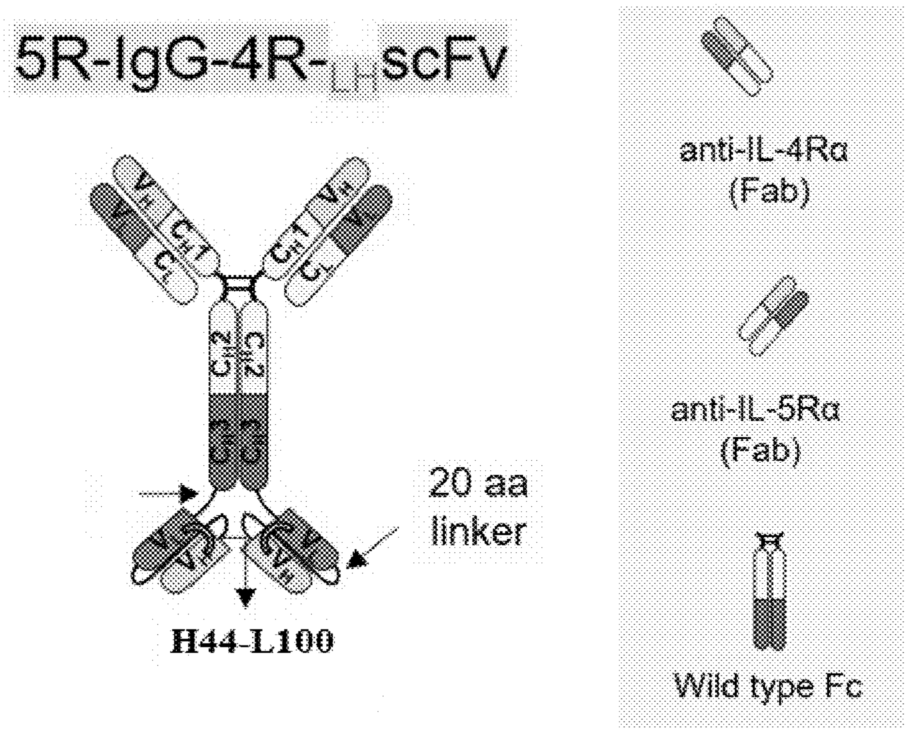
【FIG. 11D】
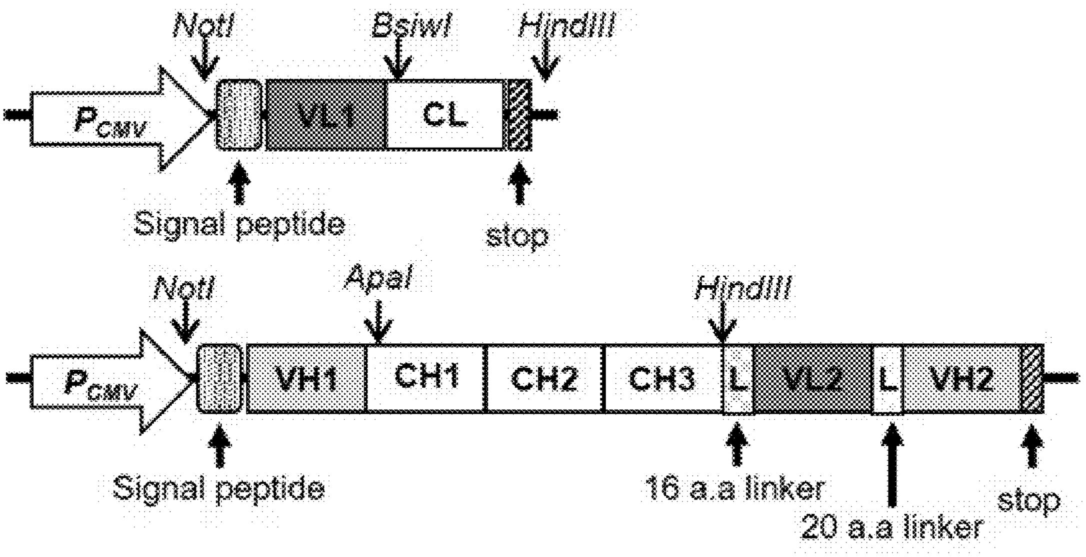

【FIG. 12A】
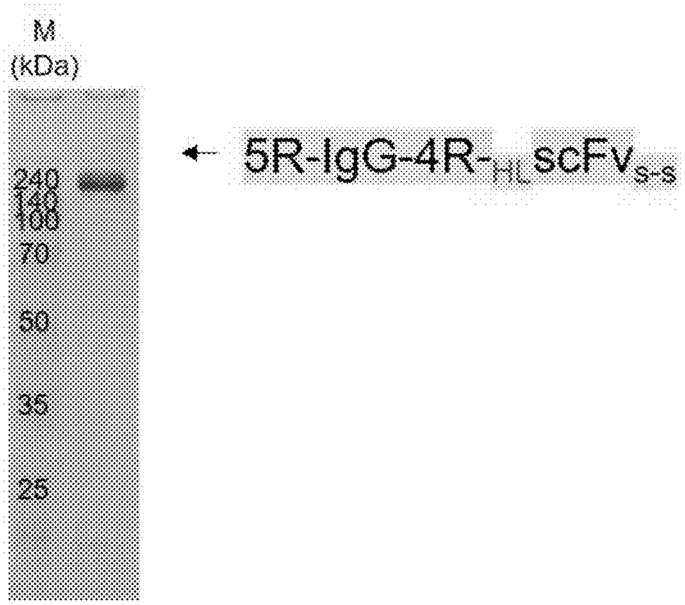
【FIG. 12B】
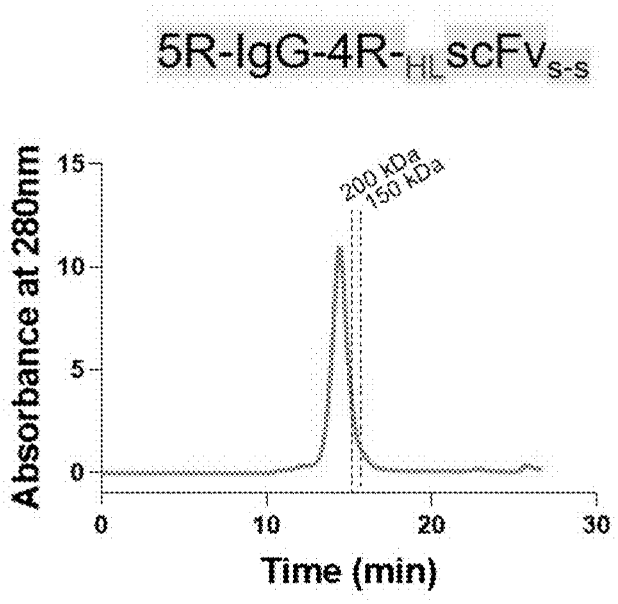

【FIG. 12C】
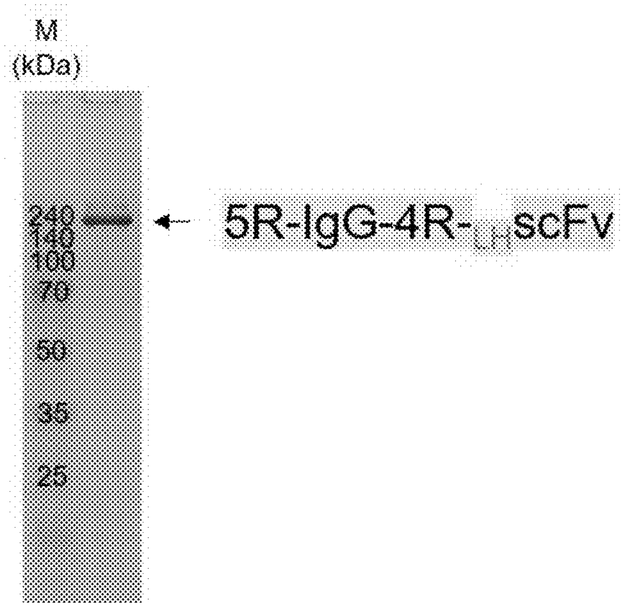
【FIG. 12D】
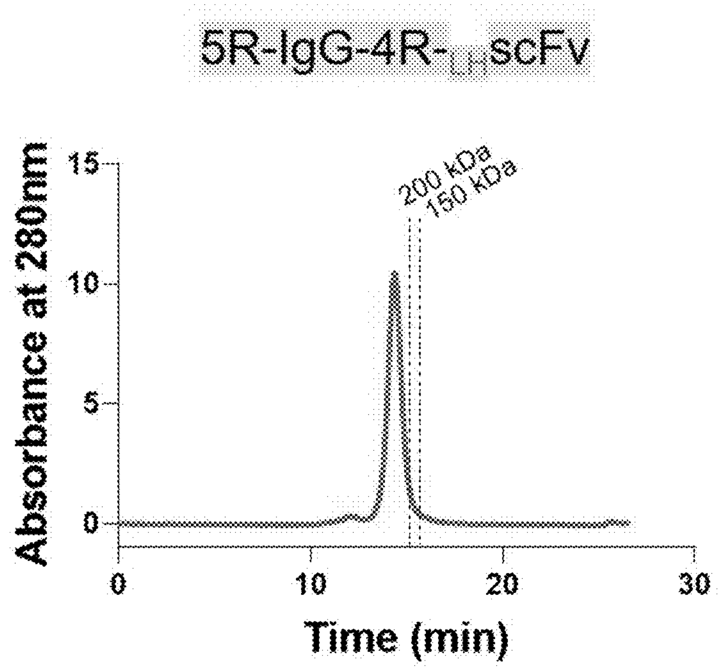

【FIG. 13】
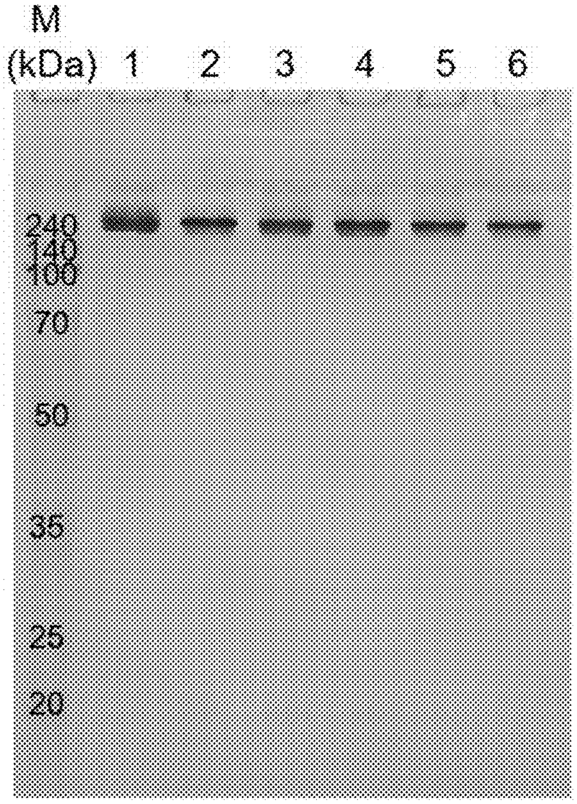
1. 5R65-IgG-4R34.1.19-$_{LH}$scFv
2. 5R65.7-IgG-4R.N3-$_{LH}$scFv
3. 5R65.7-IgG-4R.N4-$_{LH}$scFv
4. 5R65.7-IgG-4R.N6-$_{LH}$scFv
5. 5R65.7-IgG-4R.N7-$_{LH}$scFv
6. 5R65.7-IgG-4R.N8-$_{LH}$scFv 【FIG. 14】
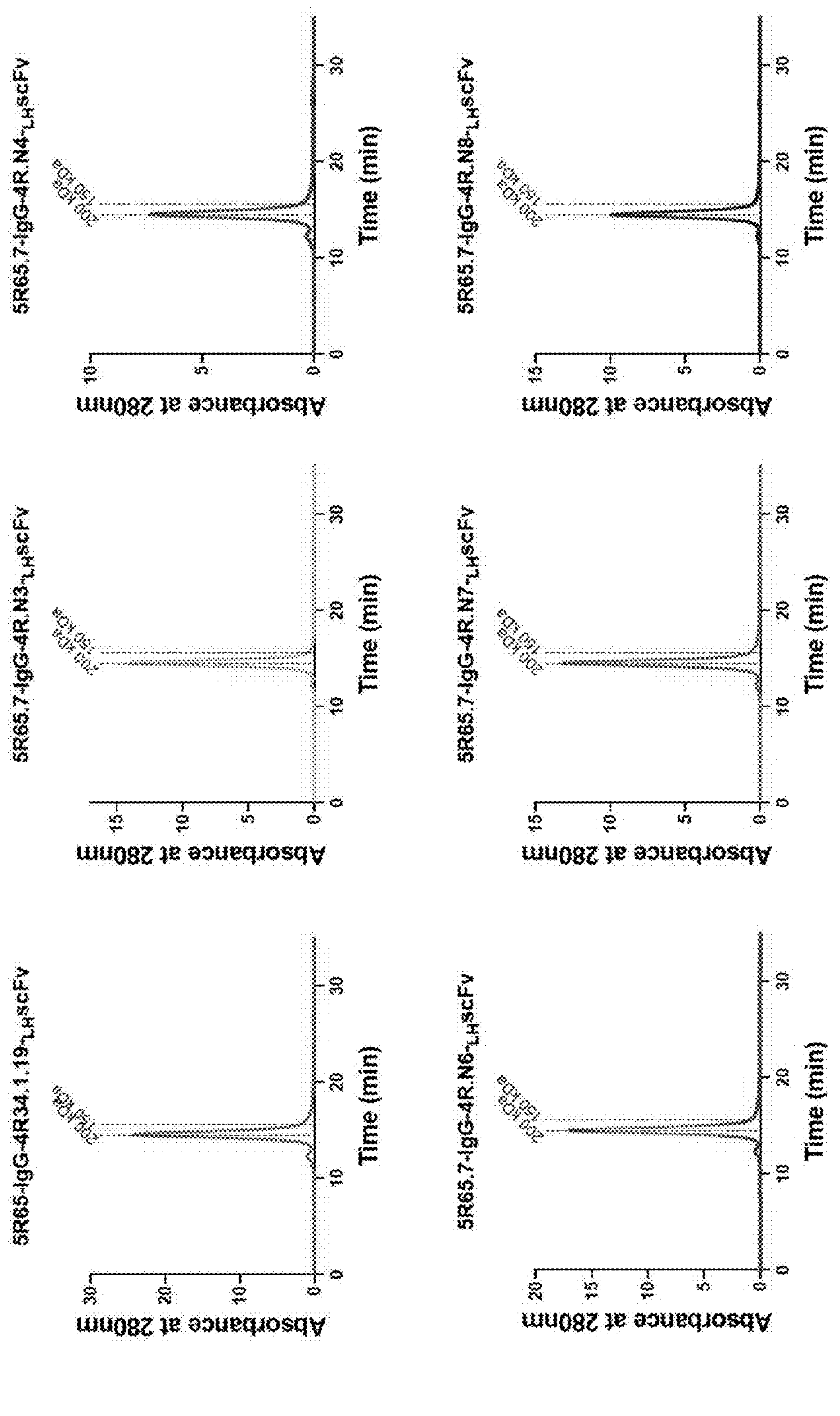

【FIG. 15A】
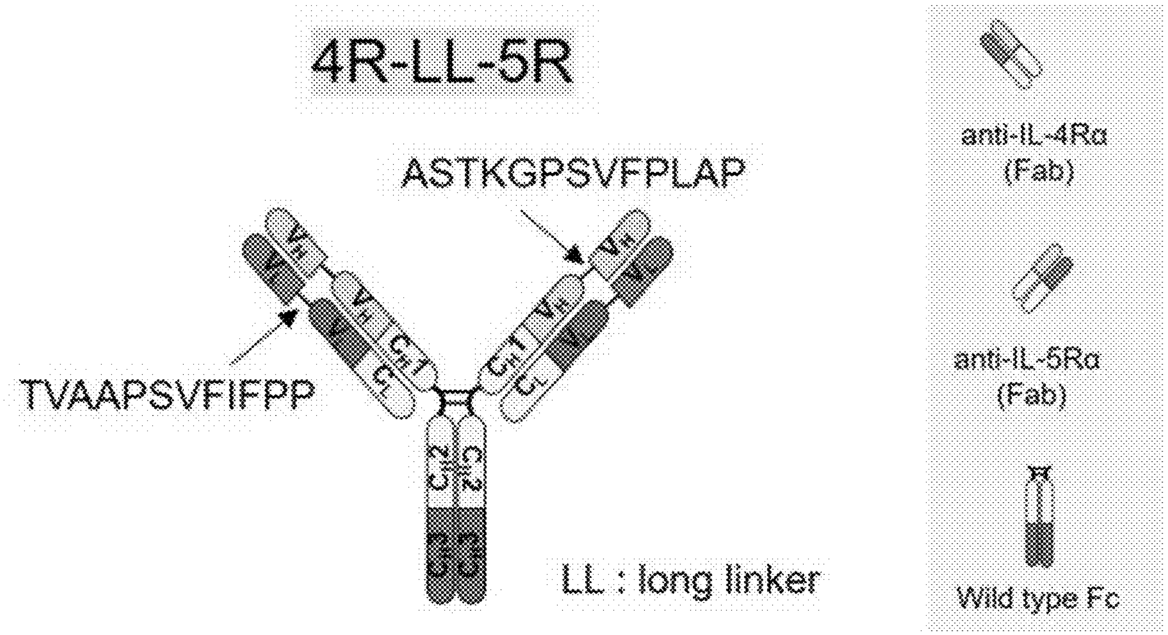
【FIG. 15B】
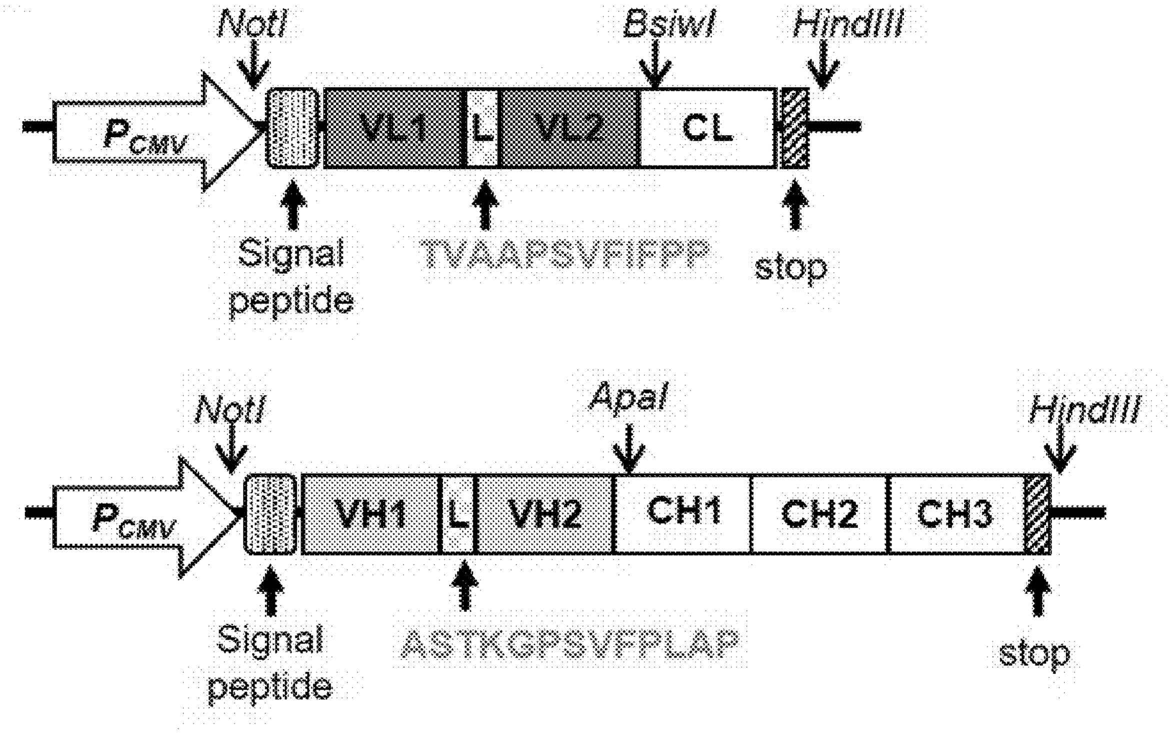

【FIG. 15C】
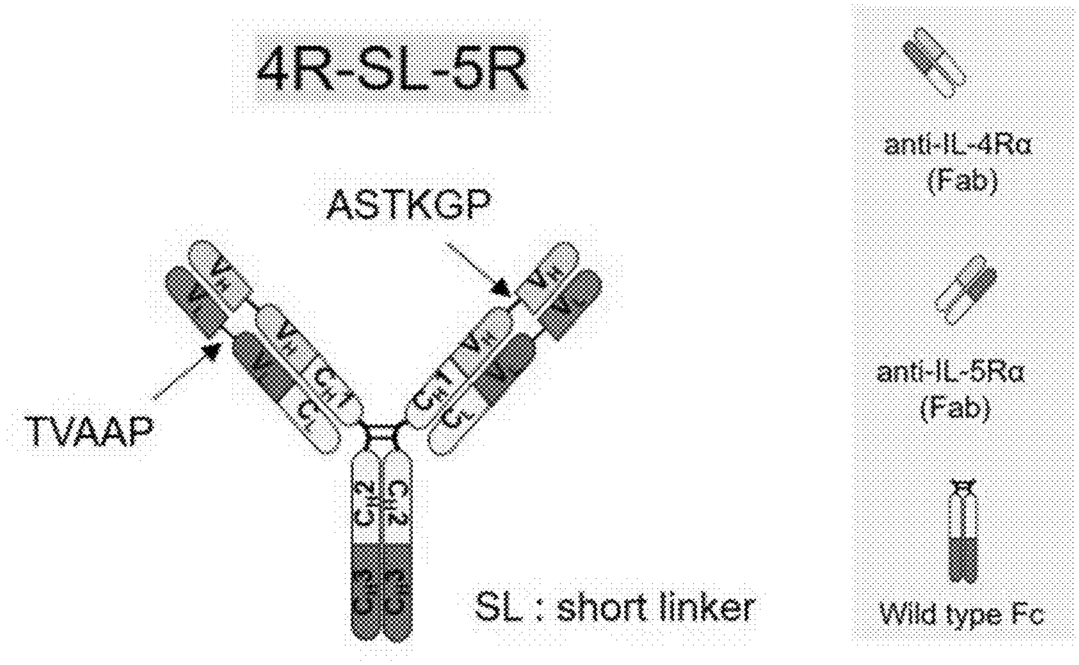
【FIG. 15D】
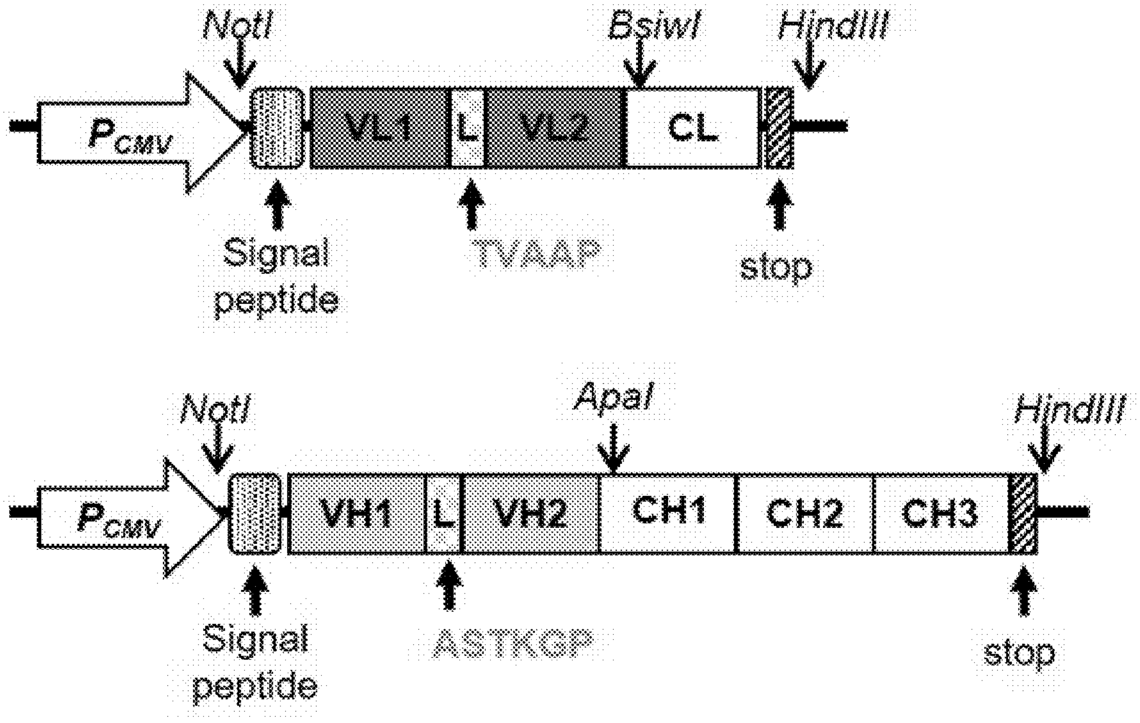

【FIG. 16A】
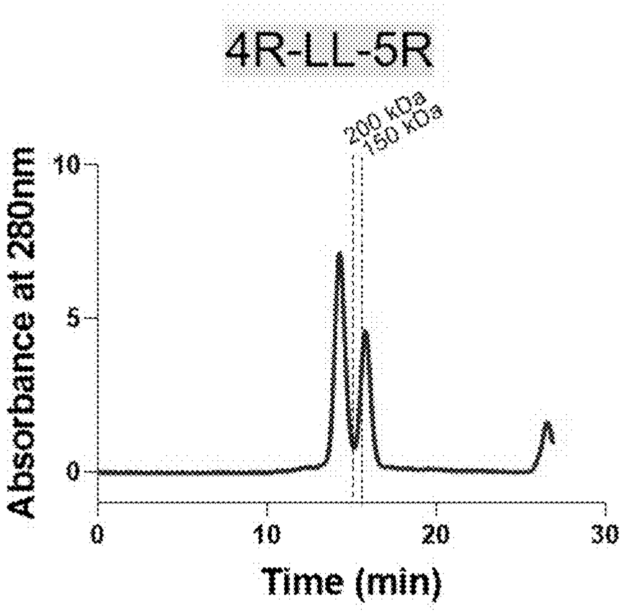
【FIG. 16B】
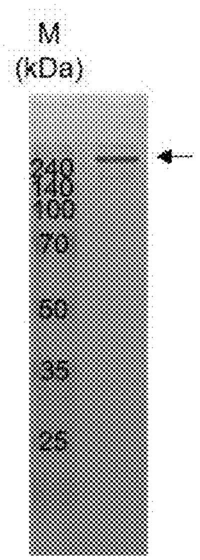

【FIG. 16C】
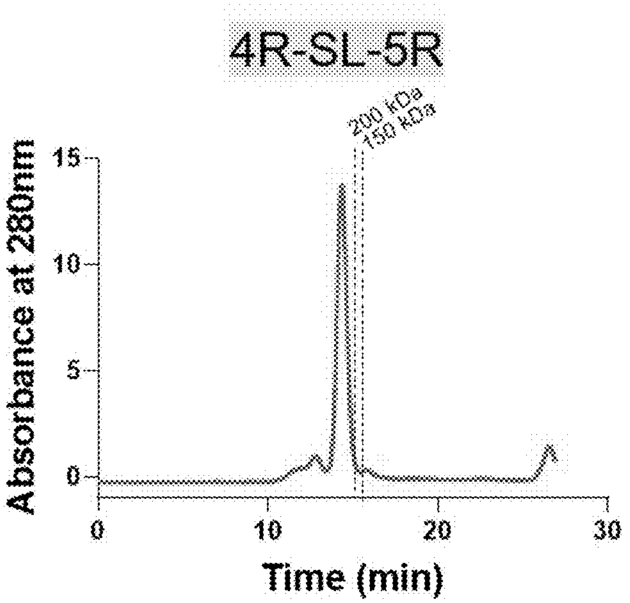

【FIG. 17A】
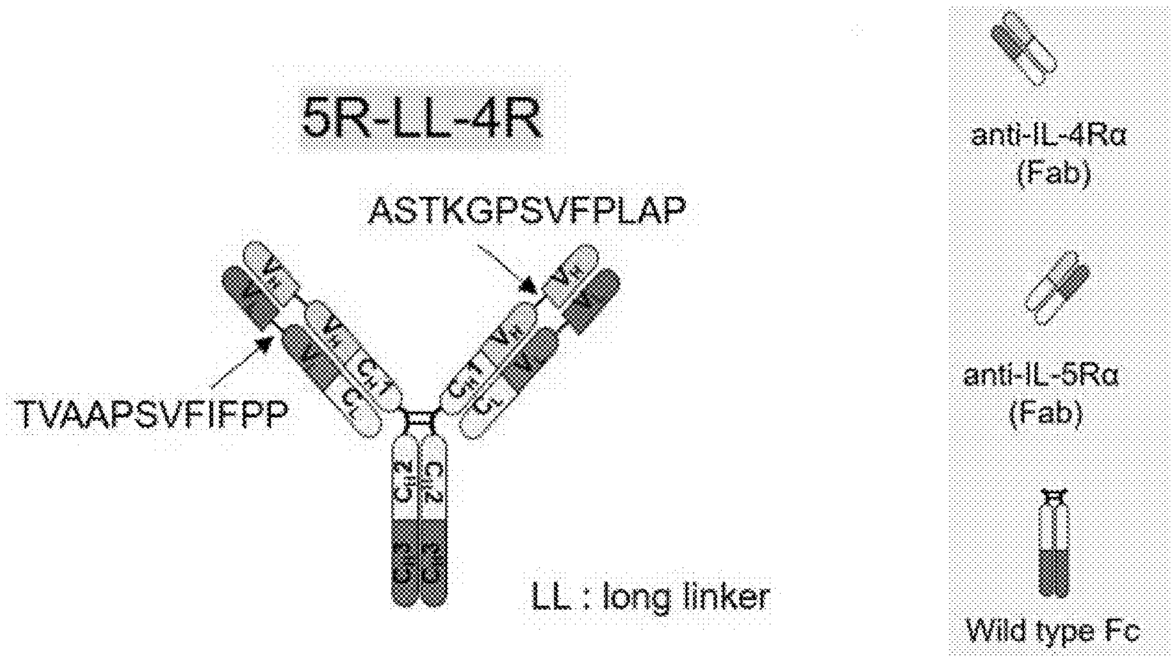
【FIG. 17B】
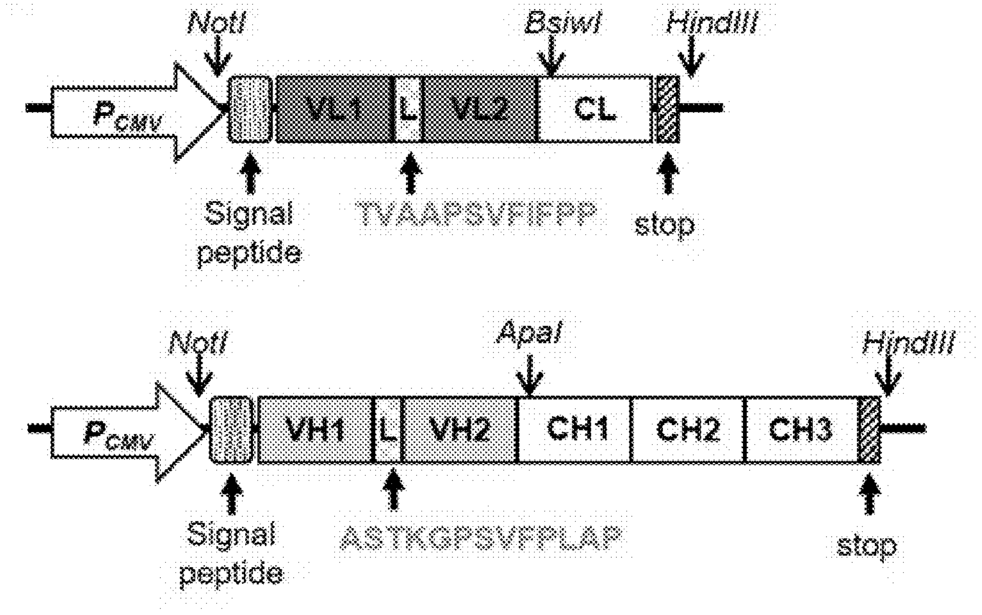

【FIG. 17C】
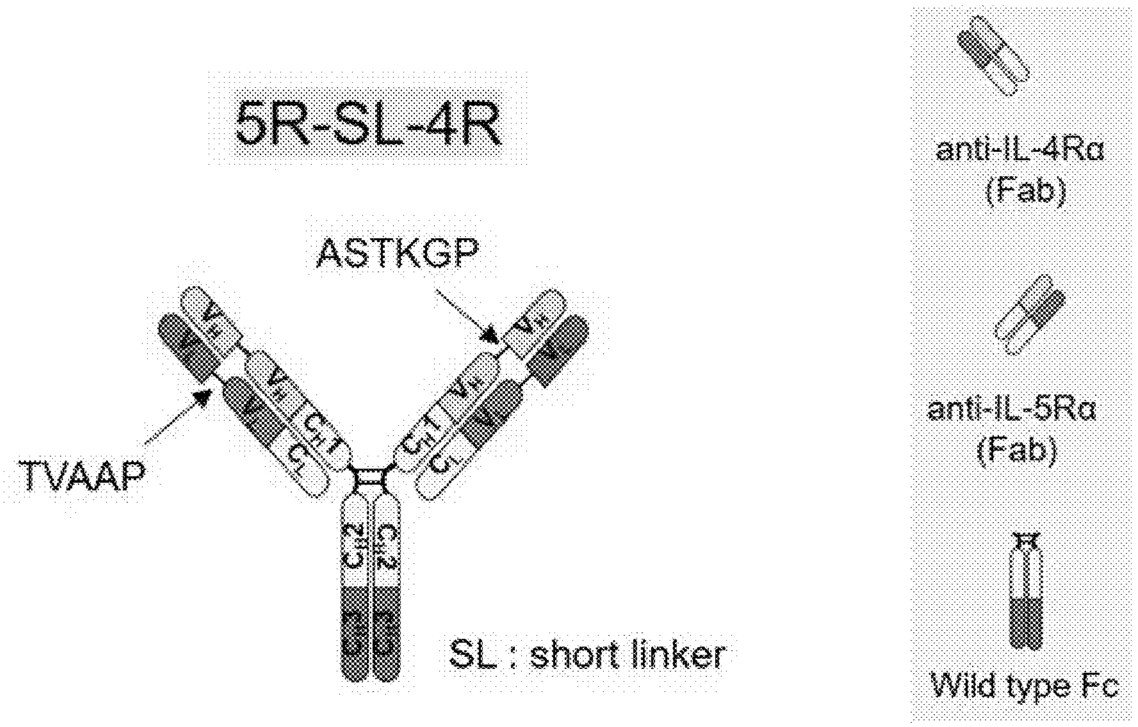
【FIG. 17D】
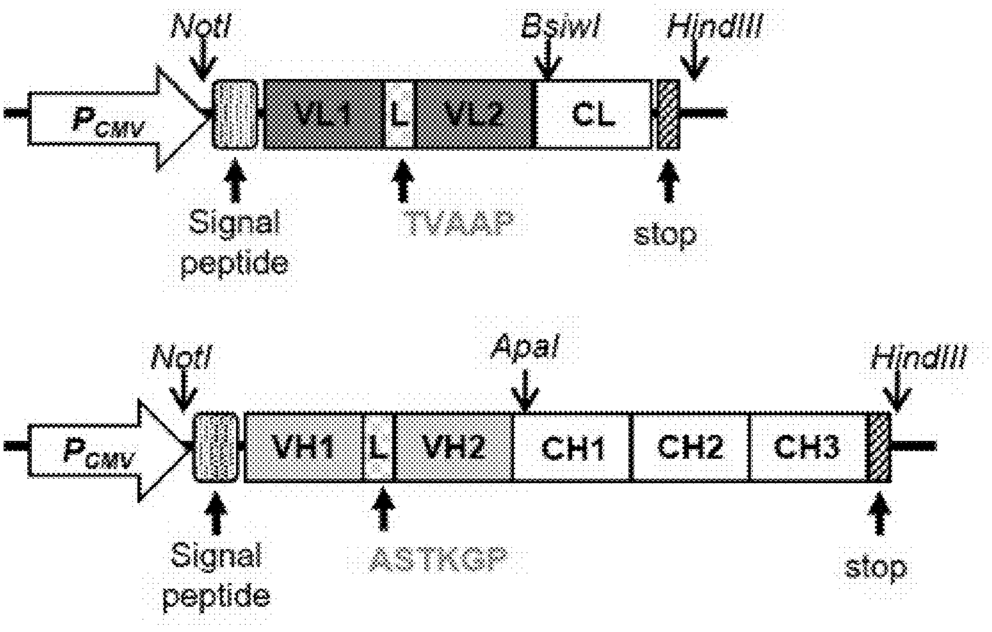

【FIG. 18A】
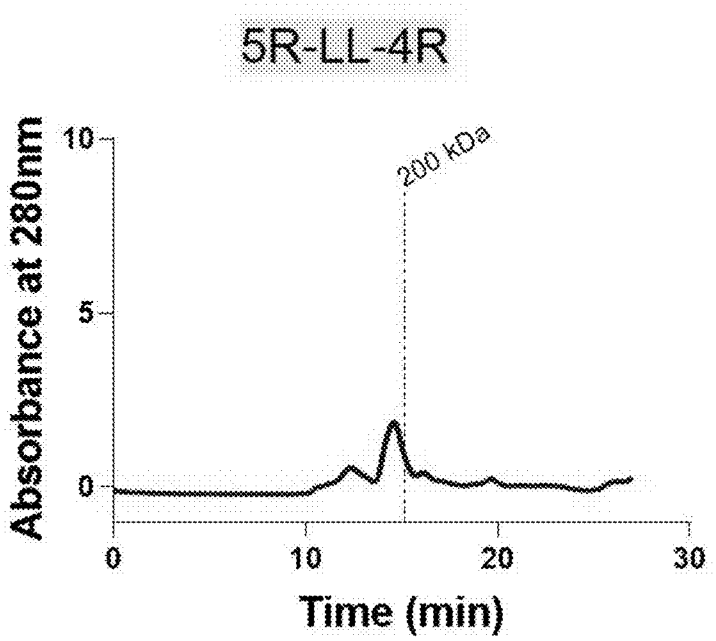
【FIG. 18B】
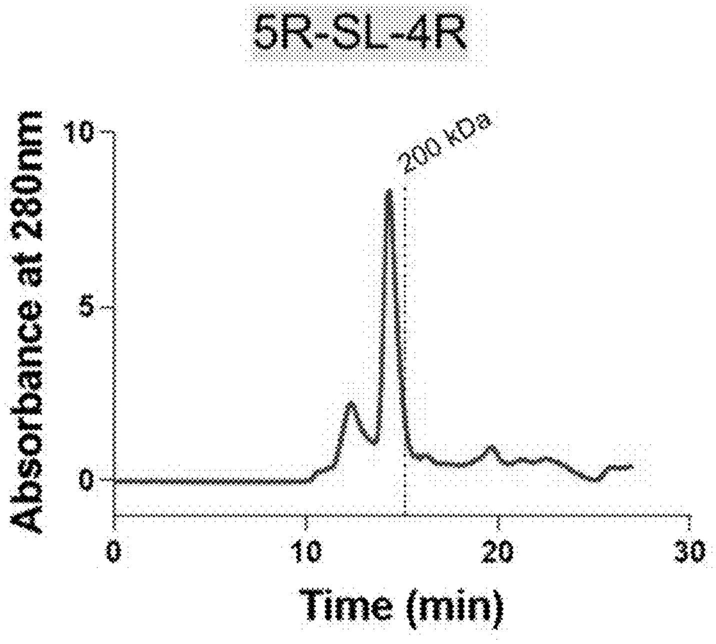

【FIG. 19】
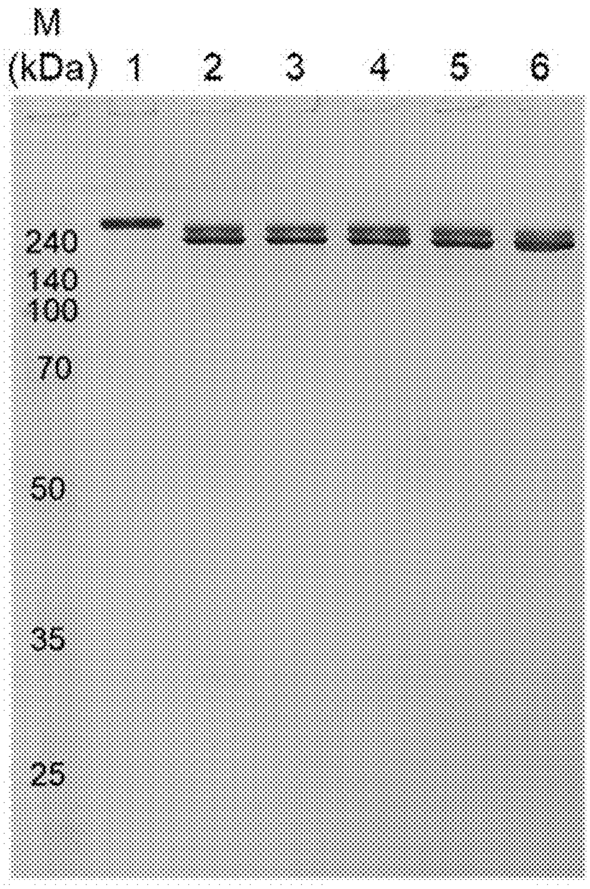
1. 4R34.1.19-SL-5R65
2. 4R.N3-SL-5R65.7
3. 4R.N4-SL-5R65.7
4. 4R.N6-SL-5R65.7
5. 4R.N7-SL-5R65.7
6. 4R.N8-SL-5R65.7

【FIG. 20】
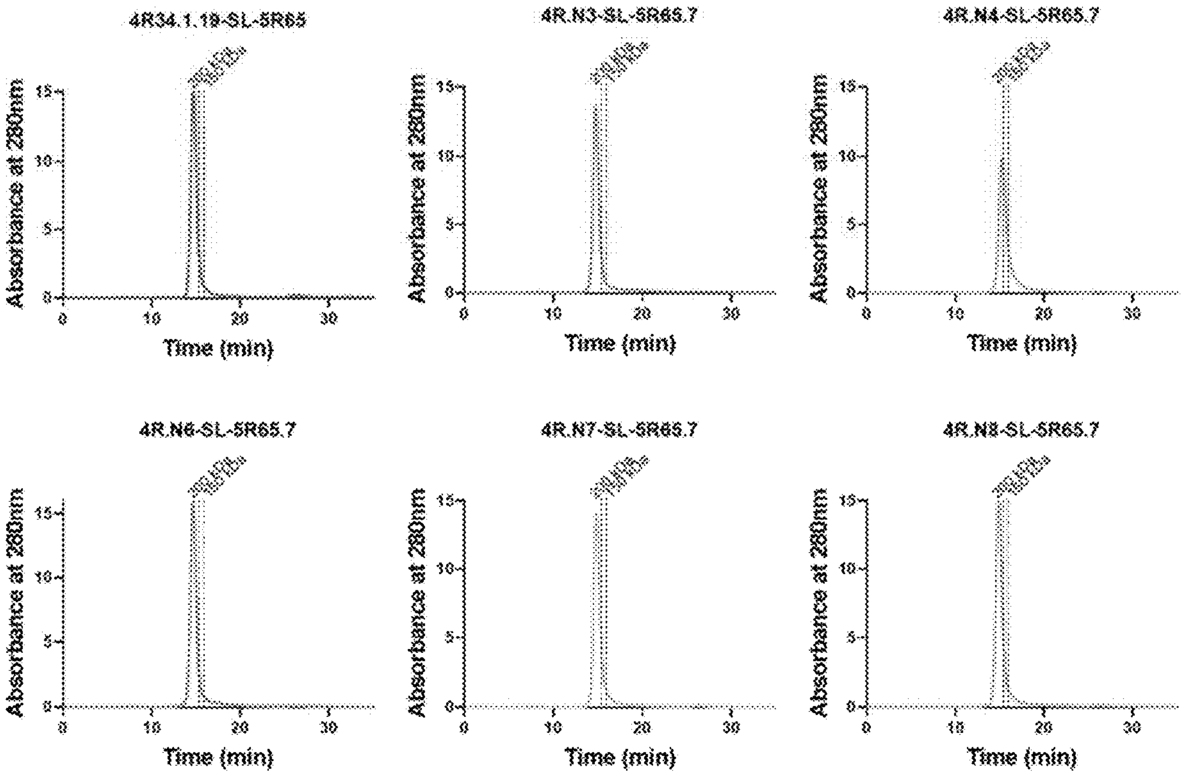

【FIG. 21】
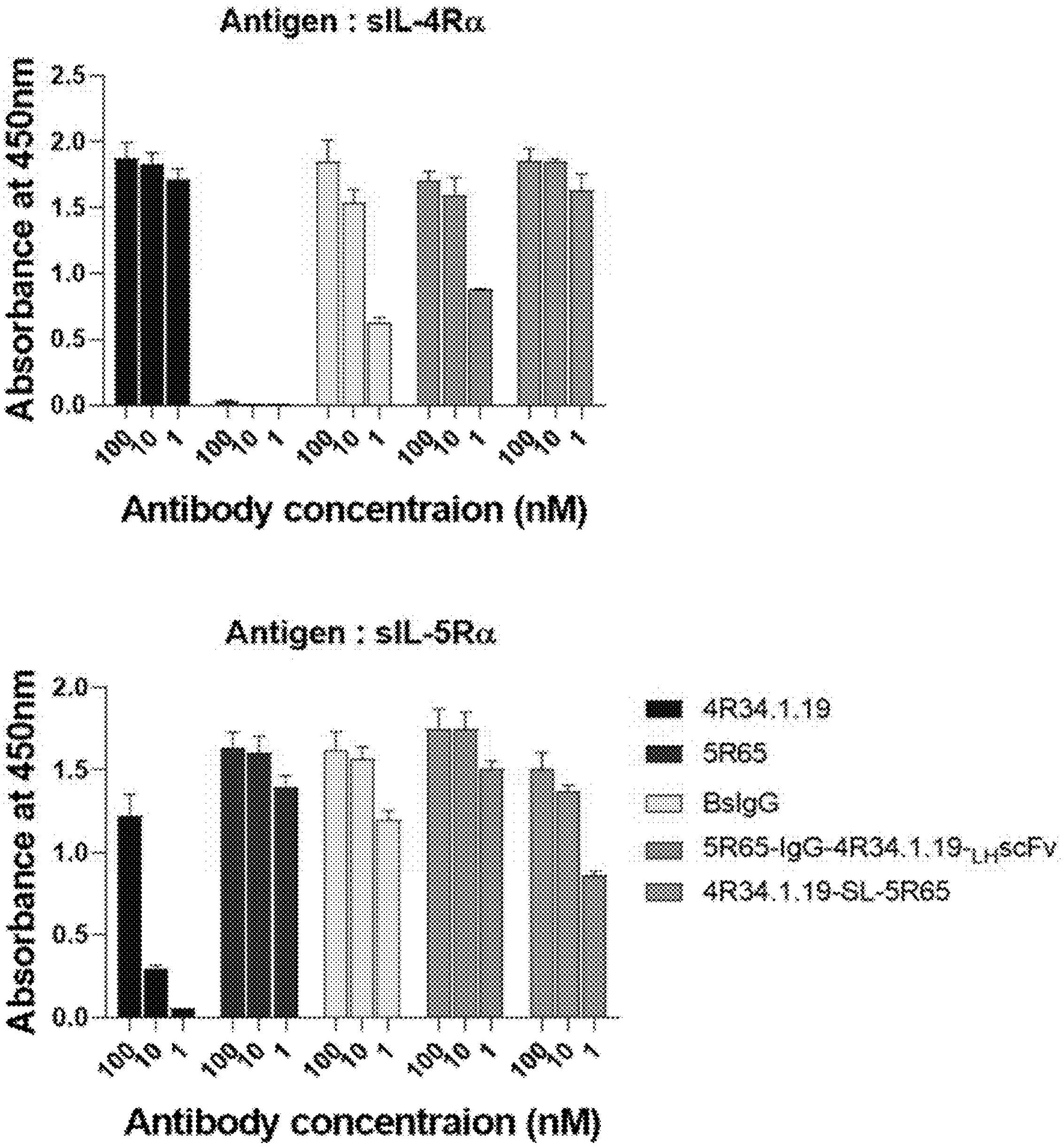

【FIG. 22】
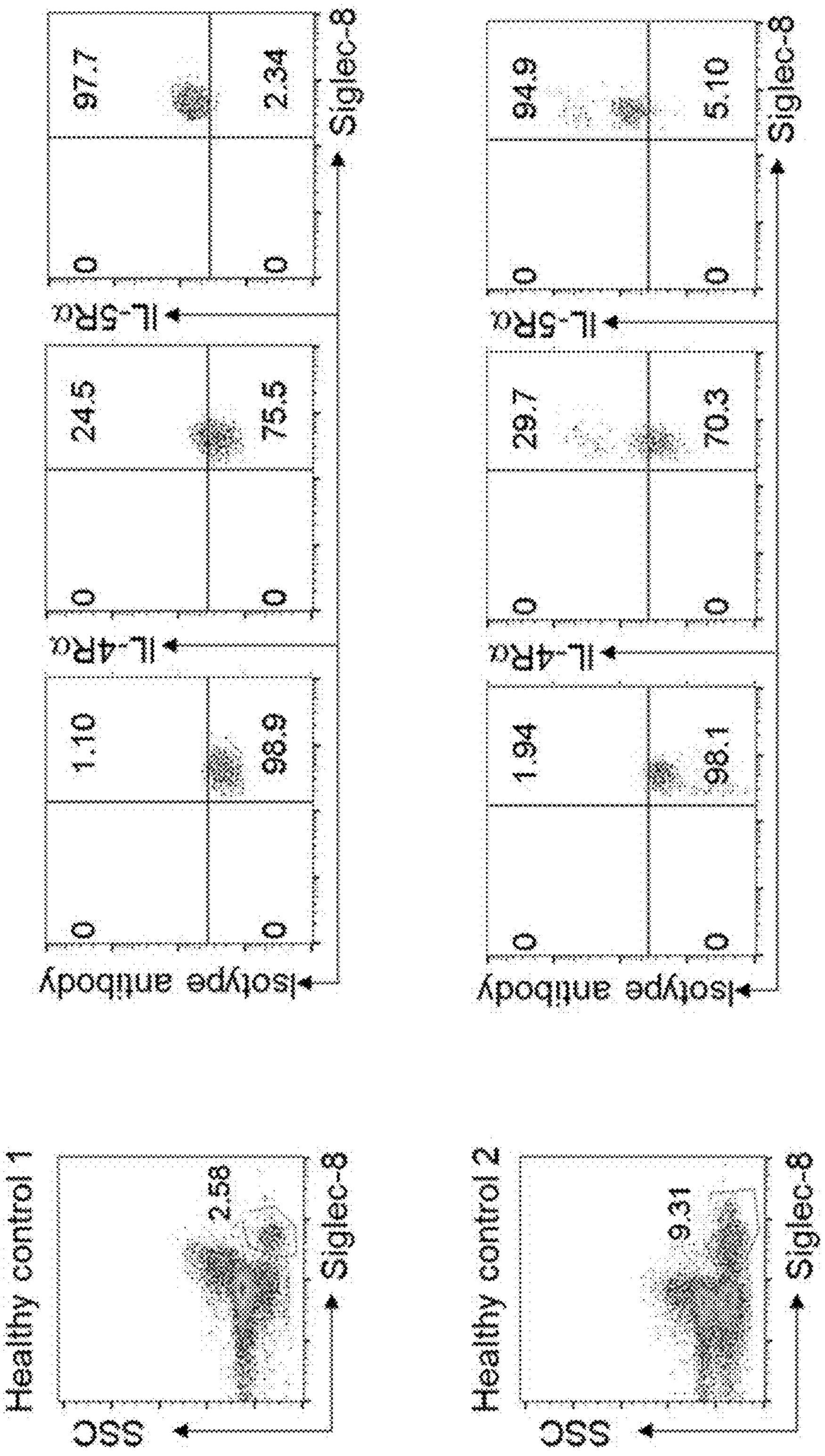

【FIG. 23】
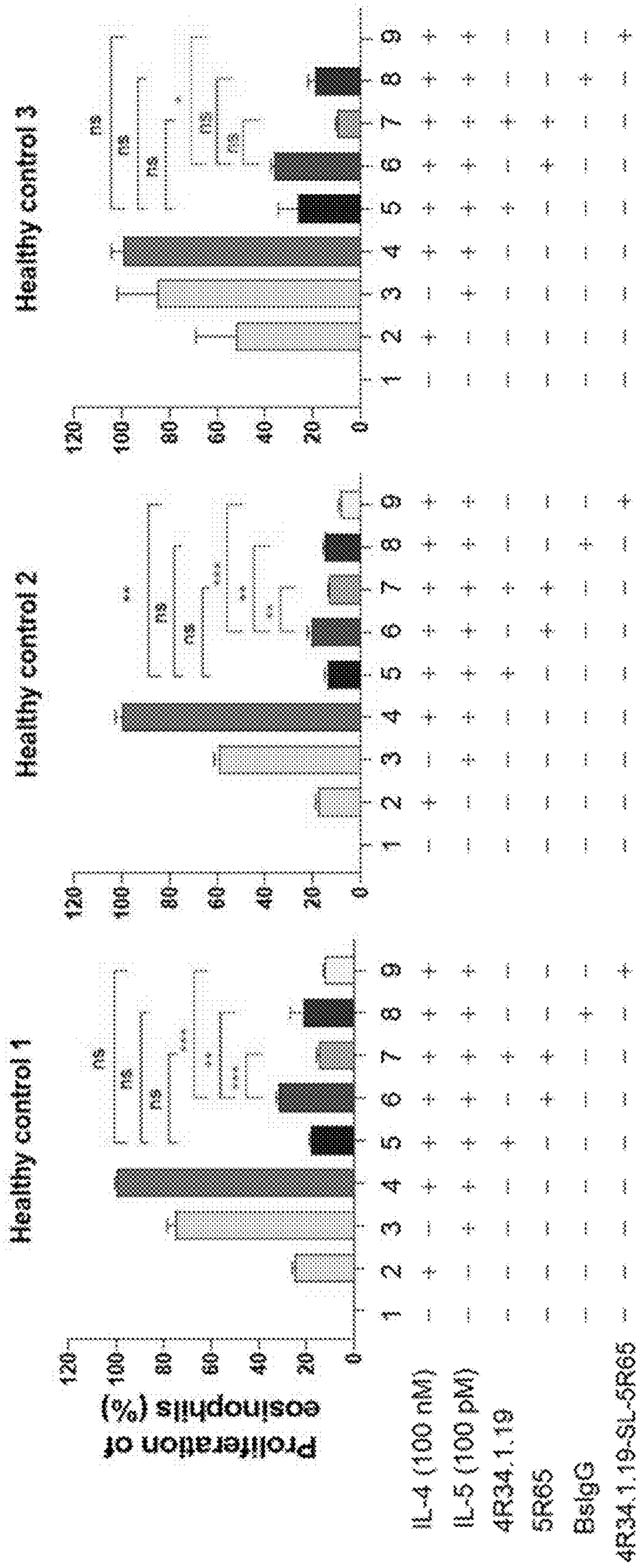
Data represent the mean ± SD. Statistical analysis was performed using a one-way ANOVA followed by the Newman-Keuls *post hoc* test. *, $P < 0.05$; , $P < 0.01$; *, $P < 0.001$; between the indicated groups; ns, not significant.

【FIG. 24】
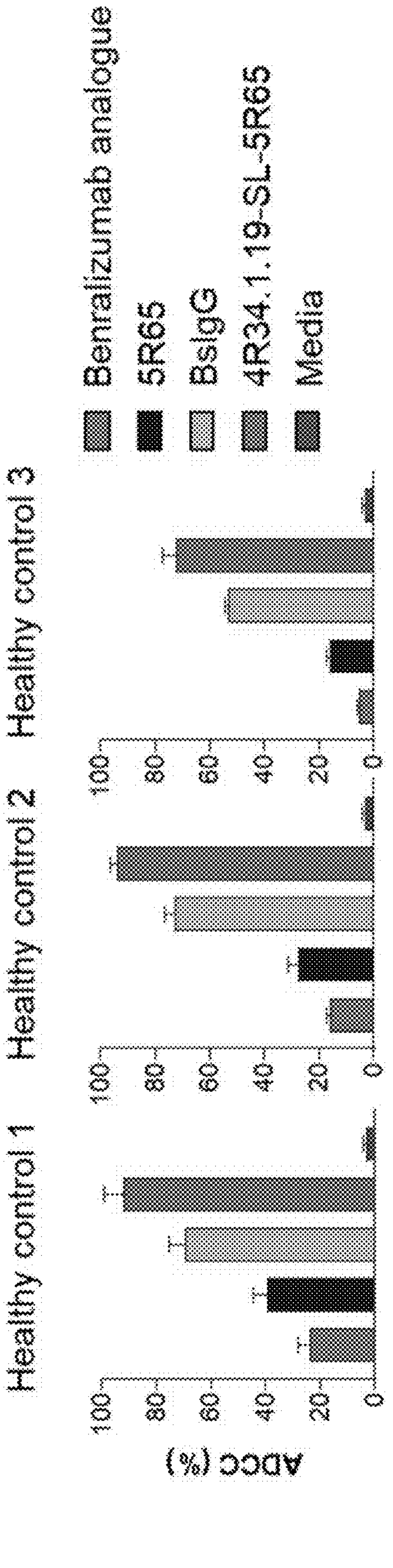

BISPECIFIC ANTIBODY SIMULTANEOUSLY BINDING TO INTERLEUKIN-4 RECEPTOR ALPHA SUBUNIT AND INTERLEUKIN-5 RECEPTOR ALPHA SUBUNIT, ENCODING NUCLEIC ACIDS THEREOF AND METHODS OF USE THEREOF FOR TREATMENT

TECHNICAL FIELD

The present invention relates to an anti-IL-4Rα/anti-IL-5Rα bispecific antibody that binds to both interleukin (IL)-4 receptor a (IL-4Rα, CD124) and IL-5 receptor a (IL-5Rα, CD125), a multispecific antibody including the bispecific antibody or an antigen-binding fragment thereof, a nucleic acid encoding the same, a vector including the nucleic acid, cells transformed with the vector, a method for producing the bispecific antibody, and the therapeutic uses thereof, for example, a composition for preventing or treating allergic diseases, inflammatory diseases, and/or diseases caused by an increase in eosinophils associated with IL-4, IL-13 and/or IL-5, and a composition for diagnosing the allergic diseases, inflammatory diseases, and/or diseases caused by an increase in eosinophils.

BACKGROUND ART

Allergic diseases such as allergic rhinitis and asthma develop when several types of cytokines stimulate immune cells [such as T-cells, B-cells, mast cells, eosinophils, basophils, and neutrophils], causing chronic inflammation. The T-cells are classified into naive T-cells that have not yet reacted with antigens, mature effector T-cells (helper T-cells, cytotoxic T-cells, and NK T-cells) that have reacted with antigens, and memory T-cells. Helper T-cells ($T_h$ cells) refer to cells that promote humoral immunity by regulating the differentiation and activation of other leukocytes among effector T cells. The $T_h$ cells are further classified into $T_h1$, $T_h2$, $T_h17$, Treg and the like, depending on the detailed functions thereof. Thereamong, $T_h2$ cells typically secrete interleukin (IL)-4, IL-5, and IL-13.

IL-4 is the only cytokine that is capable of inducing differentiation from $T_h0$ cells to $T_h2$ cells. Activated $T_h2$ cells produce additional IL-4 through autocrine, thus causing an inflammatory response due to overproduced $T_h2$. In addition, IL-4 causes B-cells to produce IgE, which is attached to the surface of mast cells and basophils to induce an inflammatory response.

IL-13, like IL-4, is a cytokine that plays an important role in IgE production and $T_h2$-mediated inflammatory responses. IL-13 and IL-4 share receptors and thus have common functions with IL-4. IL-4 is involved in the inflammatory response through a signaling mechanism mediated by receptors including Type I (IL-4 Rα, γc) and Type II (IL-4 Rα, IL-13Rα1). Meanwhile, IL-13 transmits signals through receptors including Type II (IL-4 Rα, IL-13Rα1 or IL-13Rα2). These receptors are expressed in most immune cells such as T cells, B cells, eosinophils, and mast cells. In addition, unique functions of IL-13 include goblet cell hyperplasia and smooth muscle contractility in the respiratory tract.

Dupilumab (Regeneron Pharmaceuticals Inc., U.S. Pat. No. 7,605,237, Korean Patent No. 10-1474227) targets IL-4Rα, which is commonly involved in signaling of IL-4 and IL-13, and inhibits both the cytokines. Dupilumab reduces the levels of several inflammatory proteins, for example, blocks differentiation into $T_h2$ cells, inhibits IgE production in B cells, and acts on vascular cells, thus interfering with eosinophil migration. Dupilumab was effective in patients with atopic dermatitis, asthma, eczema, and eosinophilic esophagitis (Le Floc'h et al., 2020).

IL-5 is a cytokine that mainly acts on eosinophils and is involved in overall eosinophil functions such as differentiation, proliferation, and activity of eosinophils. It is known that the receptor for IL-5 is composed of IL-5Rα and βc, IL-5Rα specifically binds to IL-5, and βc itself has no binding affinity to IL-5 and mediates signaling. Cells expressing IL-5Rα are limited to eosinophils, basophils, and mast cells. Eosinophils are implicated in various diseases, including allergic diseases, and are known to play an important role in the development of allergic diseases, including chronic bronchial asthma and atopic dermatitis. Eosinophils also induce eosinophilia, characterized by the elevated number of eosinophils in the blood of patients with these diseases. Since eosinophils are one of the essential inflammatory cells involved in allergic/inflammatory diseases, a key therapeutic strategy is to reduce the number thereof. The anti-IL-5 antibodies, namely, mepolizumab and reslizumab, is capable of indirectly reducing the number of eosinophils by inhibiting eosinophil proliferation/survival through blocking the IL-5 pathway. Benralizumab (MedImmune and AstraZeneca, U.S. Pat. No. 6,018,032, and KR Patent No. 10-0259828), which is an anti-IL-5Rα antibody that targets the IL-5Rα receptor, inhibits cell growth by directly targeting eosinophils and blocking the IL-5 pathway, and directly removes eosinophils by inducing antibody-dependent cellular cytotoxicity by natural killer cells and macrophages (Kolbeck et al., 2010).

Although eosinophils have been extensively studied as target cells to treat allergic/inflammatory diseases, the incidence of eosinophils varies from patient to patient and the symptoms thereof overlap with those caused by inflammatory responses by other immune cells. Therefore, the combination of suppressing the proliferation and activity of eosinophils by blocking the IL-5 pathway and suppressing a wider range of Th2 inflammatory responses by blocking the IL-4/IL-13 pathway can provide better therapeutic effects in a wide range of patient groups. This is because several cytokines (typically IL-4, IL-13, and IL-5) induce allergic/inflammatory responses through independent pathways. Therefore, the combination of a method of inhibiting the activity of eosinophils by targeting IL-5Rα and a method of inhibiting the activity of T-cells, B-cells, mast cells, and the like by targeting IL-4Rα are more effective in treating allergic/inflammatory disease patients having various symptoms. When cell growth is inhibited or grown cells are eliminated by targeting effector cells (e.g., eosinophils) expressing both IL-4Rα and IL-5Rα, a bispecific antibody (IL-4Rα×IL-5Rα) that binds to both IL-4Rα and IL-5Rα is effectively capable of removing the antigens by effectively inhibiting the growth of effector cells or inducing stronger ADCC by providing more labeling on both antigens expressed on the cell surface, compared to a monoclonal antibody specific to each antigen.

Under this technical background, the inventors of the present application developed a bispecific antibody that binds to both IL-4Rα and IL-5Rα, and identified that the bispecific antibody has therapeutic or prophylactic effects for allergic diseases, inflammatory diseases and/or diseases caused by an increase in eosinophils associated with IL-4, IL-13 and/or IL-5. Based thereon, the present invention was completed.

DISCLOSURE

Technical Problem

Therefore, the present invention has been made in view of the above problems, and it is one object of the present invention to provide a bispecific antibody (IL-4Rα×IL-5Rα) or antigen-binding fragment thereof that binds to both IL-4Rα and IL-5Rα.

It is another object of the present invention to provide a multispecific antibody or antigen-binding fragment thereof including the bispecific antibody binding to both IL-4Rα and IL-5Rα.

It is another object of the present invention to provide nucleic acid encoding the bispecific antibody or antigen-binding fragment thereof that binds to both IL-4Rα and IL-5Rα.

It is another object of the present invention to provide a vector containing the nucleic acid, a cell transformed with the vector, and a method for producing a bispecific antibody or antigen-binding fragment thereof that binds to both IL-4Rα and IL-5Rα.

It is another object of the present invention to provide a pharmaceutical composition for preventing or treating allergic diseases, inflammatory diseases, and/or diseases caused by an increase in eosinophils, containing the bispecific antibody or antigen-binding fragment thereof that binds to both IL-4Rα and IL-5Rα.

It is another object of the present invention to provide a composition for diagnosing allergic diseases, inflammatory diseases, and/or diseases caused by an increase in eosinophils, containing the bispecific antibody or antigen-binding fragment thereof that binds to both IL-4Rα and IL-5Rα.

Technical Solution

In accordance with one aspect of the present invention, the above and other objects can be accomplished by the provision of a bispecific antibody or antigen-binding fragment thereof including an antibody binding to interleukin (IL)-4 receptor a (IL-4Rα, CD124) represented by SEQ ID NO: 65 or an antigen-binding fragment thereof, and an antibody binding to interleukin (IL)-5 receptor a (IL-5Rα, CD125) represented by SEQ ID NO: 66 or an antigen-binding fragment thereof.

In accordance with another aspect of the present invention, provided is a multispecific antibody including the bispecific antibody or antigen-binding fragment thereof.

In accordance with another aspect of the present invention, provided is a bispecific antibody or antigen-binding fragment thereof for simultaneously inhibiting activity of IL-4, IL-13, and IL-5 that act on various effector cells (eosinophils, T-cells, B-cells, and the like) expressing either IL-4Rα or IL-5Rα and thus have independent functions.

In accordance with another aspect of the present invention, provided is a bispecific antibody or antigen-binding fragment thereof for simultaneously inhibiting activity of IL-4, IL-13, and IL-5 that act on various effector cells (eosinophils, mast cells, and the like) expressing both IL-4Rα and IL-5Rα, and thus have common functions.

In accordance with another aspect of the present invention, provided is a bispecific antibody or antigen-binding fragment thereof that exhibits better avidity effect than a monoclonal antibody for each antigen by simultaneously binding IL-4Rα and IL-5Rα to target cells expressing both IL-4Rα and IL-5Rα to provide more labeling with both antigens expressed on the cell surface.

In accordance with another aspect of the present invention, provided is a bispecific antibody or antigen-binding fragment thereof that exhibits better cell growth inhibition effect than a monoclonal antibody for each antigen by simultaneously binding IL-4Rα and IL-5Rα to target cells expressing both IL-4Rα and IL-5Rα to provide more labeling with both antigens expressed on the cell surface.

In accordance with another aspect of the present invention, provided is a bispecific antibody or antigen-binding fragment thereof that induces stronger antibody-dependent cellular cytotoxicity (ADCC) than a monoclonal antibody for each antigen by simultaneously binding IL-4Rα and IL-5Rα to target cells expressing both IL-4Rα and IL-5Rα to provide more labeling with both antigens expressed on the cell surface. In accordance with another aspect of the present invention, provided are a nucleic acid encoding the bispecific antibody or antigen-binding fragment thereof simultaneously binding to IL-4Rα and IL-5Rα and an expression vector containing the nucleic acid.

In accordance with another aspect of the present invention, provided is a cell transformed with the expression vector.

In accordance with another aspect of the present invention, provided is a method of producing a bispecific antibody or antigen-binding fragment thereof simultaneously binding to both IL-4Rα and IL-5Rα including:

(a) culturing the cells to produce a bispecific antibody or antigen-binding fragment thereof simultaneously binding to both IL-4Rα and IL-5Rα; and (b) recovering the produced antibody or antigen-binding fragment thereof.

In accordance with another aspect of the present invention, provided is a composition for preventing or treating allergic diseases, inflammatory diseases, and/or diseases caused by an increase in eosinophils including the bispecific antibody or antigen-binding fragment thereof simultaneously binding to both IL-4Rα and IL-5Rα, and a composition for diagnosing these diseases including the bispecific antibody or antigen-binding fragment thereof.

DESCRIPTION OF DRAWINGS

FIG. 1 is a schematic diagram illustrating a construction strategy of a library based on 4R34.1.19 to improve the affinity of an anti-IL-4Rα antibody, wherein the library was formed in the CDR2 portion of the heavy-chain variable region and the CDR3 portion of the light-chain variable region.

FIG. 2A shows the result of indirect ELISA to identify specific binding of anti-IL-4Rα antibodies to an sIL-4Rα (soluble IL-4Rα) antigen protein.

FIG. 2B shows binding isotherms obtained by analyzing the affinity of selected anti-IL-4Rα antibodies.

FIG. 3 shows the result of evaluation of the degree of SEAP activity by IL-4-dependent STAT6 phosphorylation using HEK-Blue-IL-4/IL-13 cells of anti-IL-4Rα antibodies with improved Affinity.

FIG. 4A shows the result of indirect ELISA to identify specific binding of anti-IL-5Rα humanized antibodies to sIL-5Rα (soluble IL-5Rα) antigen protein.

FIG. 4B shows binding isotherms obtained by analyzing the affinity of anti-IL-5Rα humanized antibodies.

FIG. 5A shows the results of evaluation of the ability of anti-IL-5Rα humanized antibodies to inhibit IL-5 dependent cell growth in TF-1/IL-5Rα cells at various antibody concentrations, compared to benralizumab analogues.

FIG. 5B shows the result of evaluation of the ability of anti-IL-5Rα humanized antibodies to inhibit eosinophil proliferation using eosinophils purified from peripheral blood of healthy donors and patients with severe asthma.

FIG. 5C shows the result of ADCC evaluation of anti-IL-5Rα humanized antibodies using eosinophils and NK cells purified from peripheral blood of healthy donors and patients with severe asthma.

FIG. 6 is a representative image of three formats used to construct the IL-4α×IL-5Rα bispecific antibody, characteristics thereof and the names of constructed clones.

FIG. 7A is a schematic diagram illustrating a bispecific antibody having an scIgG format capable of simultaneously binding IL-4α and IL-5Rα.

FIG. 7B is a schematic diagram illustrating a recombinant expression vector for expressing a scIgG-format IL-4Rα×IL-5Rα bispecific antibody, wherein Pcmv represents a promoter and the others represent domains of heavy-chains and light-chains.

FIG. 7C is a schematic diagram illustrating a bispecific antibody having a BsIgG format capable of simultaneously binding IL-4α and IL-5Rα.

FIG. 7D is a schematic diagram illustrating a recombinant expression vector for expressing a BsIgG-format IL-4Rα×IL-5Rα bispecific antibody, wherein Pcmv represents a promoter, the others represent domains of heavy-chains and light-chains, and antigen-binding sites for IL-4α and IL-5Rα and heterodimeric Fc are shown in a gray box.

FIG. 8A shows the result of SDS-PAGE analysis to identify an IL-4Rα×IL-5Rα bispecific antibody having a scIgG format.

FIG. 8B shows the result of size exclusion chromatography (SEC) analysis to identify the scIgG-format IL-4Rα×IL-5Rα bispecific antibody.

FIG. 8C shows the result of SDS-PAGE analysis to identify the BsIgG-format IL-4Rα×IL-5Rα bispecific antibody.

FIG. 8D shows the result of SEC analysis to identify an IL-4Rα×IL-5Rα bispecific antibody having a BsIgG format.

FIG. 9A is a schematic diagram illustrating a bispecific antibody having an IgG-scFv (specifically, 4R-IgG-5R-$_{HL}$scFv) format capable of simultaneously binding to IL-4α and IL-5Rα.

FIG. 9B is a schematic diagram illustrating a recombinant expression vector for expressing the 4R-IgG-5R-$_{HL}$scFv format IL-4Rα×IL-5Rα bispecific antibody, wherein Pcmv represents a promoter and the others represent domains of heavy-chains and light-chains.

FIG. 9C is a schematic diagram illustrating a bispecific antibody having an G (specifically, 4R-IgG-5R-$_{LH}$scFv) format capable of simultaneously binding to IL-4α and IL-5Rα.

FIG. 9D is a schematic diagram illustrating a recombinant expression vector for expressing the 4R-IgG-5R-$_{LH}$scFv format IL-4Rα×IL-5Rα bispecific antibody, wherein Pcmv represents a promoter, the others represent domains of heavy and light-chains, and antigen-binding sites for IL-4α and IL-5Rα and wild-type Fc are shown in the gray box.

FIG. 10A shows the result of SDS-PAGE analysis to identify an IL-4Rα×IL-5Rα bispecific antibody having a 4R-IgG-5R-$_{HL}$scFv format.

FIG. 10B shows the result of SEC analysis to identify the 4R-IgG-5R-$_{HL}$scFv-format bispecific antibody.

FIG. 10C shows the result of SDS-PAGE analysis to identify an IL-4Rα×IL-5Rα bispecific antibody having a 4R-IgG-5R-$_{LH}$scFv format.

FIG. 10D shows the result of SEC analysis to identify the 4R-IgG-5R-$_{HL}$scFv-format bispecific antibody.

FIG. 11A is a schematic diagram illustrating a bispecific antibody having an G (specifically, 5R-IgG-5R-$_{HL}$scFv) format capable of simultaneously binding to IL-4α and IL-5Rα.

FIG. 11B is a schematic diagram illustrating a recombinant expression vector for expressing the 5R-IgG-5R-$_{HL}$scFv format IL-4Rα×IL-5Rα bispecific antibody, wherein Pcmv represents a promoter, and the others represent domains of heavy and light-chains.

FIG. 11C is a schematic diagram illustrating a bispecific antibody having an IgG-scFv (specifically 5R-IgG-5R-$_{LH}$-scFv) format capable of simultaneously binding to IL-4α and IL-5Rα.

FIG. 11D is a schematic diagram illustrating a recombinant expression vector for expressing the 5R-IgG-5R-$_{LH}$-scFv format IL-4Rα×IL-5Rα bispecific antibody, wherein Pcmv represents a promoter, the others represent domains of heavy and light-chains, and antigen-binding sites for IL-4α and IL-5Rα and wild-type Fc are shown in the gray box.

FIG. 12A shows the result of SDS-PAGE analysis to identify an IL-4Rα×IL-5Rα bispecific antibody having a 5R-IgG-5R-$_{HL}$scFv format.

FIG. 12B shows the result of SEC analysis to identify the 5R-IgG-5R-$_{HL}$scFv-format IL-4Rα×IL-5Rα bispecific antibody.

FIG. 12C shows the result of SDS-PAGE analysis to identify an IL-4Rα×IL-5Rα bispecific antibody having a 5R-IgG 5R-$_{LH}$scFv format.

FIG. 12D shows the result of SEC analysis to identify the 5R-IgG-5R-$_{LH}$scFv-format IL-4Rα×IL-5Rα bispecific antibody.

FIG. 13 shows the result of SDS-PAGE analysis of the 5R-IgG-4R-$_{LH}$scFv-format IL-4Rα×IL-5Rα bispecific antibody depending on the antibody sequence.

FIG. 14 shows the result of SEC analysis of the 5R-IgG-4R-$_{LH}$scFv-format IL-4Rα×IL-5Rα bispecific antibody depending on the antibody sequence.

FIG. 15A is a schematic diagram illustrating a bispecific antibody having a 4R-LL-5R format capable of simultaneously binding to IL-4α and IL-5Rα.

FIG. 15B is a schematic diagram illustrating a recombinant expression vector for expressing the 4R-LL-5R format IL-4Rα×IL-5Rα bispecific antibody, wherein Pcmv represents a promoter, and the others represent domains of heavy-chains and light-chains.

FIG. 15C is a schematic diagram illustrating a bispecific antibody having a 4R-SL-5R format capable of simultaneously binding to IL-4α and IL-5Rα.

FIG. 15D is a schematic diagram illustrating a recombinant expression vector for expressing the 4R-SL-5R-format IL-4Rα×IL-5Rα bispecific antibody, wherein Pcmv represents a promoter, the others represent domains of heavy-chains and light-chains, and antigen-binding sites for IL-4α and IL-5Rα and wild-type Fc are shown in the gray box.

FIG. 16A shows the result of SEC analysis to identify an IL-4Rα×IL-5Rα bispecific antibody having a 4R-LL-5R format.

FIG. 16B shows the result of SDS-PAGE analysis to identify an IL-4Rα×IL-5Rα bispecific antibody having a 4R-SL-5R format.

FIG. 16C shows the result of SEC analysis to identify an IL-4Rα×IL-5Rα bispecific antibody having a 4R-SL-5R format.

FIG. 17A is a schematic diagram illustrating a bispecific antibody having a 5R-LL-4R format capable of simultaneously binding to IL-4α and IL-5Rα.

FIG. 17B is a schematic diagram illustrating a recombinant expression vector for expressing the 5R-LL-4R-format IL-4Rα×IL-5Rα bispecific antibody, wherein Pcmv represents a promoter, and the others represent domains of heavy-chains and light-chains.

FIG. 17C is a schematic diagram illustrating a bispecific antibody having a 5R-SL-4R format capable of simultaneously binding to IL-4α and IL-5Rα.

FIG. 17D is a schematic diagram illustrating a recombinant expression vector for expressing the 5R-LL-4R-format IL-4Rα×IL-5Rα bispecific antibody, wherein Pcmv represents a promoter, the others represent domains of heavy and light-chains, and antigen-binding sites for IL-4α and IL-5Rα and wild-type Fc are shown in the gray box.

FIG. 18A shows the result of SEC analysis to identify the 5R-LL-4R-format IL-4Rα×IL-5Rα bispecific antibody.

FIG. 18B shows the result of SEC analysis to identify the 5R-SL-4R-format IL-4Rα×IL-5Rα bispecific antibody.

FIG. 19 shows the result of SDS-PAGE analysis of the 4R-SL-5R-format IL-4Rα×IL-5Rα bispecific antibody depending on the antibody sequence.

FIG. 20 shows the result of SEC analysis of the 4R-SL-5R-format IL-4Rα×IL-5Rα bispecific antibody depending on the antibody sequence.

FIG. 21 shows sIL-4α and sIL-5Rα antigen-binding ability of anti-IL-4α antibody, anti-IL-5Rα antibody, and bispecific antibodies of three different format types (BsIgG, 5R-IgG-4R-$_{LH}$scFv, and 4R-SL-5R), evaluated by indirect ELISA.

FIG. 22 shows the expression levels of IL-4α and IL-5Rα in eosinophils obtained by analyzing granulocyte layers (neutrophils+eosinophils) isolated from peripheral blood of healthy controls using a flow cytometer.

FIG. 23 shows the evaluation of ability of monoclonal antibodies (4R34.1.19/5R65) and two bispecific antibodies to inhibit eosinophil proliferation by IL-4 and IL-5 using eosinophils purified from peripheral blood of healthy donors.

FIG. 24 shows the evaluation of antibody-dependent cellular toxicity (ADCC) of monoclonal antibodies (benralizumab analogue/5R65) and two bispecific antibodies using eosinophils and NK-cells purified from peripheral blood of healthy donors.

BEST MODE

Unless defined otherwise, all technical and scientific terms used herein have the same meanings as appreciated by those skilled in the field to which the present invention pertains. In general, the nomenclature used herein is well-known in the art and is ordinarily used.

According to the present invention, a novel anti-IL-5Rα humanized antibody was developed by performing mouse immunization and humanization.

In an embodiment of the present invention, a novel bispecific antibody or antigen-binding fragment thereof that induces antibody-dependent cytotoxicity (ADCC) more strongly in target cells (cells expressing IL-4Rα and IL-5Rα) than a monoclonal antibody (anti-IL-4Rα antibody and anti-IL-5Rα antibody) was identified.

Based thereon, in one aspect, the present invention is directed to a bispecific antibody (IL-4Rα×IL-5Rα) or antigen-binding fragment thereof including an antibody binding to interleukin (IL)-4 receptor a (IL-4Rα, CD124) represented by SEQ ID NO: 65 or an antigen-binding fragment thereof, and an antibody binding to interleukin (IL)-5 receptor a (IL-5Rα, CD125) represented by SEQ ID NO: 66 or an antigen-binding fragment thereof.

In the present invention, various formats of IL-4Rα×IL-5Rα bispecific antibodies capable of simultaneously binding to two or more antigenic proteins were constructed and expressed.

As used herein, the term "bispecific antibody" refers to a protein capable of binding to two different types of antigens (target proteins). Specifically, the bispecific antibody does not exist naturally and is preferably prepared by genetic engineering or any method.

The bispecific antibody or antigen-binding fragment thereof can bind to both IL-4Rα expressed in T-cells, B-cells, endothelial cells, and the like, and IL-5Rα expressed in eosinophils, basophils, and mast cells. The term "bispecific antibody" of the present invention may be used interchangeably with "bitarget antibody", "biantibody" or "biantibody protein". Preferably, the antigens to the bispecific antibody of the present invention may be IL-4Rα and IL-5Rα. The form of the bispecific antibody of the present invention is not particularly limited thereto and is constructed based on an IgG form.

The bispecific antibody refers to a molecule that has an antigen-binding site linking directly or via a linker or forms a heterodimer through electrostatic interaction.

The term "valent" means the presence of a specified number of binding sites specific to an antigen in the molecule. As such, the terms "monovalent", "bivalent", "tetravalent", and "hexavalent" refer to the presence of each of 1, 2, 4, and 6 binding sites specific for an antigen in a molecule.

The term "bispecific anti-IL-4α/IL-5α antibody" refers to a bispecific antibody having a domain that specifically binds to IL-4α and a domain that specifically binds to IL-5α. The domains that specifically bind to IL-4α and IL-5α are typically VH/VL pairs and the monovalence or the bivalence of bispecific anti-IL-4α/IL-5α antibodies is determined depending on the VH/VL pair binding to IL-4α and IL-5α.

In another aspect, the present invention is directed to a multispecific antibody including the bispecific antibody or antigen-binding fragment thereof.

The term "multispecific antibody" refers to an antibody that has binding specificity for at least three different antigens. The multispecific antibody includes a tri- or higher antibody, for example, a trispecific antibody, a tetraspecific antibody, or an antibody that targets more targets.

As used herein, the term "antibody" refers to a protein molecule that includes an immunoglobulin molecule that is immunologically reactive with a specific antigen and serves as a receptor that specifically recognizes the antigen, and includes multispecific antibodies, monoclonal antibodies, whole antibodies and antibody fragments. The antibody also includes antibodies produced by genetic engineering, such as chimeric antibodies (e.g., humanized murine antibodies) and heterologous antibodies (e.g., bispecific antibodies). The whole antibody has a structure having two full-length light-chains and two full-length heavy-chains, and each light-chain is bonded to the heavy-chain by a disulfide bond. The whole antibody includes IgA, IgD, IgE, IgM, and IgG, and IgG may include IgG1, IgG2, IgG3, and IgG4 subtypes. In addition, the antibody may include monovalent, bivalent, diabody, tribody and tetrabody antibodies.

The antibody includes immunoglobulin molecules, including multispecific antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

In the present invention, the bispecific antibody or antigen-binding fragment thereof is an antibody that specifically binds to IL-4Rα in the form of immunoglobulin (IgG) and a whole antibody that specifically binds to IL-5Rα, or Fab', F(Ab')2, Fab, Fv, rIgG, or single chain Fv (scFv) proteins linked via a linker, or may be an IgG-type antibody using heterodimeric Fc-based technology ((Choi et al., 2013); KR Patent No. 10-1522954).

Specifically, the IL-4Rα×IL-5Rα bispecific antibody or antigen-binding fragment thereof according to the present invention includes: an IL-4Rα×IL-5Rα bispecific antibody having an scIgG or BsIgG format in which a heavy-chain variable region and a light-chain variable region of the antibody binding to IL-4Rα or the antibody binding to IL-5Rα are linked to the heterodimeric Fc;

- an IL-4Rα×IL-5Rα bispecific antibody having an IgG-scFv format in which scFv including the heavy-chain variable region and the light-chain variable region of the antibody binding to IL-4Rα or the antibody binding to IL-5Rα is linked to the C-terminus of the IgG including the heavy-chain variable region and the light-chain variable region of the antibody binding to IL-4Rα or the antibody binding to IL-5Rα; or
- an IL-4Rα×IL-5Rα bispecific antibody having a DVD (dual variable domain) IgG format including a format in which heavy-chain and light-chain variable regions of the antibody binding to IL-4Rα or the antibody binding to IL-5Rα are juxtaposed at the N-terminus of the IgG including the heavy-chain variable region and the light-chain variable region of the antibody binding to IL-4Rα or the antibody binding to IL-5Rα.

The whole (complete) antibody has a structure having two full-length light-chains and two full-length heavy-chains, wherein each light-chain is linked to a corresponding heavy-chain by a disulfide bond.

As used herein, the term "heavy-chain" encompasses both a full-length heavy-chain, which includes a variable domain (VH) containing an amino acid sequence having a sufficient variable region sequence for imparting specificity to an antigen and three constant domains (CH1, CH2 and CH3), and a fragment thereof. As used herein, the term "light-chain" encompasses both a full-length light-chain, which includes a variable domain (VL) containing an amino acid sequence having a sufficient variable region sequence for imparting specificity to an antigen and a constant domain (CL), and a fragment thereof.

The whole antibody includes subtypes of IgA, IgD, IgE, IgM and IgG, and in particular, IgG includes IgG1, IgG2, IgG3 and IgG4. The heavy-chain constant region has gamma (γ), mu (p), alpha (α), delta (δ) and epsilon (ε) types, and is subclassified into gamma 1 (γ1), gamma 2 (γ2), gamma 3 (γ3), gamma 4 (γ4), alpha 1 (α1), and alpha 2 (α2). The light-chain constant region has kappa (κ) and lambda (λ) types.

The antigen-binding fragment of an antibody or antibody fragment refers to a fragment that has antigen-binding function and includes Fab, F(ab'), F(ab')2, Fv and the like. Among the antibody fragments, Fab refers to a structure including a variable region of each of the heavy-chain and the light-chain, the constant region of the light-chain, and the first constant domain (CH1) of the heavy-chain, each having one antigen-binding site. Fab' is different from Fab in that it further includes a hinge region including at least one cysteine residue at the C-terminus of the CH1 domain of the heavy-chain. F(ab')2 is created by a disulfide bond between cysteine residues in the hinge region of Fab'.

Fv is the minimal antibody fragment having only a heavy-chain variable region and a light-chain variable region. Two-chain Fv is a fragment in which the variable region of the heavy-chain and the variable region of the light-chain are linked by a non-covalent bond, and single-chain Fv (scFv) is a fragment in which the variable region of the heavy-chain and the variable region of the light-chain are generally linked by a covalent bond via a peptide linker therebetween, or are directly linked at the C-terminal, forming a dimer-shaped structure, like the two-chain Fv. Such antibody fragments may be obtained using proteases (e.g., Fab can be obtained by restriction-cleaving the complete antibody with papain, and the F(ab')2 fragment can be obtained by restriction-cleaving the complete antibody with pepsin), and may be produced using genetic recombination techniques.

The "single chain Fv" or "scFv" antibody fragment includes VH and VL domains of the antibody, wherein these domains are present in a single polypeptide chain. The Fv polypeptide may further include a polypeptide linker between the VH domain and the VL domain in order for the scFv to form a target structure for antigen binding.

A "Fab" fragment contains the variable and constant domains of the light-chain, and a variable and first constant domain (CH1) of the heavy-chain. A F(ab')2 antibody fragment generally includes a pair of Fab fragments covalently linked via a hinge cysteine located therebetween near the carboxyl end thereof.

In an embodiment, the antibody according to the present invention includes, but is not limited to, monoclonal antibodies, multispecific antibodies, human antibodies, humanized antibodies, chimeric antibodies, scFVs, Fab fragments, F(ab') fragments, disulfide-bond Fvs (sdFVs), anti-idiotypic (anti-Id) antibodies, epitope-binding fragments of such antibodies, and the like.

The heavy-chain constant region may be selected from gamma (γ), mu (u), alpha (α), delta (δ) and epsilon (c) isotypes. For example, the constant region may be gamma 1 (IgG1), gamma 3 (IgG3), or gamma 4 (IgG4). The light-chain constant region may be kappa or lambda.

The term "monoclonal antibody" refers to an identical antibody, which is obtained from a population of substantially homogeneous antibodies, that is, each antibody constituting the population, excluding possible naturally occurring mutations that may be present in trivial amounts. Monoclonal antibodies are highly specific and are thus induced against a single antigenic site. Unlike conventional (polyclonal) antibody preparations that typically include different antibodies directed against different determinants (epitopes), each monoclonal antibody is directed against a single determinant on the antigen.

For example, monoclonal antibodies useful in the present invention may be produced by hybridoma methods, or may be produced in bacterial, eukaryotic or plant cells using recombinant DNA methods. In addition, monoclonal antibodies may be isolated from phage antibody libraries.

The term "epitope" refers to a protein determinant to which an antibody can specifically bind. Epitopes usually consist of a group of chemically active surface molecules, such as amino acid or sugar side chains, and generally have not only specific three-dimensional structural characteristics but also specific charge characteristics. Three-dimensional epitopes are distinguished from non-three-dimensional epitopes in that a bond to the former is broken in the presence of a denatured solvent, while a bond to the latter is not broken.

IL-4Rα has been reported to be expressed in various types of effector cells such as T-cells, B-cells, mast cells, eosinophils, and endothelial cells. On the other hand, IL-5Rα has been reported to be restrictedly expressed only in eosinophils, basophils, and mast cells. Therefore, bispecific antibodies that bind to IL-4Rα and IL-5Rα can not only bind to and act on various effector cells expressing IL-4Rα or IL-5Rα, but also can specifically bind with stronger avidity to eosinophils, basophils, and mast cells in which both the antigens are expressed.

Active actions such as differentiation, growth, migration, and secretion of toxic proteins of effector cells that exhibit inflammatory responses such as T-cells, B-cells, eosinophils, basophils, and mast cells are induced by cytokines. These cytokines have common functions or their own unique functions to induce an inflammatory response. Thus, although the action of one cytokine is inhibited, another cytokine can activate effector cells. Bispecific antibodies that bind to IL-4Rα and IL-5Rα can simultaneously block multiple pathways that cause inflammatory responses by simultaneously inhibiting Th2 cytokines (IL-4, IL-5, and IL-13).

For example, an FDA-approved antibody, dupilumab, is used to treat diseases such as atopy and asthma. However, the number of eosinophils in the peripheral blood of patients to which dupilumab is administered was increased. This is because dupilumab acts on endothelial cells to inhibit the migration of eosinophils. The bispecific antibody that binds to IL-5Rα and IL-4Rα exhibits better therapeutic effect for a wide range of patient groups by the combination of a method of blocking the IL-5 pathway to inhibit the proliferation and activity of eosinophils and a method of blocking the IL-4/IL-13 pathway to inhibit a wider range of the Th2 inflammatory response. In addition, bispecific antibodies that bind to IL-4Rα and IL-5Rα can induce stronger antibody-dependent cytotoxicity in eosinophils, basophils, and mast cells in which both antigens (IL-4Rα and IL-5Rα) are expressed.

The numbering of amino acid residues in antibodies throughout this specification is determined in accordance with Kabat numbering and EU index as disclosed in the document [Kabat et al., Sequences of Proteins of Immunological Interest, 5th Ed. Public Health Service, National Institutes of Health, Bethesda, MD. (1991)], unless explicitly stated otherwise.

In the present invention, the antibody that binds to IL-4Rα and the antibody that binds to IL-5Rα have binding ability to IL-4Rα of SEQ ID NO: 65 and IL-5Rα of SEQ ID NO: 66.

```
                                                      SEQ ID No: 65
1               5                   10                  15                  20
Met Lys Val Leu Gln Glu Pro Thr Cys Val Ser Asp Tyr Ile Ser Ile Ser Thr Cys Glu

21              25                  30                  35                  40
Trp Lys Met Asn Gly Pro Thr Asn Cys Ser Thr Glu Leu Arg Leu Leu Tyr Gln Leu Val

41              45                  50                  55                  60
Phe Leu Leu Ser Glu Ala His Thr Cys Ile Pro Glu Asn Asn Gly Gly Ala Gly Cys Val

61              65                  70                  75                  80
Cys His Leu Leu Ile Asp Asp Val Val Ser Ala Asp Asn Tyr Thr Leu Asp Leu Trp Ala

81              85                  90                  95                  100
Gly Gln Gln Leu Leu Trp Lys Gly Ser Phe Lys Pro Ser Glu His Val Lys Pro Arg Ala

101             105                 110                 115                 120
Pro Gly Asn Leu Thr Val His Thr Asn Val Ser Asp Thr Leu Leu Leu Thr Trp Ser Asn

121             125                 130                 135                 140
Pro Tyr Pro Pro Asp Asn Tyr Leu Tyr Asn His Leu Thr Tyr Ala Val Asn Ile Trp Ser

141             145                 150                 155                 160
Glu Asn Asp Pro Ala Asp Phe Arg Ile Tyr Asn Val Thr Tyr Leu Glu Pro Ser Leu Arg

161             165                 170                 175                 180
Ile Ala Ala Ser Thr Leu Lys Ser Gly Ile Ser Tyr Arg Ala Arg Val Arg Ala Trp Ala

181             185                 190                 195                 200
Gln Cys Tyr Asn Thr Thr Trp Ser Glu Trp Ser Pro Ser Thr Lys Trp His Asn Ser Tyr

201             205     207
Arg Glu Pro Phe Glu Gln His
```

SEQ ID No: 66

```
1               5                   10                  15                  20
Asp Leu Leu Pro Asp Glu Lys Ile Ser Leu Leu Pro Pro Val Asn Phe Thr Ile Lys Val

21              25                  30                  35                  40
Thr Gly Leu Ala Gln Val Leu Leu Gln Trp Lys Pro Asn Pro Asp Gln Glu Gln Arg Asn

41              45                  50                  55                  60
Val Asn Leu Glu Tyr Gln Val Lys Ile Asn Ala Pro Lys Gu Asp Asp Tyr Glst Thr Arg

61              65                  70                  75                  80
Ile Thr Glu Ser Lys Cys Val Thr Ile Leu His Lys Gly Phe Ser Ala Ser Val Arg Thr

81              85                  90                  95                  100
Ile Leu Gln Asn Asp His Ser Leu Leu Ala Ser Ser Trp Ala Ser Ala Glu Leu His Ala

101             105                 110                 115                 120
Pro Pro Gly Ser Pro Gly Thr Ser Ile Val Asn Leu Thr Cys Thr Thr Asn Thr Thr Glu

121             125                 130                 135                 140
Asp Asn Tyr Ser Arg Leu Atp Ser Tyr Gln Val Ser Leu His Cys Thr Trp Leu Val Gly

141             145                 150                 155                 160
Thr Asp Ala Pro Glu Asp Thr Gln Tyr Phe Leu Tyr Tyr Arg Tyr Gly Ser Trp Thr Glu

161             165                 170                 175                 180
Glu Cys Gln Glu Tyr Ser Lys Asp Thr Leu Gly Arg Asn lle Ala Cys Trp Phe Pro Arg

181             185                 190                 195                 200
Thr Phe Ile Leu Ser Lys Gly Arg Asp Trp Leu Ala Val Leu Val Asn Gly Ser Ser Lys

201             205                 210                 215                 220
His Ser Ala Ile Arg Pro Pha Asp Gln Leu Phe Ala Leu His Ata Ile Asp Gln Ile Asn

221             225                 230                 235                 240
Pro Pro Leu Asn Val Thr Ala Glu Ile Glu Gly Thr Arg Lev Ser Ile Gln Trp Glu Lys

241             245                 250                 255                 260
Pro Val Ser Ala Phe Fro Ile His Cys Phe Asp Tyr Glu Val Lys Ile His Asn Thr Arg

261             265                 270                 275                 280
Asn Gly Tyr Leu Gln Ile Glu Lys Lys Met Try Asn Ala Phe Ile Ser Ile Ile Asp Asp

281             285                 290                 295                 300
Leu Ser Lys Tyr Asp Val Gln Val Arg Ala Ala Val Ser Ser Met Cys Arg Glu Ala Gly

301             305                 310                 315                 320
Leu Tre Ser Glu Trp Ser Gln Pro Ile Tyr Val Gly Asn Asp Glu His Lys Pro Leu Arg

    322
Glu Trp
```

The term "affinity" refers to the ability to specifically recognize a specific site of an antigen and to bind thereto, and specificity and high-affinity of an antibody for an antigen are important factors in the immune response. The affinity constant ($K_D$) can be determined using surface plasmon resonance (SPR), for example, a BIAcore system. An affinity constant ($K_D$) calculated from a 1:1 Langmuir binding model (simultaneously $k_{on}$ and $k_{off}$) and the ratio of the rate constant $k_{off}/k_{on}$ was obtained based on surface plasmon resonance data.

The binding affinity of the bispecific antibody according to the present invention ranges from $10^{-5}$ M to $10^{-12}$ M. For example, the binding affinity is $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-5}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-5}$ M to $10^{-9}$ M, $10^{-6}$ M to $10^{-9}$ M, $10^{-7}$ M to $10^{-9}$ M, $10^{-8}$ M to $10^{-9}$ M, $10^{-5}$ M to $10^{-8}$ M, $10^{-6}$ M to $10^{-8}$ M, $10^{-7}$ M to $10^{-8}$ M, $10^{-5}$ M to $10^{-7}$ M, $10^{-6}$ M to $10^{-7}$ M or $10^{-5}$ M to $10^{-6}$ M.

In one embodiment of the present invention, a library may be constructed to improve the affinity of the CDR region of an antibody that specifically binds to sIL-4α or sIL-5Rα and may be realized by a method including (1) selecting an amino acid site having a high possibility of binding to sIL-4α or sIL-5Rα, among six complementary binding sites (CDRs) involved in antigen-binding of light-chain variable regions (VL) and heavy-chain variable regions (VH) as library templates, (2) designing a degenerated codon primer and a spiked oligonucleotide capable of encoding an amino acid to be included in the library at the selected amino acid site, and (3) expressing the designed heavy-chain and light-chain variable region libraries in the form of scFab or Fab using a yeast surface expression system.

In one embodiment of the present invention, screening may be performed using the library to isolate the antibody scFab that specifically binds to sIL-4α or sIL-5Rα and/or to improve affinity thereof.

The method for screening the antibody that specifically binds to sIL-4α or sIL-5Rα according to the present invention may be carried out by a method including:

(1) expressing an antibody scFab library capable of binding to sIL-4α or sIL-5Rα using a yeast surface expression system;

(2) constructing a vector expressing sIL-4α or sIL-5Rα and being fused with a Hit Tag, followed by expression;

(3) binding sIL-4α or sIL-5Rα to the library and selecting the yeast maintaining to bind to sIL-4α or sIL-5Rα even after the conditions for dissociating the bound sIL-4α or sIL-5Rα are satisfied (Kinetic screening); and (4) measuring the affinity of the binding between sIL-4α or sIL-5Rα and the library.

As described above, the anti-IL-4α or anti-IL-5Rα antibody according to the present invention is an antibody binding with high affinity to hIL-4Rα, which is obtained by selecting antibodies to sIL-4α or sIL-5Rα from the human antibody scFab library expressed on the yeast cell surface, additionally constructing an antibody Fab library on the yeast surface to improve affinity, and selecting an antibody binding with high affinity to sIL-4α or sIL-5Rα through kinetic screening.

Techniques for identifying and separating high-affinity antibodies from libraries are important for the separation of new therapeutic antibodies. The separation of high-affinity antibodies from libraries may depend on the size of the libraries, the production efficiency in bacterial cells, and the variety of libraries. The size of the libraries is reduced by improper folding of the antibody- or antigen-binding protein and inefficient production due to the presence of the stop codon. Expression in bacterial cells can be inhibited when the antibody- or antigen-binding domain is not properly folded. Expression can be improved by alternately mutating residues on the surface of the variable/constant interfaces or the selected CDR residues.

It is important to generate various libraries of antibody- or antigen-binding proteins in the separation of high-affinity antibodies. CDR3 regions have often been found to participate in antigen binding. Since the CDR3 region on the heavy-chain varies considerably in terms of size, sequence and structurally dimensional morphology, various libraries can be prepared using the same.

Also, diversity can be created by randomizing the CDR regions of variable heavy- and light-chains using all 20 amino acids at each position. The use of all 20 amino acids results in antibody sequences having increased diversity and an increased chance of identifying new antibodies.

The term "substituting", "substituted", "mutating" or "mutated" refers to the alteration, deletion, or insertion of one or more amino acids or nucleotides into a polypeptide or polynucleotide sequence to create a variant of the sequence.

The non-human (e.g., murine) antibody of the "humanized" form is a chimeric antibody containing a minimal sequence derived from non-human immunoglobulin. In most cases, the humanized antibody is a human immunoglobulin (receptor antibody) in which a residue from the hypervariable region of a receptor is replaced with a residue from the hypervariable region of a non-human species (donor antibody) such as a mouse, rat, rabbit or non-human primate having the desired specificity, affinity and ability.

The term "human antibody" means a molecule derived from human immunoglobulin, wherein the entire amino acid sequence constituting the antibody including a complementarity-determining region and a structural region are composed of human immunoglobulin.

A part of the heavy-chain and/or light-chain is identical to or homologous with the corresponding sequence in an antibody derived from a particular species or belonging to a particular antibody class or subclass, while the other chain(s) include "chimeric" antibodies (immunoglobulins) which are identical to or homologous with corresponding sequences in an antibody derived from another species or belonging to another antibody class or subclass, as well as fragments of such antibody exhibiting the desired biological activity.

As used herein, the term "antibody variable region" refers to the light- and heavy-chain regions of an antibody molecule including the amino acid sequences of a complementarity-determining region (CDR; i.e., CDR1, CDR2, and CDR3) and a framework region (FR). VH refers to a variable domain of the heavy-chain. VL refers to a variable domain of the light-chain.

The term "complementarity-determining region" (CDR; i.e., CDR1, CDR2, and CDR3) refers to an amino acid residue of the antibody variable domain that is necessary for antigen binding. Each variable domain typically has three CDR regions, identified as CDR1, CDR2, and CDR3.

In the present invention, the antibody or antigen-binding fragment thereof binding to IL-4Rα may include a heavy-chain CDR1 of SEQ ID NO: 1, at least one heavy-chain CDR2 selected from SEQ ID NOS: 2 to 7, and a heavy-chain CDR3 of SEQ ID NO: 8, and a light-chain CDR1 of SEQ ID NO: 13, a light-chain CDR2 of SEQ ID NO: 14, and a light-chain CDR3 selected from the group consisting of SEQ ID NOS: 15 to 20.

Specifically, the antibody or antigen-binding fragment thereof binding to IL-4Rα may include a heavy-chain CDR1 of SEQ ID NO: 1, a heavy-chain CDR2 of SEQ ID NO: 2, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 15;

a heavy-chain CDR1 of SEQ ID NO: 1, a heavy-chain CDR2 of SEQ ID NO: 3, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 16;

a heavy-chain CDR1 of SEQ ID NO: 1, a heavy-chain CDR2 of SEQ ID NO: 4, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 17;

a heavy-chain CDR1 of SEQ ID NO: 1, a heavy-chain CDR2 of SEQ ID NO: 5, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 16;

a heavy-chain CDR1 of SEQ ID NO: 1, a heavy-chain CDR2 of SEQ ID NO: 6, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 17;

a heavy-chain CDR1 of SEQ ID NO: 1, a heavy-chain CDR2 of SEQ ID NO: 7, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 16;

a heavy-chain CDR1 of SEQ ID NO: 1, a heavy-chain CDR2 of SEQ ID NO: 5, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 18;

a heavy-chain CDR1 of SEQ ID NO: 1, a heavy-chain CDR2 of SEQ ID NO: 3, and a heavy-chain CDR3 of SEQ ID NO: 8, and a light-chain CDR1 of SEQ ID NO: 13, a light-chain CDR2 of SEQ ID NO: 14, and a light-chain CDR3 of SEQ ID NO: 19; or a heavy-chain CDR1 of SEQ ID NO: 1, a heavy-chain CDR2 of SEQ ID NO: 5, and a heavy-chain CDR3 of SEQ ID NO: 8, and a light-chain CDR1 of SEQ ID NO:

13, a light-chain CDR2 of SEQ ID NO: 14, and a light-chain CDR3 of SEQ ID NO: 20.

Specifically, the antibody or antigen-binding fragment thereof binding to IL-IL-4Rα may include the heavy-chain and light-chain CDR sequences shown in Table 1 and/or Table 3 below.

The antibody or antigen-binding fragment thereof binding to IL-5Rα may recognize, as epitopes, one or more amino acid residues selected from the group consisting of amino acid residues 221 to 322 corresponding to domain 3 (D3) of the sequence of IL-5Rα represented by SEQ ID NO: 66.

The antibody or antigen-binding fragment thereof that binds to IL-5Rα may include a heavy-chain CDR1 of SEQ ID NO: 27, a heavy-chain CDR2 of SEQ ID NO: 28, at least one heavy-chain CDR3 selected from the group consisting of SEQ ID NOS: 29 to 35, and a light-chain CDR1 of SEQ ID NO: 43, a light-chain CDR2 of SEQ ID NO: 44, and a light-chain CDR3 of SEQ ID NO: 45.

Specifically, the antibody or antigen-binding fragment thereof that binds to IL-5Rα may include a heavy-chain CDR1 of SEQ ID NO: 27, a heavy-chain CDR2 of SEQ ID NO: 28, a heavy-chain CDR3 of SEQ ID NO: 29, and a light-chain CDR1 of SEQ ID NO: 43, a light-chain CDR2 of SEQ ID NO: 44, and a light-chain CDR3 of SEQ ID NO: 45;

- a heavy-chain CDR1 of SEQ ID NO: 27, a heavy-chain CDR2 of SEQ ID NO: 28, a heavy-chain CDR3 of SEQ ID NO: 30, and a light-chain CDR1 of SEQ ID NO: 43, a light-chain CDR2 of SEQ ID NO: 44, and a light-chain CDR3 of SEQ ID NO: 45;
- a heavy-chain CDR1 of SEQ ID NO: 27, a heavy-chain CDR2 of SEQ ID NO: 28, a heavy-chain CDR3 of SEQ ID NO: 31, and a light-chain CDR1 of SEQ ID NO: 43, a light-chain CDR2 of SEQ ID NO: 44, and a light-chain CDR3 of SEQ ID NO: 45;
- a heavy-chain CDR1 of SEQ ID NO: 27, a heavy-chain CDR2 of SEQ ID NO: 28, a heavy-chain CDR3 of SEQ ID NO: 32, and a light-chain CDR1 of SEQ ID NO: 43, a light-chain CDR2 of SEQ ID NO: 44, and a light-chain CDR3 of SEQ ID NO: 45;
- a heavy-chain CDR1 of SEQ ID NO: 27, a heavy-chain CDR2 of SEQ ID NO: 28, a heavy-chain CDR3 of SEQ ID NO: 33, and a light-chain CDR1 of SEQ ID NO: 43, a light-chain CDR2 of SEQ ID NO: 44, and a light-chain CDR3 of SEQ ID NO: 45;
- a heavy-chain CDR1 of SEQ ID NO: 27, a heavy-chain CDR2 of SEQ ID NO: 28, a heavy-chain CDR3 of SEQ ID NO: 34, and a light-chain CDR1 of SEQ ID NO: 43, a light-chain CDR2 of SEQ ID NO: 44, and a light-chain CDR3 of SEQ ID NO: 45; and
- a heavy-chain CDR1 of SEQ ID NO: 27, a heavy-chain CDR2 of SEQ ID NO: 28, a heavy-chain CDR3 of SEQ ID NO: 35, and a light-chain CDR1 of SEQ ID NO: 43, a light-chain CDR2 of SEQ ID NO: 44, and a light-chain CDR3 of SEQ ID NO: 45.

Specifically, the antibody or antigen-binding fragment thereof that binds to IL-5Rα may include the heavy-chain and light-chain CDR sequences shown in Table 6 and/or Table 8 below.

The term "framework region" (FR) refers to a variable domain residue other than a CDR residue. Each variable domain typically has four FRs, identified as FR1, FR2, FR3, and FR4.

The antibody or antigen-binding fragment thereof binding to IL-4Rα may include a heavy-chain variable region including a sequence selected from the group consisting of SEQ ID NOS: 9 to 14 and/or a light-chain variable region including a sequence selected from the group consisting of SEQ ID NOS: 21 to 26.

In a specific embodiment of the present invention, the antibody or antigen-binding fragment thereof binding to IL-4Rα may include the following:

- a heavy-chain variable region of SEQ ID NO: 9 and a light-chain variable region of SEQ ID NO: 21;
- a heavy-chain variable region of SEQ ID NO: 10 and a light-chain variable region of SEQ ID NO: 22;
- a heavy-chain variable region of SEQ ID NO: 11 and a light-chain variable region of SEQ ID NO: 23;
- a heavy-chain variable region of SEQ ID NO: 12 and a light-chain variable region of SEQ ID NO: 22;
- a heavy-chain variable region of SEQ ID NO: 67 and a light-chain variable region of SEQ ID NO: 23;
- a heavy-chain variable region of SEQ ID NO: 68 and a light-chain variable region of SEQ ID NO: 22;
- a heavy-chain variable region of SEQ ID NO: 12 and a light-chain variable region of SEQ ID NO: 24;
- a heavy-chain variable region of SEQ ID NO: 10 and a light-chain variable region of SEQ ID NO: 25; or
- a heavy-chain variable region of SEQ ID NO: 12 and a light-chain variable region of SEQ ID NO: 26.

Specifically, the antibody or antigen-binding fragment thereof binding to IL-4Rα according to the present invention may include the heavy-chain and light-chain CDR sequences shown in Table 2 and/or Table 4 below.

The antibody or antigen-binding fragment thereof binding to IL-5Rα may include a heavy-chain variable region including a sequence selected from the group consisting of SEQ ID NOS: 36 to 42 and/or a light-chain variable region including a sequence of SEQ ID NO: 46.

In a specific embodiment of the present invention, the antibody or antigen-binding fragment thereof binding to IL-5Rα may include the following:

- the heavy-chain variable region of SEQ ID NO: 36 and the light-chain variable region of SEQ ID NO: 46;
- the heavy-chain variable region of SEQ ID NO: 37 and the light-chain variable region of SEQ ID NO: 46;
- the heavy-chain variable region of SEQ ID NO: 38 and the light-chain variable region of SEQ ID NO: 46;
- the heavy-chain variable region of SEQ ID NO: 39 and the light-chain variable region of SEQ ID NO: 46;
- the heavy-chain variable region of SEQ ID NO: 40 and the light-chain variable region of SEQ ID NO: 46;
- the heavy-chain variable region of SEQ ID NO: 41 and the light-chain variable region of SEQ ID NO: 46; or
- the heavy-chain variable region of SEQ ID NO: 42 and the light-chain variable region of SEQ ID NO: 46.

The antibody or antigen-binding fragment thereof binding to IL-4Rα according to the present invention may include the heavy-chain and light-chain CDR sequences shown in Table 7 and/or Table 9 below.

In addition, the bispecific antibody or antigen-binding fragment thereof according to the present invention also includes an antibody or antigen-binding fragment thereof in which a part of the amino acid sequence is substituted in the bispecific antibody or antigen-binding fragment thereof according to the present invention through conservative substitution.

As used herein, the term "conservative substitution" refers to modifications of polypeptides that involve the substitution of one or more amino acids with other amino acids having similar biochemical properties that do not result in loss of the biological or biochemical function of the polypeptides. The term "conservative amino acid substitution" refers to substitution of the amino acid residue with an amino acid residue having a similar side chain. Families of amino acid residues having similar side chains have been defined and are well known in the art to which the present invention pertains. These families include amino acids with basic side chains (e.g., lysine, arginine and histidine), amino acids with acidic side chains (e.g., aspartic acid and glutamic acid), amino acids with uncharged polar side chains (e.g., glycine, asparagine, glutamine, serine, threonine, tyrosine, and cysteine), amino acids with nonpolar side chains (e.g., alanine, valine, leucine, isoleucine, proline, phenylalanine, methionine, and tryptophan), amino acids with beta-branched side chains (e.g., threonine, valine, and isoleucine), and amino acids with aromatic side chains (e.g., tyrosine, phenylalanine, tryptophan, and histidine). It is found that the antibody according to the present invention retains the activity thereof despite having conservative amino acid substitutions.

The bispecific antibody or antibody-binding fragment thereof according to the present invention may include not only an antibody but also biological equivalents thereto, as long as it can specifically recognize an antigen protein. For example, additional variations can be made to the amino acid sequence of the antibody in order to further improve the binding affinity and/or other biological properties of the antibody. Such variations include, for example, deletion, insertion and/or substitution of the amino acid sequence residues of the antibody. Such amino acid mutations are based on the relative similarity of amino-acid side-chain substituents, such as the hydrophobicity, hydrophilicity, charge and size thereof. It can be seen through analysis of the size, shape and type of amino-acid side-chain substituents that all of arginine, lysine and histidine are positively charged residues; alanine, glycine and serine have similar sizes; and phenylalanine, tryptophan and tyrosine have similar shapes. Thus, based on these considerations, arginine, lysine and histidine; alanine, glycine and serine; and phenylalanine, tryptophan and tyrosine are considered to be biologically functional equivalents.

When taking into consideration mutations having biologically equivalent activity, the antibody or a nucleotide molecule encoding the same according to the present invention is interpreted to include a sequence having substantial identity with the sequence set forth in the sequence number. The term "substantial identity" means that a sequence has a homology of at least 90%, preferably a homology of at least 90%, most preferably at least 95%, at least 96%, at least 97%, at least 98%, and at least 99%, when aligning the sequence of the present invention and any other sequence so as to correspond to each other as much as possible and analyzing the aligned sequence using algorithms commonly used in the art. Alignment methods for sequence comparison are well-known in the art. The NCBI Basic Local Alignment Search Tool (BLAST) is accessible through NCBI or the like, and can be used in conjunction with sequence analysis programs such as BLASTP, BLASTM, BLASTX, TBLASTN and TBLASTX over the Internet. BLAST is available at www.ncbi.nlm.nih.gov/BLAST/. A method of comparing sequence homology using this program can be found at www.ncbi.nlm.nih.gov/BLAST/blast_help.html.

Based on this, the bispecific antibody or antigen-binding fragment thereof according to the present invention can have a homology of 90%, 91%, 92%, 93%, 94%, 95%, 96%, 97%, 98%, 99%, or more compared to the sequence disclosed herein or the entirety thereof. Homology can be determined through sequence comparison and/or alignment by methods known in the art. For example, the percentage sequence homology of the nucleic acid or protein according to the present invention can be determined using a sequence comparison algorithm (i.e., BLAST or BLAST 2.0), manual alignment, or visual inspection.

In another aspect, the present invention is directed to a nucleic acid encoding the bispecific antibody or an antigen-binding fragment thereof. The antibody or antigen-binding fragment thereof can be produced in a recombinant manner by isolating the nucleic acid encoding the antibody or antigen-binding fragment thereof of the present invention.

The term "nucleic acid" is intended to encompass both DNA (gDNA and cDNA) and RNA molecules, and a nucleotide, which is a basic constituent unit of a nucleic acid, includes naturally derived nucleotides as well as analogues, wherein sugar or base moieties are modified. The sequence of the nucleic acid encoding heavy- and light-chain variable regions of the present invention can vary. Such variation includes addition, deletion, or non-conservative or conservative substitution of nucleotides.

The DNA encoding the bispecific antibody can be easily separated or synthesized using conventional molecular biological techniques (for example, using an oligonucleotide probe capable of specifically binding to DNA encoding heavy and light-chains of the antibody). Nucleic acids are isolated and inserted into replicable vectors for further cloning (amplification of DNA) or further expression. Based on this, in another aspect, the present invention is directed to a recombinant expression vector including the nucleic acid.

As used herein, the term "vector" refers to a means for expressing target genes in host cells, and includes plasmid vectors, cosmid vectors, and viral vectors such as bacteriophage vectors, adenovirus vectors, retroviral vectors and adeno-associated viral vectors. Vector components generally include, but are not limited to, one or more of the following components: signal sequences, replication origins, one or more antibiotic resistance marker genes, enhancer elements, promoters, and transcription termination sequences. The nucleic acid encoding the antibody is operably linked to promoters, transcription termination sequences or the like.

The term "operably linked" means a functional linkage between a nucleic acid expression regulation sequence (e.g., an array of promoter, signal sequence or transcription regulator binding sites) and another nucleic acid sequence, and enables the regulation sequence to regulate the transcription and/or translation of the other nucleic acid sequence.

When a prokaryotic cell is used as a host, it generally includes a potent promoter capable of conducting transcription (such as a tac promoter, a lac promoter, a lacUV5 promoter, a lpp promoter, a pLλ promoter, a pRλ promoter, a racy promoter, an amp promoter, a recA promoter, SP6 promoter, a trp promoter, or a T7 promoter), a ribosome-binding site for initiation of translation, and a transcription/translation termination sequence. In addition, for example, when a eukaryotic cell is used as a host, it includes a promoter (e.g., a metallothionein promoter, a β-actin promoter, a human hemoglobin promoter and a human muscle creatine promoter) derived from the genome of mammalian cells, or a promoter derived from a mammalian virus such as an adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein-Barr virus (EBV) promoter, or Rous sarcoma virus (RSV) promoter, and generally has a polyadenylation sequence as a transcription termination sequence.

Optionally, the vector may be fused with another sequence in order to facilitate purification of the antibody expressed therefrom. The sequence to be fused therewith includes, for example, glutathione S-transferase (Pharmacia, USA), maltose-binding protein (NEB, USA), FLAG (IBI, USA), 6×His (hexahistidine; Qiagen, USA) and the like.

The vector includes antibiotic-resistance genes commonly used in the art as selectable markers, and examples thereof include genes conferring resistance to ampicillin, gentamycin, carbenicillin, chloramphenicol, streptomycin, kanamycin, geneticin, neomycin and tetracycline.

In another aspect, the present invention is directed to a cell transfected with the recombinant expression vector. The host cell used to produce the bispecific antibody of the present invention may be a prokaryote, yeast or higher eukaryotic cell, but is not limited thereto.

Prokaryotic host cells such as *Escherichia coli*, the genus *Bacillus*, such as *Bacillus subtilis* and *Bacillus thuringiensis, Streptomyces* spp., *Pseudomonas* spp. (for example, *Pseudomonas putida*), *Proteus mirabilis* and *Staphylococcus* spp. (for example, *Staphylococcus carnosus*) can be used.

Interest in animal cells is the greatest, and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, and HT1080.

In another aspect, the present invention is directed to a method of producing a bispecific antibody (IL-4Rα×IL-5Rα) or antigen-binding fragment thereof including culturing the host cells to produce an (IL-4Rα×IL-5Rα) bispecific antibody binding to both IL-4Rα and IL-5Rα, or antigen-binding fragment thereof, and isolating the produced IL-4Rα×IL-5Rα bispecific antibody or antigen-binding fragment thereof from the cultured cells, followed by purification.

Specifically, the method of producing a bispecific antibody (IL-4Rα×IL-5Rα) or antigen-binding fragment thereof includes, but is not limited to:

(a) culturing host cells expressing the (IL-4Rα×IL-5Rα) bispecific antibody or antigen-binding fragment thereof according to the present invention to produce a bispecific antibody (IL-4Rα×IL-5Rα) or antigen-binding fragment thereof; and (b) recovering the produced IL-4Rα×IL-5Rα bispecific antibody or antigen-binding fragment thereof.

The host cells can be cultured in various media. Any commercially available medium can be used as a culture medium without limitation. All other essential supplements well-known to those skilled in the art may be included in appropriate concentrations. Culture conditions such as temperature and pH are those that are conventionally used with the host cells selected for expression, which will be apparent to those skilled in the art.

The recovery of the IL-4Rα×IL-5Rα bispecific antibody or antigen-binding fragment thereof can be carried out, for example, by centrifugation or ultrafiltration to remove impurities and further purification of the resulting product using, for example, affinity chromatography. Other additional purification techniques such as anion or cation exchange chromatography, hydrophobic interaction chromatography and hydroxyapatite (HA) chromatography may be used.

In another aspect, the present invention is directed to a conjugate in which the IL-4Rα×IL-5Rα bispecific antibody or antigen-binding fragment thereof is fused with a bioactive molecule selected from the group consisting of peptides, proteins, small-molecule drugs, nucleic acids, nanoparticles and liposomes.

The proteins include antibodies, fragments of antibodies, immunoglobulins, peptides, enzymes, growth factors, cytokines, transcription factors, toxins, antigenic peptides, hormones, transport proteins, motor function proteins, receptors, signaling proteins, storage proteins, membrane proteins, transmembrane proteins, internal proteins, external proteins, secreted proteins, viral proteins, sugar proteins, truncated proteins, protein complexes, chemically modified proteins and the like.

The term "small-molecule drugs" refers to an organic compound, an inorganic compound or an organometallic compound that has a molecular weight of less than about 1,000 Da and has activity as a therapeutic agent for diseases, which is widely used herein. The small-molecule drug used herein includes oligopeptides and other biomolecules having a molecular weight of less than about 1,000 Da.

As used herein, the term "nanoparticle" refers to a particle including a material having a diameter of 1 to 1,000 nm, and the nanoparticle may be a metal/metal core-shell complex including a metal nanoparticle, a metal nanoparticle core and a metal shell including the core, a metal/non-metal core-shell complex including a metal nanoparticle core and a non-metal shell surrounding the core, or a nonmetal/metal core-shell complex including a nonmetal nanoparticle core and a metal shell surrounding the core. According to one embodiment, the metal may be selected from gold, silver, copper, aluminum, nickel, palladium, platinum, magnetic iron, and oxides thereof, but is not limited thereto, and the nonmetal may be selected from silica, polystyrene, latex and acrylic substances, but is not limited thereto.

The liposome consists of one or more lipid bilayer membranes surrounding an aqueous internal compartment that can self-associate. Liposomes can be specified based on the type and size of the membrane thereof. Small unilamellar vesicles (SUVs) have a single membrane, and may have a diameter of 20 nm to 50 nm. Large unilamellar vesicles (LUV) may have a diameter of 50 nm or more. Oligolamellar large vesicles and multilamellar large vesicles have multiple, generally concentric, membrane layers, and may be 100 nm or more in diameter. Liposomes having a plurality of non-concentric membranes, that is, several small vesicles contained within larger vesicles, are called "multivesicular vesicles".

As used herein, the term "fusion" refers to the integration of two molecules having different or identical functions or structures, and includes fusion through any physical, chemical or biological method capable of binding the bispecific antibody or antigen-binding fragment thereof to the protein, small-molecule drug, nanoparticle, or liposome. The fusion may preferably be carried out using a linker peptide, and the linker peptide may mediate the fusion with the bioactive molecule at various positions of the antibody light-chain variable region, antibody, or fragment thereof according to the present invention.

As used herein, the term "effector function" refers to the type of biological activity associated with the Fc region of an antibody (wild-type sequence of the Fc region or a variant of the amino acid sequence of the Fc region) and depends on the isotype of the antibody. Examples of antibody effector functions include C1q binding, complement dependent cytotoxicity (CDC); Fc receptor binding, antibody dependent cell-mediated cytotoxicity (ADCC), phagocytosis, down-regulation of cell surface receptors (e.g., B-cell receptor, BCR) and B-cell activation.

The term "antibody-dependent cellular cytotoxicity" or "ADCC" refers to a reaction in which effector cells (e.g., T-cells and NK-cells) lyse target cells labeled by a specific antibody. ADCC is also independent of the immune complement system, which lyses the target, but does not require other cells. ADCC typically requires effector cells known to be natural killer (NK) cells that interact with immunoglobulin G (IgG) antibodies. However, macrophages, neutrophils and eosinophils can also mediate ADCC, for example, eosinophils that kill certain parasitic worms known as parasites via IgE antibodies.

The bioactive molecule that can be conjugated to the IL-4Rα×IL-5Rα bispecific antibody or antigen-binding fragment thereof according to the present invention is a small molecule drug, particularly preferably a drug that is effective in the treatment of allergic diseases, inflammatory diseases, and/or diseases caused by an increase in eosinophils, for example, hypereosinophilic syndrome (HES), hypereosinophilia, asthma including eosinophilic asthma, eosinophilic bronchial asthma (ABA) and severe eosinophilic bronchial asthma (ABA), chronic obstructive pulmonary disease (COPD), Churg-Strauss syndrome, eosinophilic esophagitis, eosinophilic gastroenteritis, eosinophilic gastrointestinal disease (EGID), atopic diseases such as atopic dermatitis, allergic diseases such as allergic rhinitis, immunoglobulin (IgE)-mediated food allergy, inflammatory bowel disease, allergic colitis, gastroesophageal reflux, endocardial myocardial fibrosis, Loeffler endocarditis, Davis disease, intermittent angioedema associated with eosinophilia, eosinophilia-myalgia syndrome/Spanish toxic oil syndrome, liver cirrhosis, dermatitis impetigo, bullous pemphigoid, Churg-Strauss syndrome, acute myelogenous eosinophilic leukemia, acute lymphocytic eosinophilic leukemia, systemic mast cell disease with eosinophilia, eczema, Wegner's granulomatosis, polyarteritis nodosa, eosinophilic vasculitis, rheumatoid arthritis, and the like.

More preferably, examples of the bioactive molecule include, but are not limited to, beta agonists such as indacaterol, formoterol, vilanterol, albuterol, levalbuterol, and theophylline, anticholinergic agents such as ipratropium, tiotropium, and glycopyrrolate, and leukotriene modifiers such as montelukast, zafirlukast, and zileuton.

As used herein, the term "inhibits the activity of IL-4, IL-5, or IL-13" means that the bispecific antibody that simultaneously binds to and targets IL-4Rα and IL-5Rα of the present invention (IL-4Rα×IL-5Rα) is capable of inhibiting the cellular activity induced by IL-4 or IL-5 by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%.

In another aspect, the present invention is directed to a pharmaceutical composition for preventing or treating allergic diseases, inflammatory diseases, and/or diseases caused by an increase in eosinophils, especially, diseases caused by an increase in eosinophils, containing the bispecific antibody (IL-4Rα×IL-5Rα) or antigen-binding fragment thereof as an active ingredient.

Examples of diseases that can be treated using the IL-4Rα×IL-5Rα bispecific antibody or antigen-binding fragment thereof according to the present invention include, but are not limited to, hypereosinophilic syndrome (HES), hypereosinophilia, asthma, including eosinophilic asthma, eosinophilic bronchial asthma (ABA) and severe eosinophilic bronchial asthma (ABA), chronic obstructive pulmonary disease (COPD), Churg-Strauss syndrome, eosinophilic esophagitis, eosinophilic gastroenteritis, eosinophilic gastrointestinal disease (EGID), atopic diseases such as atopic dermatitis, allergic diseases such as allergic rhinitis, food allergy, such as immunoglobulin (IgE)-mediated food allergy, inflammatory bowel disease, allergic colitis, gastroesophageal reflux, endocardial myocardial fibrosis, Loeffler endocarditis, Davis disease, intermittent angioedema associated with eosinophilia, eosinophilia-myalgia syndrome/Spanish toxic oil syndrome, liver cirrhosis, dermatitis impetigo, bullous pemphigoid, Churg-Strauss syndrome, acute myelogenous eosinophilic leukemia, acute lymphocytic eosinophilic leukemia, systemic mast cell disease with eosinophilia, eczema, Wegner's granulomatosis, polyarteritis nodosa, eosinophilic vasculitis, rheumatoid arthritis, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, nephritis, herpes, chronic idiopathic urticarial, scleroderma, hypertrophic scarring, Whipple's disease, benign prostatic hyperplasia, mild or inflammatory disorders such as inflammatory bowel disease.

In another aspect, the present invention is directed to a pharmaceutical composition for preventing or treating allergic diseases, inflammatory diseases, and/or diseases caused by an increase in eosinophils, including (a) a pharmaceutically effective amount of the IL-4Rα×IL-5Rα bispecific antibody or antigen-binding fragment thereof according to the present invention, and (b) a pharmaceutically acceptable carrier.

The present invention also relates to a method for preventing or treating allergic diseases, inflammatory diseases and/or diseases caused by an increase in eosinophils, including administering the IL-4Rα×IL-5Rα bispecific antibody or antigen-binding fragment thereof according to the present invention in an effective amount required for a patient.

The IL-4Rα×IL-5Rα bispecific antibody according to the present invention is useful for the prevention or treatment of IL-4, IL-5, and/or IL-13-mediated diseases by removing, inhibiting, or reducing IL-4, IL-5, and/or IL-13 activity. The antibody according to the present invention binds to IL-4Rα and/or IL-5Rα and is used for the treatment of diseases associated with IL-4, IL-5 and/or IL-13 activity.

In order to treat the autoimmune disease or related autoimmune condition, the bispecific antibody of the present invention can be administered to a patient in combination with other therapeutic agents using multi-drug therapy. The IL-4Rα×IL-5Rα bispecific antibody or antigen-binding fragment thereof according to the present invention may be administered simultaneously with, sequentially or alternately with immunosuppressive agents, or after resistance to other therapies appears. Immunosuppressive agents may be administered in an amount identical to or lower than that used in the art. The selection of preferred immunosuppressive agent may depend on many factors, including the type of disease to be treated and the patient's medical history.

As used herein, the term "prevention" refers to any action causing the suppression of growth of allergic diseases, inflammatory diseases, and/or diseases caused by an increase in eosinophils or the delay of progression of such diseases by administration of the composition according to the present invention. The term "treatment" means suppression of the progression of allergic diseases, inflammatory diseases, and/or diseases caused by an increase in eosinophils or alleviation or elimination of such diseases. The antibodies of the present invention can be useful both in vitro and in vivo for applications involving cells expressing IL-4Rα and/or IL-5Rα.

The pharmaceutical composition of the present invention contains the IL-4Rα×IL-5Rα bispecific antibody or antigen-binding fragment thereof or the conjugate according to the present invention, and the pharmaceutical composition may further contain a pharmaceutically acceptable carrier, in addition to the component for administration of the pharmaceutical composition of the present invention. The term "pharmaceutically acceptable carrier" as used herein refers to a carrier or diluent that does not impair the biological activities or properties of the administered compound and does not stimulate an organism. Pharmaceutically acceptable carriers for compositions that are formulated into liquid solutions are sterilized and biocompatible, and examples thereof include saline, sterile water, buffered saline, albumin injection solutions, dextrose solutions, maltodextrin solutions, glycerol, and mixtures of one or more thereof. If necessary, other conventional additives such as antioxidants, buffers and bacteriostatic agents may be added. In addition, diluents, dispersants, surfactants, binders and lubricants can be additionally added to formulate injectable solutions such as aqueous solutions, suspensions and emulsions, pills, capsules, granules, or tablets.

The pharmaceutical composition according to the present invention may be any one of various oral or parenteral formulations. In this regard, the pharmaceutical composition may be formulated using an ordinary diluent or excipient such as a filler, a thickener, a binder, a wetting agent, a disintegrant, a surfactant, or the like. Solid formulations for oral administration may include tablets, pills, powders, granules, capsules and the like. Such a solid formulation is prepared by mixing at least one compound with at least one excipient such as starch, calcium carbonate, sucrose, lactose or gelatin. In addition to a simple excipient, a lubricant such as magnesium stearate or talc may be further used. Liquid formulations for oral administration may include suspensions, solutions for internal use, emulsions, syrups, and the like. In addition to a simple diluent such as water or liquid paraffin, various excipients such as wetting agents, sweeteners, aromatics and preservatives may be incorporated in the liquid formulations. In addition, formulations for parenteral administration include sterile aqueous solutions, non-aqueous solvents, suspensions, emulsions, lyophilizates, suppositories and the like. Useful non-aqueous solvents and suspensions include propylene glycol, polyethylene glycol, vegetable oils such as olive oil and injectable esters such as ethyl oleate. The base ingredients of suppositories include Witepsol, macrogol, Tween 61, cacao butter, laurin butter and glycerogelatin.

The method for treating inflammatory diseases using the IL-4Rα×IL-5Rα bispecific antibody or antigen-binding fragment thereof or the conjugate according to the present invention includes administering, to a subject, a pharmaceutically effective amount of the antibody or antigen-binding fragment thereof, or the conjugate. It will be apparent to those skilled in the art that an appropriate total daily dose can be determined based on the judgment of a medical specialist. In addition, the IL-4Rα×IL-5Rα bispecific antibody, antigen-binding fragment thereof, or the conjugate may be administered in a single dose, or may be divided into multiple doses. However, in consideration of the objects of the present invention, the specific therapeutically effective amount for a certain patient is preferably determined depending upon a variety of factors, including the type and extent of the response to be achieved, as well as the presence of other agents used, the specific composition, the age, body weight, general state of health, gender, and diet of the patient, the administration time, the administration route, the treatment period, and drugs used in conjunction with or concurrently with the specific composition, and other similar factors well-known in the field of pharmaceuticals.

The subject to which the composition of the present invention is administered includes mammals including humans, without limitation thereto.

As used herein, the term "administration" refers to an action of supplying the pharmaceutical composition according to the present invention to a patient by any appropriate method, and the composition according to the present invention may be orally or parenterally administered through any one of various routes enabling the composition to be delivered to a target tissue.

The IL-4Rα×IL-5Rα bispecific antibody or antigen-binding fragment thereof according to the present invention may be used as a single drug or in combination with a conventional therapeutic agent.

Any drug may be used without limitation as the drug that can be used in combination therapy with the antibody according to the present invention so long as it can be used to treat diseases caused by an increase in eosinophils, for example, hypereosinophilic syndrome (HES), hypereosinophilia, asthma, including eosinophilic asthma, eosinophilic bronchial asthma (ABA) and severe eosinophilic bronchial asthma (ABA), chronic obstructive pulmonary disease (COPD), Churg-Strauss syndrome, eosinophilic esophagitis, eosinophilic gastroenteritis, eosinophilic gastrointestinal disease (EGID), atopic diseases such as atopic dermatitis, allergic diseases such as allergic rhinitis, food allergy, such as immunoglobulin (IgE)-mediated food allergy, inflammatory bowel disease, allergic colitis, gastroesophageal reflux, endocardial myocardial fibrosis, Loeffler endocarditis, Davis disease, intermittent angioedema associated with eosinophilia, eosinophilia-myalgia syndrome/Spanish toxic oil syndrome, liver cirrhosis, dermatitis impetigo, bullous pemphigoid, Churg-Strauss syndrome, acute myelogenous eosinophilic leukemia, acute lymphocytic eosinophilic leukemia, systemic mast cell disease with eosinophilia, eczema, Wegner's granulomatosis, polyarteritis nodosa, eosinophilic vasculitis, and rheumatoid arthritis.

Preferably, examples of the drug include, but are not limited to, beta agonists such as indacaterol, formoterol, vilanterol, albuterol, levalbuterol, and theophylline, anticholinergic agents such as ipratropium, tiotropium, and glycopyrrolate, leukotriene modifiers such as montelukast, zafirlukast, and zileuton, inhaled corticosteroids such as fluticasone propionate, budesonide, ciclesonide, beclomethasone, and mometasone, and anti-IgE antibodies such as omalizumab and ligelizumab.

In addition, the present invention is directed to a method for treating a disease including administering the IL-4Rα×IL-5Rα bispecific antibody or antigen-binding fragment thereof according to the present invention to a patient in need of treatment.

In another aspect, the present invention is directed to a composition for diagnosing allergic diseases, inflammatory diseases, and/or diseases caused by an increase in eosinophils including the IL-4Rα×IL-5Rα bispecific antibody or antigen-binding fragment thereof. In another aspect, the present invention is directed to a kit for diagnosing allergic diseases, inflammatory diseases, and/or diseases caused by an increase in eosinophils containing the composition diagnosing the diseases.

As used herein, the term "diagnosis" means determining the presence or features of pathophysiology. In the present invention, diagnosis serves to determine the onset or progress of diagnosing allergic diseases, inflammatory diseases, and/or diseases caused by an increase in eosinophils.

For diagnostic methods using the IL-4Rα×IL-5Rα bispecific antibody or antigen-binding fragment thereof according to the present invention, the drug may include a detectable label used to detect the presence of IL-4Rα antigen-expressing cells in vitro or in vivo. Rα dioisotopes that are detectable in vivo such as labels that can be detected using scintillation, magnetic resonance imaging or ultrasound can be used for clinical diagnostic applications. Useful scintillation labels include positron emitters and γ-emitters. Representative contrast agents as magnetic sources for imaging include paramagnetic or superparamagnetic ions (e.g., iron, copper, manganese, chromium, erbium, europium, dysprosium, holmium and gadolinium), iron oxide particles, and water-soluble contrast agents. For ultrasonic detection, a gas or liquid can be trapped in the porous inorganic particles released as a microbubble contrast agent. Detectable labels useful for in-vitro detection include fluorophores, detectable epitopes or binders and radiolabels.

The kit for diagnosing allergic diseases, inflammatory diseases, and/or diseases caused by an increase in eosinophils may further include a composition, solution or device having one or more other components suitable for the analysis method.

In one embodiment, the kit may include a bottle, vial, bag, needle, or syringe. The container may be made from various materials, such as glass, plastic, or metal. The label on the container may provide instructions for use. The kit may further include other materials desirable from commercial and usage perspectives, such as other buffers, diluents, filters, needles and syringes.

Hereinafter, the present invention will be described in more detail with reference to examples. However, it will be obvious to those skilled in the art that these examples are provided only for illustration of the present invention and should not be construed as limiting the scope of the present invention.

Example 1: Construction of Yeast Cell Surface Expression Library for Increasing 4R34.1.19-Based Affinity The present inventors aimed to increase the affinity for IL-4Rα in order to increase the biological efficacy of the 4R34.1.19 antibody (Kim et al., 2019). The sequence of the IL-4Rα antigen is represented by SEQ ID NO: 65. Since IL-4Rα is a cell membrane glycoprotein, "sIL-4Rα" refers to a product obtained by introducing the sequence of IL-4Rα represented by SEQ ID NO: 65, which is an extracellular domain, into an animal cell expression vector and expressing the same in the vector.

First, in order to express a single-chain Fab (scFab) on the yeast surface, a 4R34.1.19 antibody was constructed in the form of scFab in a pYDS-H vector treated with a NheI/ApaI restriction enzyme to clone the pYDS 4R34.1.19 scFab vector and a pYDS-dummy vector in which a stop codon is generated due to an open reading frame (ORF) shifted due to one additionally introduced nucleotide. By using the pYDS-dummy vector, even if a vector that has not been treated with a restriction enzyme is mixed, only the vector containing the desired library gene can express scFab on the yeast surface. Regarding the library, random mutations were introduced into the VH-CDR2 and VL-CDR3 regions, among the six CDRs based on the pYDS 4R34.1.19 scFab vector (FIG. 1). Spiked oligomers were used to prevent the loss of binding ability to IL-4Rα because mutations were introduced simultaneously in many regions. This is a mutation method to which all amino acids can be applied while preserving the conventional wild-type 4R34.1.19 sequence with 50% probability and is a technology that ensures 50% of wild-type amino acids during the PCR process by designing primers while maintaining 79% of wild-type nucleotides and 7% of the remaining nucleotides in the three nucleotides encoding amino acids.

Overlapping PCR was performed to prepare 12 μg of the library gene and 4 μg of the pYDS dummy vector treated with NheI/ApaI restriction enzymes. Although the pYDS dummy vector that has not been treated with the restriction enzyme remains and thus is transformed into a yeast strain, it is not expressed on the yeast surface by the stop codon. The two genes were mixed and transformed into a yeast AWT101 strain for yeast surface expression by electroporation, and constructed through homologous recombination. This process was repeated 12 times, serial dilution was then performed, and then the library size was detected by measuring the number of colonies grown in a SD-CAA+Trp selection medium (20 g/L glucose, 6.7 g/L yeast nitrogen base without amino acids, 5.4 g/L $Na_2HPO_4$, 8.6 g/L $NaH_2PO_4$, 5 g/L casamino acids, 0.4 mg/L tryptophan). The library that was produced had a size of about $1\times10^8$.

Example 2: Kinetic Screening Regarding IL-4Rα Antigen Protein of Yeast scFab Library The constructed library was screened through magnetic-activated cell sorting by binding scFab ($5\times10^9$ scFab yeast) expressed in cells to 1 nM biotinylated sIL-4Rα (IL-4Rα). Then, kinetic screening was performed to select clones having a low dissociation rate for IL-4Rα. Specifically, in the first and second FACS (fluorescence activated cell sorting), scFab ($5\times10^7$ scFab yeast) expressed in cells was bound to 5 nM biotinylated sIL-4Rα for 30 minutes at room temperature and then unbound biotinylated sIL-4Rα was washed. Then, to isolate sIL-4Rα from yeast, the product was resuspended in 1 ml of autoMACS® running buffer (phosphate buffered saline (PBS), bovine serum albumin (BSA), EDTA, and 0.09% azide, pH 7.2, Miltenyi Biotec) and then was shaking-incubated at 37° C. for 1 hour. In the third and fourth FACS, 50 nM of non-biotinylated sIL-4Rα was added thereto upon resuspension to perform competition to prevent the dissociated biotinylated sIL-4Rα from rebinding. In the fifth FACS, the dissociated biotinylated sIL-4Rα was removed and then resuspended in a buffer containing 50 nM of non-biotinylated sIL-4Rα repeatedly 4 times. After dissociation conditions were completed each time, anti-cMyc antibody 9E10 was diluted 1:100 and bound at room temperature for 15 minutes, so that the expression level could be determined. Then, PE-conjugated streptavidin (streptavidin-R-phycoerythrin conjugate, SA-PE, Thermo) was bound to Alexa 488-conjugated anti-IgG antibody (goat Alexa 488-conjugated anti-Fc antibody, Thermo) at 4° C. for 15 minutes, the top 0.2-0.3% clones having high scFab expression and maintaining binding to biotinylated sIL-4Rα were screened using a BD FACSAria™ III device.

Eight individual clones having high binding ability of sIL-4Rα to the surface of yeast cells (4R.N1, 4R.N2, 4R.N3, 4R.N4, 4R.N5, 4R.N6, 4R.N7, 4R.N8) were identified by the screening described above.

Tables 1 and 2, respectively, show the heavy-chain CDR sequences and heavy-chain variable region sequences of the selected 8 individual clones having binding ability to 4R34.1.19 and sIL-4Rα, and Tables 3 and 4, respectively, show light-chain CDR sequences and light-chain variable region sequences.

TABLE 1

| Heavy-chain variable region name | CDR1 sequence | | | | | CDR2 sequence | | | | | | | | | | | | | | | | | CDR3 sequence | | | | | | |
|---|---|---|---|---|---|---|---|---|---|---|---|---|---|---|---|---|---|---|---|---|---|---|---|---|---|---|---|---|---|
| | Kabat No. | | | | | | | | | | | | | | | | | | | | | | | | | | | | |
| | 31 | 32 | 33 | 34 | 35 | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 101 | 102 |
| 4R34.1.19 | R | H | A | M | A | A | I | T | S | S | G | R | S | I | Y | Y | A | D | S | V | K | G | V | H | R | A | F | D | Y |
| | SEQ ID No: 1 | | | | | SEQ ID No: 2 | | | | | | | | | | | | | | | | | SEQ ID No: 8 | | | | | | |
| 4R.N1 | R | H | A | M | A | A | I | T | A | S | G | R | S | I | Y | Y | A | D | S | V | K | G | V | H | R | A | F | D | Y |
| | SEQ ID No: 1 | | | | | SEQ ID No: 3 | | | | | | | | | | | | | | | | | SEQ ID No: 8 | | | | | | |
| 4R.N2 | R | H | A | M | A | A | I | T | A | S | G | R | G | I | Y | Y | G | D | S | V | K | G | V | H | R | A | F | D | Y |
| | SEQ ID No: 1 | | | | | SEQ ID No: 4 | | | | | | | | | | | | | | | | | SEQ ID No: 8 | | | | | | |
| 4R.N3 | R | H | A | M | A | A | I | T | M | S | G | R | S | I | Y | Y | A | D | S | V | K | G | V | H | R | A | F | D | Y |
| | SEQ ID No: 1 | | | | | SEQ ID No: 5 | | | | | | | | | | | | | | | | | SEQ ID No: 8 | | | | | | |
| 4R.N4 | R | H | A | M | A | A | I | T | M | S | G | R | G | I | Y | Y | A | D | S | V | K | G | V | H | R | A | F | D | Y |
| | SEQ ID No: 1 | | | | | SEQ ID No: 6 | | | | | | | | | | | | | | | | | SEQ ID No: 8 | | | | | | |
| 4R.N5 | R | H | A | M | A | A | I | T | A | S | G | M | S | I | Y | Y | A | D | F | A | K | G | V | H | R | A | F | D | Y |
| | SEQ ID No: 1 | | | | | SEQ ID No: 7 | | | | | | | | | | | | | | | | | SEQ ID No: 8 | | | | | | |
| 4R.N6 | R | H | A | M | A | A | I | T | M | S | G | R | S | I | Y | Y | A | D | S | V | K | G | V | H | R | A | F | D | Y |
| | SEQ ID No: 1 | | | | | SEQ ID No: 5 | | | | | | | | | | | | | | | | | SEQ ID No: 8 | | | | | | |
| 4R.N7 | R | H | A | M | A | A | I | T | A | S | G | R | S | I | Y | Y | A | D | S | V | K | G | V | H | R | A | F | D | Y |
| | SEQ ID No: 1 | | | | | SEQ ID No: 3 | | | | | | | | | | | | | | | | | SEQ ID No: 8 | | | | | | |
| 4R.N8 | R | H | A | M | A | A | I | T | M | S | G | R | S | I | Y | Y | A | D | S | V | K | G | V | H | R | A | F | D | Y |
| | SEQ ID No: 1 | | | | | SEQ ID No: 5 | | | | | | | | | | | | | | | | | SEQ ID No: 8 | | | | | | |

TABLE 2

| Heavy chain variable region name | Sequence | SEQ ID NO: |
|---|---|---|
| 4R34.1.19 | EVQLLESGGGLVQPGGSLRL SCAASGFTFSRHAMAWVRQA PGKGLEWVSAITSSGRSIYY ADSVKGRFTISRDNSKNTLY LQMNSIRAEDTAVYYCARVH RAFDYWGQGTLVTVSS | SEQ ID No: 9 |
| 4R.N1 | EVQLLESGGGLVQPGGSLRL SCAASGFTFSRHAMAWVRQA PGKGLEWVSAITASGRSIYY ADSVKGRFTISRDNSKNTLY LQMNSLRAEDTAVYYCARVH RAFDYWGQGTLVTVSS | SEQ ID No: 10 |
| 4R.N2 | EVQLLESGGGLVQPGGSLRL SCAASGFTFSRHAMAWVRQA PGKGLEWVSAITASGRSIYY GDSVKGRFTISRDNSKNTLY LQMNSLRAEDTAVYYCARVH RAFDYWGQGTLVTVSS | SEO ID No: 11 |
| 4R.N3 | EVQLLESGGGLVQPGGSLRL SCAASGFTFSRHAMAWVRQA PGKGLEWVSAITMSGRSIYY ADSVKGRFTISRDNSKNTLY LQMNSLRAEDTAVYYCARVH RAFDYWGQGTLVTVSS | SEQ ID No: 12 |
| 4R.N4 | EVQLLESGGGLVQPGGSLRL SCAASGFTFSRHAMAWVRQA PGKGLEWVSAITMSGRGIYY ADSVKGRFTISRDNSKNTLY LQMNSLRAEDTAVYYCARVH RAFDYWGQGTLVTVSS | SEQ ID No: 67 |

TABLE 2-continued

| Heavy chain variable region name | Sequence | SEQ ID NO: |
|---|---|---|
| 4R.N6 | EVQLLESGGGLVQPGGSLRL SCAASGFTFSRHAMAWVRQA PGKGLEWVSAITASGMSIVY ADFAKGRFTISRDNSKNTLY LQMNSLRAEDTAVYYCARVH RAFDYWGQGTLVTVSSY | SEQ ID No: 68 |
| 4R.N6 | EVQLLESGGGLVQPGGSLRL SCAASGFTFSRHAMAWVRQA PGKGLEWVSAITMSGRSIYY ADSVKGRFTISRDNSKNTLY LQMNSLRAEDTAVYYCARVH RAFDYWGQGTLVTVSS | SEQ ID No: 12 |
| 4R.N7 | EVQLLESGGGLVQPGGSLRL SCAASGFTFSRHAMAWVRQA PGKGLEWVSAITASGRSIYY GDSVKGRFTISRDNSKNTLY LQMNSLRAEDTAVYYCARVH RAFDYWGQGTLVTVSS | SEQ ID No: 10 |
| 4R.N8 | EVQLLESGGGLVQPGGSLRL SCAASGFTFSRHAMAWVRQA PGKGLEWVSAITMSGRSIYY ADSVKGRFTISRDNSKNTLY LQMNSLRAEDTAVYYCARVH RAFDYWGQGTLVTVSS | SEQ ID No: 12 |

TABLE 3

| Light-chain variable region name | CDR1 sequence | | | | | | | | | | | | | CDR2 sequence | | | | | | |
|---|---|---|---|---|---|---|---|---|---|---|---|---|---|---|---|---|---|---|---|---|
| | Kabat No. | | | | | | | | | | | | | | | | | | | |
| | 24 | 25 | 26 | 27 | 27a | 27b | 28 | 29 | 30 | 31 | 32 | 33 | 34 | 50 | 51 | 52 | 53 | 54 | 55 | 56 |
| 4R34.1.19 | S | G | S | P | L | F | P | D | S | G | S | E | N | A | D | S | H | R | P | S |
| | | | | | SEQ ID No: 13 | | | | | | | | | | | SEQ ID No: 14 | | | | |
| 4R.N1 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N2 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N3 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N4 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N5 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N6 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N7 | S | G | S | P | L | F | P | D | S | G | S | F | N | A | D | S | H | R | P | S |
| | | | | | SEQ ID No: 13 | | | | | | | | | | | SEQ ID No: 14 | | | | |
| 4R.N8 | S | G | S | P | L | F | F | D | S | G | S | F | N | A | D | S | H | R | P | S |
| | | | | | SEQ ID No: 13 | | | | | | | | | | | SEQ ID No: 14 | | | | |

| Light-chain variable region | CDR3 sequence Kabat No. | | | | | | | | | | |
|---|---|---|---|---|---|---|---|---|---|---|---|
| | 89 | 90 | 91 | 92 | 93 | 94 | 95 | 95a | 95b | 96 | 97 |
| 4R34.1.19 | G | T | W | D | Y | S | L | S | G | Y | V |
| | | | | | SEQ ID No: 15 | | | | | | |
| 4R.N1 | G | T | W | D | Y | S | L | N | R | Y | V |
| | | | | | SEQ ID No: 16 | | | | | | |
| 4R.N2 | G | T | W | D | Y | S | L | S | A | Y | V |
| | | | | | SEQ ID No: 17 | | | | | | |
| 4R.N3 | G | T | W | D | Y | S | L | N | R | Y | V |
| | | | | | SEQ ID No: 16 | | | | | | |
| 4R.N4 | G | T | W | D | Y | S | L | S | A | Y | V |
| | | | | | SEQ ID No: 17 | | | | | | |
| 4R.N5 | G | T | W | D | Y | S | L | N | R | Y | V |
| | | | | | SEQ ID No: 16 | | | | | | |
| 4R.N6 | G | T | W | D | Y | S | I | N | S | Y | V |
| | | | | | SEQ ID No: 18 | | | | | | |
| 4R.N7 | G | T | W | D | Y | S | L | S | S | Y | V |
| | | | | | SEQ ID No: 19 | | | | | | |
| 4R.N8 | G | S | W | D | Y | S | L | S | R | Y | V |
| | | | | | SEQ ID No: 20 | | | | | | |

TABLE 4

| Light-chain variable region name | Sequence | SEQ ID NO: |
|---|---|---|
| 4R34.1.19 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLSGYVLGGGTKLTVLG | SEQ ID No: 21 |
| 4R.N1 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLNRYVLGGGTKLTVLG | SEQ ID No: 22 |
| 4R.N2 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLSAYVLGGGTKLTVLG | SEQ ID No: 23 |
| 4R.N3 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLNRYVLGGGTKLTVLG | SEQ ID No: 22 |
| 4R.N4 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLSAYVLGGGTKLTVLG | SEQ ID No: 23 |
| 4R.N5 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLNRYVLGGGTKLTVLG | SEQ ID No: 22 |
| 4R.N6 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLNSYVLGGGTKLTVLG | SEQ ID No: 24 |
| 4R.N7 | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLSSYVLGGGTKLTVLG | SEQ ID No: 25 |
| 4R.NB | QSVLTQPPSASGTPGQRVTISCSGSPLFPDSGSFNWYQQLPGTAPKLLIYADSHRPSGVPDRFSGSKS GTSASLAISGLRSEDEADYYCGTWDYSLSRYVLGGGTKLTVLG | SEQ ID No: 26 |

Example 3: IgG Conversion and Identification of Selected Anti-IL-4Rα Antibodies The 8 antibodies selected in the form of scFab were converted into the form of IgG1, which is a commonly used antibody. The variable regions (VH, VL) of the selected antibody and dupilumab (DrugBank accession number; DB12159) as a control group were introduced into a pcDNA3.4 vector encoding the light-chains (CH1, CH2, CH3) and heavy-chain (CL) of IgG1. Then, dupilumab was called a "dupilumab analogue". The light and heavy-chains of respective antibodies were cotransformed at a ratio of 1:1 into HEK293F cells such that the light- and heavy-chains were expressed together in the cells.

Proteins were expressed and purified using transient transfection. In a shake flask, HEK293F cells suspension-grown in serum-free FreeStyle 293 expression medium were transfected with a mixture of plasmid and polyethyleneimine (PEI). Upon 100 mL transfection into the shake flask, HEK293F cells were seeded in 90 ml of medium at a density of $1.0\times10^6$ cells/ml and incubated at 120 rpm, 8% $CO_2$, and 37° C. The plasmid was diluted to 125 μg in 5 ml FreeStyle 293 expression medium and filtered, and PEI 375 μg (7.5 μg/ml) was mixed with 5 ml of diluted medium and allowed to react at room temperature for 10 minutes. Then, the reacted mixed medium was added to the cells seeded in 90 ml and incubated at 120 rpm and 8% $CO_2$ for 6 days. Proteins were purified from the cell incubation supernatant, which was collected with reference to standard protocols. The antibody was applied to a Protein A Sepharose column and washed with PBS (pH 7.4). The antibody was eluted at pH 3.0 using 0.1 M glycine and 0.5 M NaCl buffer, and the sample was immediately neutralized using 1 M Tris buffer. The eluted protein was concentrated using a Vivaspin 10,000 MWCO (Sartorius) centrifugal concentrator after exchanging the buffer with a storage buffer (PBS, pH 6.5). The absorbance of the purified protein at a wavelength of 562 nm was measured and the amount thereof was quantified using a solution in the BCA protein assay kit (Thermo) according to the drawn standard curve.

Example 4: Verification of Binding Ability of Selected Anti-IL-4Rα Antibodies The binding specificity of the antibody was determined using indirect ELISA. A multi-antigen ELISA was performed using four structurally different antigenic double-stranded DNA (dsDNA), insulin, the macromolecule hemocyanin, and the membrane component, cardiolipin. Specifically, sIL-4Rα antigen protein (50 ng/well, sinobio; 10402-H08H), sIL-5Rα antigen protein (50 ng/well, sinobio; 10392-H08H), dsDNA (25 ng/well, D4522; Sigma), insulin (125 ng/well, 19278; Sigma), hemocyanin (125 ng/well, H8283; Sigma), and cardiolipin (1250 ng/well, C0563; Sigma) proteins were immobilized on a 96-well plate at room temperature for 1 hour, and blocked using 2% skim milk containing 0.1% PBST (0.1% Tween20, pH 7.4, 137 mM NaCl, 10 mM phosphate, 2.7 mM KCl) at room temperature for 1 hour. After discarding the solution and then washing the same three times with 0.1% PBST, the antibody was diluted to 100 nM, added to the blocked plate in an amount of 25 μl/well, and allowed to react at room temperature for 1 hour. After discarding the solution and washing the same three times with 0.1% PBST, an anti-human Fc-HRP antibody (1:8000) as a secondary antibody was added in an amount of 25 μl/well and reacted at room temperature for 1 hour. After discarding the solution and washing three times with PBST, a TMB solution was added in an amount of 25 μl/well, color development was induced at room temperature for 2 minutes, the reaction was stopped using $H_2SO_4$ (2N), and the absorbance at 450 nm was measured with an ELISA reader.

As can be seen from the results of FIG. 2A, 4R34.1.19 exhibited binding ability to sIL-5Rα, but did not exhibit binding ability to other antigens, and the screened anti-IL-4Rα antibodies (4R.N1, 4R.N2, 4R.N3, 4R.N4, 4R.N5, 4R.N6, 4R.N7, and 4R.N8) exhibited almost no binding ability to sIL-5Rα and exhibited no binding ability to 4 types of proteins, which indicated that they have binding specificity to sIL-4Rα.

Example 5: Analysis of Binding Ability of Selected Anti-IL-4Rα Antibodies

In order to more quantitatively analyze binding ability to sIL-4Rα for selected anti-IL-4Rα antibodies (4R.N1, 4R.N2, 4R.N3, 4R.N4, 4R.N5, 4R.N6, 4R.N7, and 4R.N8), the binding ability was measured according to the protocol suggested by the manufacturer using an Octet $QK^e$ (ForteBio, USA) device. Specifically, the antibody was diluted to a concentration of 1 μg/ml in kinetic buffer (PBS pH 7.4+0.02% (v/v) Tween 20), sIL-4Rα (sinobio; 10402-H08H) was sequentially diluted at concentrations of 10, 5, 2.5, 1.25, 0.625, and 0 nM in kinetic buffer, and 200 μl of each dilution was injected into an opaque 96-well plate through which light does not pass. Antigen affinity of antibodies was analyzed through variation in the refractive index occurring when the antibody bound to the antigen was detached therefrom while the AHC (anti-human IgG Fc capture) sensor chip moved in the order of kinetic buffer, antibody dilution solution, kinetic buffer, antigen dilution solution, and kinetic buffer. Affinity was calculated with Octet Data Analysis software 11.0 in a 1:1 binding model. The results are shown in FIG. 2B.

Table 5 shows the results of analysis of affinity of selected anti-IL-4Rα antibodies to sIL-4Rα using Octet $QK^e$. It was confirmed that the selected clones had a high affinity of 43.1 to 170 pM.

TABLE 5

| | $K_D$(pM) | $k_{on}$(1/Ms) | $k_{off}$(1/s) |
|---|---|---|---|
| 4R34.1.19 | 120 ± 4.13 | (2.41 ± 0.04) × $10^6$ | (2.89 ± 0.09) × $10^{-4}$ |
| 4R.N1 | 170 ± 5.16 | (1.99 ± 0.03) × $10^6$ | (3.38 ± 0.09) × $10^{-4}$ |
| 4R.N2 | 108 ± 4.74 | (1.77 ± 0.03) × $10^6$ | (1.9 ± 0.08) × $10^{-4}$ |
| 4R.N3 | 68.6 ± 4.16 | (2.02 ± 0.03) × $10^6$ | (1.39 ± 0.08) × $10^{-4}$ |
| 4R.N4 | 99.7 ± 3.76 | (1.63 ± 0.02) × $10^6$ | (1.62 ± 0.06) × $10^{-4}$ |
| 4R.N5 | 74.8 ± 3.34 | (1.60 ± 0.02) × $10^6$ | (1.20 ± 0.05) × $10^{-4}$ |
| 4R.N6 | 70.5 ± 5.07 | (1.79 ± 0.03) × $10^6$ | (1.26 ± 0.09) × $10^{-4}$ |
| 4R.N7 | 43.1 ± 4.84 | (1.55 ± 0.02) × $10^6$ | (6.07 ± 0.74) × $10^{-5}$ |
| 4R.N8 | 80.2 ± 3.78 | (1.83 ± 0.02) × $10^6$ | (1.47 ± 0.07) × $10^{-4}$ |

Example 6: Evaluation of SEAP Activity Inhibition by IL-4-Dependent STAT6 Phosphorylation of Selected Anti-IL-4Rα Antibodies The biological activity of HEK-Blue-IL-4/IL-13 cells (Invivogen) can be compared by monitoring activation of cell signaling by IL-4 or IL-13 through colorimetric analysis. These cells were derived from stable cell lines obtained by transfecting the human STAT6 gene in order to provide a fully activated STAT6 pathway to HEK293 cells that sufficiently express the hIL-4 and hIL-13 receptors. In addition, these cells are transfected with the STAT6-inducible secreted embryonic alkaline phosphatase (SEAP) reporter genes. When hIL-4 or hIL-13 binds to the hIL-4 receptor or hIL-13 receptor expressed on the surface of HEK-Blue-IL-4/IL-13 cells, they activate Tyk2 and JAK1 and recruit and phosphorylate STAT6. Active phosphorylated STAT6 forms a dimer, moves to the nucleus, binds to the promoter of responsive genes, and induces the secretion of SEAP. The secreted SEAP causes a pink substrate, QUANTI-Blue, to turn purple. The degree of color development has a positive correlation with the amount of hIL-4 and hIL-13 that is present, and the content of hIL-4 and IL-13 can be quantified with reference to a standard. Therefore, these cells enable easy screening as to whether or not anti-IL-4/IL-4Rα antibodies or anti-IL-13/IL-13Rα1 antibodies block the IL-4 or IL-13 signaling pathways.

FIG. 3 shows the result of SEAP secretion of HEK-Blue IL-4/13 cells confirming the IL-4-signal-blocking effect of constructed anti-IL-4Rα antibodies compared to that of dupilumab analogues. Specifically, cells were seeded in an amount of 100 μl at a density of $2.5 \times 10^5$ cells/mL in a 96-well plate in a culture medium (DMEM supplemented with 4.5 g/L glucose (Gibco/Invitrogen), 10% heat-inactivated FBS (Gibco/Invitrogen)), 10 μg/mL blasticidin S, activated peptidyl nucleoside antibiotics (Invitrogen), 100 μg/mL Zeocin (trade name) and *streptomyces*). On the same day, 50 μl of 1,000 pM human IL-4 (Sino Biological) and 50 μl of an anti-IL-4Rα antibody solution previously diluted to 8, 40 nM or 2, 10 nM were added and then the 96-well plate was incubated at 37° C. and 5% $CO_2$ for 24 hours. To measure the secreted SEAP, 20 μl of each cell supernatant was added to a transparent 96-well plate and mixed with 180 μl of a QUANTI-Blue solution, and then the 96-well plate was allowed to react at 37° C. for 1 hour and 30 minutes, and the absorbance at 620 nm was analyzed with a Cytation™ 3 cell Imaging multi-mode reader.

The result of analysis showed that 4R.N3, 4R.N4, 4R.N6, 4R.N7, and 4R.N8 exhibited a lower IL-4-signal-blocking effect than the dupilumab analogue (FIG. 3).

Example 7: Analysis of Binding Specificity of Anti-IL-5Rα Humanized Antibodies

Since IL-5Rα is a cell membrane glycoprotein, the amino acid residue Asp1-Asn313 of the sequence of IL-5Rα represented by SEQ ID NO: 66, which is an extracellular domain, was introduced into an animal cell expression vector and expressed. The result was called "α". An anti-IL-5Rα humanized antibody, hu2B7, was derived through mouse immunization and humanization using the sIL-5Rα antigen. A yeast cell surface expression library was constructed based on hu2B7 to obtain 5R65 with increased affinity. Screening was performed again using a yeast cell surface expression library based on 5R65 to improve affinity. As a result, six anti-IL-5Rα humanized antibodies (5R65.7, 5R65.10, 5R65.14, 5R65.18, 5R65.39, 5R65.45) were derived. The selected clones may contain the heavy-chain and light-chain CDR sequences shown in Tables 6 and 8 below.

TABLE 6

| Heavy-chain variable region name | CDR1 sequence | CDR2 sequence |
|---|---|---|
| Kabat No. | 31 32 33 34 35 | 50 51 52 52a 53 54 55 56 57 58 59 60 61 62 63 64 65 |
| 5R65 | S Y W I N<br>SEQ ID No: 27 | H I Y P N K N E N Y Y N H K F K D<br>SEQ ID No: 28 |
| 5R65.7 | S Y W I N<br>SEQ ID No: 27 | H I Y P N K N E N Y Y N H K F K D<br>SEQ ID No: 28 |
| 5R65.10 | S Y W I N<br>SEQ ID No: 27 | H I Y P N K N E N Y Y N H K F K D<br>SEQ ID No: 28 |
| 5R65.14 | S Y W I N<br>SEQ ID No: 27 | H I Y P N K N E N Y Y N H K F K D<br>SEQ ID No: 28 |
| 5R65.18 | S Y W I N<br>SEQ ID No: 27 | H I Y P N K N E N Y Y N H K F K D<br>SEQ ID No: 28 |
| 5R65.39 | S Y W I N<br>SEQ ID No: 27 | H I Y P N K N E N Y Y N H K F K D<br>SEQ ID No: 28 |
| 5R65.45 | S Y W I N<br>SEQ ID No: 27 | H I Y P N K N E N Y Y N H K F K D<br>SEQ ID No: 28 |

| Heavy-chain variable region name | CDR3 sequence |
|---|---|
| Kabat No. | 95 96 97 98 99 100 100a 100b 100c 100d 100e 101 102 |
| 5R65 | D Y Y G R S Y Y Y A M D Y<br>SEQ ID No: 29 |
| 5R65.7 | E F Y G R Q Y Y Q A M D Y<br>SEQ ID No: 30 |
| 5R65.10 | E Y Y G R S Y Y A A M D Y<br>SEQ ID No: 31 |
| 5R65.14 | E H Y G R P Y Y N A M D Y<br>SEQ ID No: 32 |
| 5R65.18 | E Y Y G R T Y Y S A M D Y<br>SEQ ID No: 33 |
| 5R65.39 | E F Y G R S R Y S A M D Y<br>SEQ ID No: 34 |
| 5R65.45 | E Y Y G R S Y Y N A M D Y<br>SEQ ID No: 35 |

TABLE 7

| Heavy-chain variable region name | Sequence | SEQ ID NO: |
|---|---|---|
| 5R65 | QVQLVQSGAEVKKPGSSVKVSCKASGYTFTSYWINWVRQAPGQGLEWIGHIYPNKNENYYNHKFKD KATLTVDKSTNTAYMELSSLRSEDIAVYYCTRDYYGRSYYYAMDYWGOGTTLIVSS | SEQ ID No: 36 |
| 5R65.7 | QVQLVQSGAEVKKPGSSVKVSCKASGYTFTSYWINWVRQAPGQGLEWIGHIYPNKNENYYNHKFKD KATLTVDKSTNTAYMELSSLRSEDTAVYYCTREFYGRQYYQAMDYWGQGTTLTVSS | SEQ ID No: 37 |
| 5R65.10 | QVQLVQSGAEVKKPGSSVKVSCKASGYTFTSYWINWVRQAPGQGLEWIGHIYPNKNENYYNKKFKD KATLTVDKSTNTAYMELSSLRSEDTAVYYCTREYYGRSYYAAMDYWGQGTTLTVSS | SEQ ID No: 38 |
| 5R65.14 | QVQLVQSGAEVKKPGSSVKVSCKASGYTFTSYWINWVRQAPGQGLEWIGHIYPNKNENYYNHKFKD KATLTVDKSTNTAYMELSSLRSEDTAVYYCTREHYGRPYYNAMDYWGQGTTLTVSS | SEQ ID NO: 39 |
| 5R65.18 | QVQLVQSGAEVKKPGSSVKVSCKASGYTFTSYWINWVRQAPGQGLEWIGHIYPNKNENYYNHKFKD KATLIVDKSTNTAYMELSSLRSEDTAVYYCTREYYGRTYYSAMDYWGQGTTLTVSS | SEQ ID No: 40 |

TABLE 7-continued

| Heavy-chain variable region name | Sequence | SEQ ID NO: |
|---|---|---|
| 5R65.39 | QVQLVQSGAEVKKPGSSVKVSCKASGYTFTSYWINWVRQAPGQGLEWIGHIYPNKNENYYNHKFKD KATLTVDKSTNTAYMELSSLRSEDTAVYYCTREFYGRSRYSAMDYWGQGTTLTVSS | SEQ ID No: 41 |
| 5R65.45 | QVQLVQSGAEVKKPGSSVKVSCKASGYTFTSYWINWVRQAPGQGLEWIGHIYPNKNENYYNHKFKD KATLTVDKSTNTAYMELSSLRSEDTAVYYCTREYYGRSYYNAMDYWGQGTTLTVSS | SEQ ID No: 42 |

TABLE 8

| Light-chain variable region name | CDR1 sequence | CDR2 sequence | CDR3 sequence |
|---|---|---|---|
| Kabat No. | 24 25 26 27 28 29 30 31 32 33 34 | 50 51 52 53 54 55 56 | 89 90 91 92 93 94 95 97 97 |
| 5R65 | K A S Q N V G T A V A | W A S T R H T | Q Q F G R Y P Y T |
| | SEQ ID No: 43 | SEQ ID No: 44 | SEQ ID No: 45 |

TABLE 9

| Light-chsin variable region | Sequence | SEQ ID NO: |
|---|---|---|
| 5R65 | DIQMTQSPSTLSASVGDRVTITCKASQNVGTAVAWYQQKPGKAPKLLIYWASTRHTGVPDRF SGSGSGTDFTLTISSLQPDDFATYYCQQFGRYPYTFGSGTKVEVK | SEQ ID No: 46 |

The binding specificity of anti-IL-5Rα humanized antibodies was determined using indirect ELISA. A multi-antigen ELISA was performed using four structurally different antigenic double-stranded DNA (dsDNA), insulin, the macromolecule hemocyanin, and the membrane component, cardiolipin. Specifically, sIL-4Rα antigen protein (50 ng/well, Sinobio; 10402-H08H), sIL-5Rα antigen protein (50 ng/well, Sinobio; 10392-H08H), dsDNA (25 ng/well, D4522; Sigma), insulin (125 ng/well, 19278; Sigma), hemocyanin (125 ng/well, H8283; Sigma), and cardiolipin (1250 ng/well, C0563; Sigma) proteins were immobilized on a 96-well plate at room temperature for 1 hour, and blocked using 2% skim milk containing 0.1% PBST (0.1% Tween20, pH 7.4, 137 mM NaCl, 10 mM phosphate, 2.7 mM KCl) at room temperature for 1 hour. After discarding the solution and then washing the same three times with 0.1% PBST, the antibody was diluted to 100 nM, added to the blocked plate in an amount of 25 dal/well, and allowed to react at room temperature for 1 hour. After discarding the solution and washing the same three times with 0.1% PBST, an anti-human Fc-HRP antibody (1:8000) as a secondary antibody was added in an amount of 25 dal/well and reacted at room temperature for 1 hour. After discarding the solution and washing three times with PBST, a TMB solution was added in an amount of 25 dal/well, color development was induced at room temperature for 2 minutes, the reaction was stopped using $H_2SO_4$ (2N), and the absorbance at 450 nm was measured with an ELISA reader.

As can be seen from the results of FIG. 4A, the anti-IL-5Rα humanized antibodies (5R65, 5R65.7, 5R65.10, 5R65.14, 5R65.18, 5R65.39, 5R65.45) exhibited no binding ability to sIL-4Rα and 4 types of proteins, which indicated that they have binding specificity.

Example 8: Analysis of Binding Ability of Selected Anti-IL-5Rα Antibodies

In order to more quantitatively analyze binding ability to sIL-5Rα for selected anti-IL-5Rα antibodies (5R65.7, 5R65.10, 5R65.14, 5R65.18, 5R65.39, 5R65.45), the binding ability was measured according to the protocol suggested by the manufacturer using an Octet QK$^e$ (ForteBio, USA) system. Specifically, lx kinetic buffer was prepared by diluting 10× kinetic buffer (ForteBio, 18-1105) in PBS. The antibody was diluted to a concentration of 1 μg/ml in 1× kinetic buffer, the purified sIL-5Rα was sequentially diluted at concentrations of 400, 200, 100, 12.5, 6.25 and 0 nM in 1× kinetic buffer, and 200 μl of each dilution was injected into an opaque 96-well plate through which light does not pass. Antigen affinity of antibodies was analyzed through the variation in refractive index occurring when the antibody bound to the antigen was detached therefrom while the AHC (anti-human IgG Fc capture) sensor chip moved in the order of 1× kinetic buffer, antibody dilution solution, 1× kinetic buffer, antigen dilution solution, and 1× kinetic buffer. Affinity was calculated with Octet Data Analysis software 11.0 in a 1:1 binding model. The results are shown in FIG. 4B.

Table 10 shows the results of analysis of affinity of selected anti-IL-5Rα humanized antibodies to sIL-5Rα using the Octet QK$^e$ system.

TABLE 10

| | $K_D$(nM) | $k_{on}$(1/Ms) | $k_{off}$(1/s) |
|---|---|---|---|
| 5R65 | 14.5 ± 0.29 | (2.27 ± 0.03) × $10^4$ | (3.29 ± 0.05) × $10^{-4}$ |
| 5R65.7 | 4.64 ± 0.23 | (3.17 ± 0.05) × $10^4$ | (1.47 ± 0.07) × $10^{-4}$ |
| 5R65.10 | 8.25 ± 0.40 | (2.44 ± 0.05) × $10^4$ | (2.01 ± 0.09) × $10^{-4}$ |
| 5R65.14 | 8.64 ± 0.35 | (2.30 ± 0.04) × $10^4$ | (1.99 ± 0.07) × $10^{-4}$ |
| 5R65.18 | 5.95 ± 0.27 | (2.24 ± 0.03) × $10^4$ | (1.33 ± 0.06) × $10^{-4}$ |
| 5R65.39 | 6.13 ± 0.32 | (2.80 ± 0.05) × $10^4$ | (1.71 ± 0.08) × $10^{-4}$ |
| 5R65.45 | 7.26 ± 0.36 | (2.49 ± 0.05) × $10^4$ | (1.81 ± 0.08) × $10^{-4}$ |

Example 9: Comparison in Inhibition of IL-5-Dependent Proliferation in TF-1/IL-5Rα Cell Lines Between Anti-IL-5Rα Humanized Antibodies The ability of anti-IL-5Rα antibodies to inhibit IL-5-dependent cell proliferation was evaluated using TF-1 cells stably expressing IL-5Rα (TF-1/IL-5Rα cells). The variable regions (VH, VL) of benralizumab (DrugBank accession number; DB12023) as a control and the selected antibody were introduced into the pcDNA3.4 vector encoding the light-chains (CH1, CH2, CH3) and heavy-chain (CL) of IgG1. The benralizumab was called "a benralizumab analogue".

TF-1/IL-5Rα cells were seeded in 100 μl at a density of $2\times10^4$ in a 96-well plate. On the same day, 50 μl of 320 pM IL-5 and 50 μl of an anti-IL-5Rα humanized antibody solution previously diluted 2-fold at 128 nM were added thereto, and the 96-well plate was incubated at 37° C. and 5% $CO_2$ for 40 hours. In order to measure the proliferation capacity of cells, 100 μl of cell suspension was collected from each well, 100 μl of CellTiter-Glo (CellTiter-Glo® manufactured by Promega) was added thereto and reacted at room temperature for 20 minutes and analyzed with a Cytation™ 3 cell imaging multi-mode reader (FIG. 5A). As a result, the benralizumab analogue had an absolute $IC_{50}$ (Abs $IC_{50}$) of 1.99 nM, and the selected anti-IL-5Rα antibodies (5R65.7, 5R65.10, 5R65.14, 5R65.18, 5R65.39, 5R65.45) had an absolute (abs) $IC_{50}$ of 0.57 nM to 1.34 nM, which indicates that the antibodies have improved ability to inhibit IL-5-dependent proliferation in the TF-1/IL-5Rα cell line compared to the benralizumab analogue. In particular, 5R65.7 exhibited the strongest proliferation inhibitory activity (FIG. 5A).

Example 10: Evaluation of the Ability of Anti-IL-5Rα Humanized Antibodies with Improved Affinity to Inhibit the Proliferation of Human Eosinophils Derived from Healthy Donors and Patients with Severe Asthma Eosinophils are important inflammatory cells involved in allergic/inflammatory diseases and are representative cells expressing IL-5Rα. Since IL-5 is known to be involved in the proliferation of eosinophils, eosinophils were isolated and purified from human-derived peripheral blood and then the ability of anti-IL-5Rα antibodies to inhibit eosinophil proliferation was evaluated.

Specifically, 20 ml of Ficoll-Paque solution (GE Healthcare, 17-5442-03) was dispensed into each 50 ml polypropylene centrifuge tube, and 20 ml of the heparinized patient blood was layered on each tube. The result was centrifuged at 879×g at room temperature for 25 minutes to separate and collect the lowest layer. 2% dextran solution was dispensed to separate the red blood cells (lower layer) and the granulocyte layer (upper layer) from each other, and the granulocyte layer was recovered and 27 ml of sterilized water and 3 ml of 10×HBSS were added thereto to remove red blood cells mixed therewith. Concentrated granulocytes (eosinophils and neutrophils) from which red blood cells were removed were separated and collected by centrifugation at 300×g and 4° C. for 10 minutes. Finally, only eosinophils were purified from granulocytes using a commercially available eosinophil cell isolation kit (Miltenyi Biotec; 130-092-010) according to the manufacturer's protocol.

Eosinophils were seeded at $5\times10^4$ cells/well into a 96-well cell culture plate, human IL-5 having a final concentration of 100 pM was added thereto, and anti-IL-5Rα antibodies having a final concentration of 5 nM, 20 nM, and 100 nM, were each added thereto. Each antibody was cultured in 2 to 3 wells and the capacity of each well was 200 μl. After culturing for 2 days at 37° C. in a $CO_2$ incubator, 100 μl of cell suspension was recovered from each well, and 100 μl of CellTiter-Glo® Promega sample was added to the culture medium and incubated at room temperature for 20 minutes. The proliferative ability of eosinophils was analyzed by measuring luminescence with a microplate meter.

As can be seen from FIG. 5B, 5R65.7 exhibited the strongest eosinophil growth inhibitory activity, which was higher than that of benralizumab analogues.

Example 11: Evaluation of Ability of Anti-IL-5Rα Humanized Antibodies to Induce Antibody-Dependent Cytotoxicity of Human Eosinophils from Healthy Donors and Severe Asthma Patients FDA-approved benralizumab has an afucosylated Fc and thus has a higher affinity for FcγRIIIa expressed in NK cells than IgG1 Fc, and exhibits higher ADCC activity. Due to the high ADCC activity thereof, benralizumab can effectively eliminate eosinophils in asthmatic patients. Since the present inventors do not have facilities for producing afucosylated antibodies, they compared the activity of benralizumab analogues having an IgG1 Fc with anti-IL-5Rα humanized antibodies (5R65, 5R65.7) also having the same IgG1 Fc.

Specifically, 20 ml of Ficoll-Paque solution (GE Healthcare, 17-5442-03) was dispensed into each 50 ml polypropylene centrifugal tube, and 20 ml of heparinized patient blood was layered on each tube. The result was centrifuged at 879×g at room temperature for 25 minutes to separate and recover the buffy coat layer for NK cell isolation and the lowermost layer for eosinophil isolation. Isolated primary NK cells and eosinophils were used as effector and target cells at a ratio of 5:1, respectively. Eosinophils and primary NK cells are seeded at densities of $5\times10^4$ cells/well and $2.5\times10^3$ cells/well, respectively, into a 96-well cell culture plate, and human IL-5 having a final concentration of 100 pM was added thereto. In addition, various anti-IL-5Rα antibodies with improved affinities having a final concentration of 1 μM were added thereto. Each antibody was cultured in two wells and the final volume of each well was adjusted to 200 μl. The cells were incubated in a $CO_2$ incubator at 37° C. for 20 hours, and 2 hours before collection of the cell suspension, 20 μl of a lysis solution is added to a sample for maximum lactate dehydrogenase (LDH) efflux. After the completion of culture, 50 μl of the cell suspension was collected from each well, and then 50 μl of CytoTox96® Reagent (manufactured by Promega) was added thereto and the result was incubated at room temperature for 30 minutes. After adding 50 μl of the reaction stop solution, the absorbance was measured using a microplate meter to analyze the antibody-dependent cytotoxicity inducing ability. Y and X axes represent % maximal cytotoxicity and antibody concentration, respectively.

$$\text{Cytotoxicity } (\%)=(A-B)/(C-B)\times 100$$

A: Release value upon antibody treatment

B: Spontaneous cell release value

C: Maximum cell release value

The result of the analysis showed that benralizumab having an IgG1 Fc hardly induced antibody-dependent cytotoxicity, as in the previous report (Kolbeck et al., 2010). Antibody-dependent cytotoxicity induction of 5R65 and 5R65.7 in eosinophils derived from healthy donors and patients with severe asthma was higher than that of benralizumab analogues, and 5R65.7 exhibited the strongest induction ability. This can be confirmed by a quantified graph (FIG. 5C).

Example 12: Construction Design of Bispecific (IL-4Rα×IL-5Rα) Antibody that Simultaneously Binds to IL-4Rα and IL-5Rα

It is important to determine affinity for each antigen, valency, geometry of antigen-binding sites, and format and architecture of bispecific antibodies in the development of bispecific antibodies that bind to two or more antigens at the same time. In addition, since mutations or linkers are introduced in order to construct bispecific antibodies, bispecific antibodies have a drawback of inferior physical properties to monoclonal antibodies. Therefore, the present inventors prepared various formats of IL-4Rα×IL-5Rα bispecific antibodies to determine how the biochemical/biological efficacy changes and to select the most effective IL-4Rα×IL-5Rα bispecific antibodies.

1) a format similar to IgG, 2) IgG single chain Fv (IgG-scFv), and 3) dual variable domain IgG (DVD-IgG) as representatives of the various IL-4Rα×IL-5Rα bispecific antibody formats, were constructed by combination of the position of the target antibody, linker, and the like. First, the format similar to IgG has monovalent binding to each antigen. To construct this format, two light-chains (VL1, VL2) and two heavy-chains (VH1, VHf2) must form a complementary binding pair. Therefore, an IL-4Rα×IL-5Rα bispecific antibody in single-chain (scIgG) format in which complementary light and heavy-chains are bound by a linker or an IL-4Rα×IL-5Rα bispecific antibody in a bispecific IgG (BsIgG) format in which electrostatic interaction was introduced into the light-chain constant region (CL) and heavy-chain constant region (CH1) was constructed. In order to construct the format similar to IgG, mutations were introduced into the CH3 domain to form a heterodimer Fc (FIG. 6).

Next, there is a method of constructing a bispecific antibody by additionally linking an antibody variable region to a monoclonal antibody. In the present invention, the antibody variable regions (VH, VL) were linked via a linker composed of Gly-Ser to form a single chain Fv (scFv), and the single chain Fv (scFv) was connected to the C-terminus of IgG to construct an IgG-scFv format. The IL-4Rα×IL-5Rα bispecific antibody in the IgG-scFv format has bivalent binding to each antigen because it further connects the variable region. However, the antigen-binding ability of antibody variable regions linked by linkers may be reduced. The stability of the scFv can be increased by introducing a disulfide bond into the contact surface between the VL and VH connected to the scFv. In addition, as can be seen from the schematic diagram of FIG. 6, the IL-4Rα×IL-5Rα bispecific antibody in the IgG-scFv format has a geometry of antigen-binding sites in which binding to respective antigens occurs in opposite directions.

In order to compare the efficacy of bispecific antibodies based on the geometry of the antigen-binding sites, dual variable domain IgG (DVD-Ig) having binding ability to each antigen in juxtaposition was additionally constructed. The DVD-IgG-format IL-4Rα×IL-5Rα bispecific antibody includes a format in which heavy-chain and light-chain variable regions of the antibody binding to IL-4Rα or the antibody binding to IL-5Rα are disposed in juxtaposition at the N-terminus of the IgG including the heavy-chain variable region and the light-chain variable region of the antibody binding to IL-4Rα or the antibody binding to IL-5Rα. The IL-4Rα×IL-5Rα bispecific antibody in the DVD-IgG format also has bivalent binding to each antigen. As can be seen from the schematic diagram of FIG. 6, since the first variable region pair covers the second variable region pair, the antigen-binding ability of the second variable region pair may be reduced.

Example 13: Construction of IL-4Rα×IL-5Rα Bispecific Antibodies of scIgG and BsIgG Formats that Simultaneously Bind to IL-4Rα and IL-5Rα

First, an IL-4Rα×IL-5Rα bispecific antibody having monovalent binding to IL-4Rα and IL-5Rα was constructed. As shown in the schematic diagram of FIG. 7, the format in which the light-chain and the heavy-chain are connected by a linker was named "scIgG" (FIG. 7A), and the format in which a mutation inducing electrostatic interaction between the light-chain constant region (CL) and the heavy-chain constant region 1 (CH1) were introduced was named "BsIgG" (FIG. 7C). An EW-RVT mutation (Kim et al., 2018) was introduced into heavy-chain constant region 3 (CH3) of both scIgG and BsIgG, so that heterodimeric heavy-chain constant region (Heterodimeric Fc) pairs could be formed. An IL-4Rα×IL-5Rα bispecific antibody having monovalent binding was constructed by fusing antigen binding sites capable of binding different antigens to the N-terminus of heterodimer Fc.

Specifically, the IL-4Rα×IL-5Rα bispecific antibodies were introduced into a pcDNA3.4 vector encoding the heavy-chains (CH1, CH2, CH3) and light-chain (CL) of IgG1. For scIgG, the heavy and light-chain variable regions of the anti-IL-4Rα antibody were linked via a linker consisting of 60 small amino acid residues, and then the heavy-chain variable regions in which K360E and K409W (EU numbering) mutations were introduced were linked to CH3 (FIG. 7B). Similarly, the heavy and light-chain variable regions of the anti-IL-5Rα antibody were linked with a linker consisting of 60 amino acids, and then the heavy-chain variable regions in which Q347R, D399V, and F405T (EU numbering) mutations were introduced were linked to CH3 (FIG. 7B). For BsIgG, a V133E mutation was introduced into CL of the light-chain, encoding an anti-IL-4Rα antibody, and a S183K mutation was introduced into the CH1 of the heavy-chain to provide electrostatic interaction, and K360E and K409W mutations were introduced into CH3 of the heavy-chain. In addition, the V133K mutation was introduced into the light-chain constant region, which can encode anti-IL-5Rα antibody, and the S183E mutation was introduced into the heavy-chain constant region 1 (CH1) to provide electrostatic interaction (Dillon et al., 2017), and Q347R, D399V, and F405T mutations were introduced in CH3 of the heavy chain (FIG. 7D).

Tables 11 and 12 show the amino acid sequences of IL-4Rα×IL-5Rα bispecific antibodies in scIgG and BsIgG formats, respectively. The anti-IL-4Rα antibody light-chain variable region of SEQ ID NO: 21 includes sequences of SEQ ID NOS: 22 to 26. The anti-IL-4Rα antibody heavy-chain variable region of SEQ ID NO: 9 includes sequences of SEQ ID NOS: 10 to 14. The anti-IL-5Rα antibody heavy-chain variable region of SEQ ID NO: 36 includes sequences of SEQ ID NOS: 37 to 42.

TABLE 11

| | sclgG | sclgG | |
|---|---|---|---|
| and-IL-4Rα VL (SEQ ID No: 21) | QSVLTQPPSASGTPGQRVTISCSGSPLFPDSGSFNWYQQLPGTAPKLLIYADSHRPSGVPDRFSGSKSGTSASLAISGLRSEDEADYYCGTWDYSLSGYVLGGGTKLTVLG | anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFTLTISSLQPDDFATYYCQQFGRYPYTFGSGTKVEVK |
| CL (SEQ ID No: 47) | RTVAAPSVFIFPPSDEQLKSGTASVVCLLNNFYPREAKVQWKVDNALQSGNSQESVTEQDSKDSTYSLSSTLTLSKADYEKHAVYACEVTHQGLSSPVTKSFNRGEC | CL (SEQ ID No: 47) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Linker (60 amino acid) (SEQ ID No: 48) | GSSGSGSGSTGTSSSGTGTSAGTTGTSASTSGSGSGGGGGSGGGGSAGGTATAGASSGS | Linker (60 amino acid) (SEQ ID No; 48) | GSSGSGSGSTGTSSSGTGTSAGTTGTSASTSGSGSGGGGGSGGGGSAGGTATAGASSGS |
| anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISRDNSKNTLYLQMNSLRAEDTAVYYCARVHRAFDYWGQGTLVTVSS | anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTVDKSTNTAYMELSSLRSEDTAVYYCTRDYYGRSYYYAMDYWGQGTTLTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | CH1 (SEQ ID No: 49) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| Hinge (SEQ ID No: 50) | EPKSCDKTHTCPPCP | Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | CH2 (SEQ ID No: 81) | APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK |
| CH3A (SEQ ID No: 52) | GQPREPQVYTLPPSRDELTENQVSLTCLVKGFYPSDIAVEWESNGQPENNYKTTPPVLDSDGSFFLYSWLTVDKSRWQQGNVFSCSVMHEALHNHYTQKSLSLSPGK | CH3B (SEQ ID No: 53) | GQPREPRVYTLPPSRDELTKNQVSLTCLVKGFYPSDIAVEWESNGQPENNYKTTPPVLVSDGSFTLYSKLTVDKSRWQQGNVFSCSVMHEALHNHYTQKSLSLSPGK |

TABLE 12

| | BslgG Light-chain | | Bslg Light-chain |
|---|---|---|---|
| anti-IL-4Rα VL (SEQ ID No: 21) | QSVLTOPPSASGTPGQRVTISCSGSPLFPDSGSFNWYQQLPGTAPKLLIYADSHRPSGVPDRFSGSKSGTSASLAISGLRSEDEADYYCGTWDYSLSGYVLGGGTKLTVLG | anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFTLTISSLQPDDFATYYCQQFGRYPYTFGSGTKVEVK |
| CL (V133E) (SEQ ID No: 54) | RTVAAPSVFIFPPSDEQLKSGTASVECLLNNFYPREAKVQWKVDNALQSGNSQESVTEQDSKDSTYSLSSTLTLSKADYEKHKVYACEVTHQGLSSPVTKSFNRGEC | CL (V133K) (SEQ ID No: 55) | RTVAAPSVFIFPPSDEQLKSGTASVKCLLNNFYPREAKVQWKVDNALQSGNSQESVTEQDSKDSTYSLSSTLTLSKADYEKHAVYACEVTHQGLSSPVTKSFNRGEC |
| | BslgG Heavy-chain | | BslgG Heavy-chain |
| Anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISRDNSKNTLYLQMNSLRAEDTAVYYCARVHRAFDYWGQGTLVTVSS | anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTVDKSTNTAYMELSSLRSEDTAVYYCTRDYYGRSYYYAMDYWGQGTTLTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | CH1 (SEQ ID No: 49) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |

TABLE 12-continued

| | | | |
|---|---|---|---|
| Hinge (SEQ ID No: 50) | EPKSCDKTHTCPPCP | Hinge (SEQ ID No: 50) | EPKSCDKTHTCPPCP |
| CH2 (SEQ ID No: 51) | APELLGGPSVFLFPPKPKDTLMISRTPEVTCVVVDV SHEDPEVKFNWYVDGVEVHNAKTKPREEQYNSTY RVVSVLTVLHQDWLNGKEYKCKVSNKALPAPIEKT ISKAK | CH2 (SEQ ID No: 51) | APELLGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALPAPI EKTISKAK |
| CH3A (SEQ ID No: 52) | GQPREPQVYTLPPSRDELTENQVSLTCLVKGFYPS DIAVEWESNGQPENNYKTTPPVLDSDGSFFLYSWL TVDKSRWQQGNVFSCSVMHEALHNHYTQKSLSLS PGK | CH3B (SEQ ID No: 53) | GQPREPRVYTLPPSRDELTKNQVSLTCLVKGFYP SDIAVEWESNGQPENNYKTTPPVLVSDGSFTLYS KLTVDKSRWQQGNVFSCSVMHEALHNHYTQKSLS LSPGK |

Example 14: Expression and Purification of IL-4Rα×IL-5Rα Bispecific Antibodies in scIgG and BsIgG Formats that Simultaneously Bind to IL-4Rα and IL-5Rα

To express and purify the IL-4Rα×IL-5Rα bispecific antibody, HEK293F (Invitrogen) cells were transiently transfected. For transfection of 200 mL of the cells in a shake flask (Corning), HEK293F cells were seeded at a density of $2.0\times10^6$ cells/ml and incubated at 120 rpm, 8% $CO_2$ and 37° C. A total of 250 μg of light- and heavy-chains at a ratio of 1:1 or 1:1:1:1 in HEK293F cells was diluted in 5 ml serum-free Freestyle 293 expression medium (Invitrogen), filtered, mixed with 5 ml of a medium diluted with 750 μg of polyethylenimine (PEI) and then was reacted for 10 minutes at room temperature. Then, the reacted mixed medium was injected into the 190 ml previously seeded cells, followed by incubation at 120 rpm and 8% $CO_2$ and further incubation for 6 days. Proteins were purified from the cell incubation supernatant collected with reference to standard protocols. The antibody was applied to a protein A Sepharose column and washed with PBS (pH 7.4). After the antibody was eluted at pH 3.0 using 0.1 M glycine and 0.5 M NaCl buffer, the sample was immediately neutralized using 1 M Tris buffer. The eluted protein was concentrated using a Vivaspin 30,000 MWCO (Sartorius) centrifugal concentrator after buffer exchange with storage buffer (25 mM Tris-HCl, 150 mM NaCl, 2 mM KCl, 1 mM EDTA, pH 7.2). The purified protein was measured for absorbance at a wavelength of 562 nm using a solution in the BCA protein assay kit (Thermo), and the amount thereof was quantified according to the standard curve. As a result, 4.02 mg of scIgG and 3.66 mg of BsIgG were purified.

Example 15: SDS-PAGE and SEC Analysis of IL-4Rα×IL-5Rα Bispecific Antibodies of scIgG and BsIgG Formats that Simultaneously Bind to IL-4Rα and IL-5Rα

3 μg of the IL-4Rα×IL-5Rα bispecific antibody of scIgG format purified in Example 14 was analyzed on SDS-PAGE under 12% non-reducing conditions (FIG. 8A). scIgG is formed as a heterodimer of two units of light-chain-linker-heavy-chain. Each monomer has a molecular weight of about 78 kDa and scIgG has a molecular weight of about 156 kDa. The portion indicated by the arrow in FIG. 6A is scIgG, and a band expected to correspond to an aggregate and a band expected to be a 78 kDa monomer were observed in the upper portion. In addition, scIgG was analyzed by size-exclusion chromatography (SEC). Specifically, 30 μg of protein was injected into a Superdex 200 Increase 10/300 GL column using PBS (12 mM phosphate, 0.5 M NaCl, 2.7 mM KCl, pH 7.4) with high salt concentration as a running buffer and the elution of the protein at a wavelength of 280 nm was determined. Elution times of β-amylase (200 kDa, sigma; A8781) and Herceptin (150 kDa) were compared to compare the molar mass of the proteins. Similar to the result of SDS-PAGE, scIgG was observed between 200 kDa and 150 kDa, and peaks expected to correspond to the aggregate and monomer were also observed (FIG. 8B).

Likewise, 3 μg of the IL-4Rα×IL-5Rα bispecific antibody of the BsIgG format purified in Example 14 was analyzed on SDS-PAGE under 12% non-reducing conditions (FIG. 8C). BsIgG consists of two light-chains and two heavy-chains. The light-chain monomer has a molecular weight of about 25 kDa and the heavy-chain monomer has a molecular weight of about 50 kDa. The portion indicated by the arrow in FIG. 6C is BsIgG and a band expected to correspond to an aggregate was observed in the upper portion. BsIgG was also analyzed by size exclusion chromatography. Specifically, 30 μg of protein was injected into a Superdex 200 Increase 10/300 GL column using PBS (12 mM Phosphate, 0.5 M NaCl, 2.7 mM KCl, pH 7.4) with high salt concentration as a running buffer. The elution of the protein at a wavelength of 280 nm was determined. Elution times of β-Amylase (200 kDa, sigma; A8781) and Herceptin (150 kDa) were compared to compare the molar mass of the proteins. BsIgG was observed around 150 kDa, and a peak expected to correspond to an aggregate was somewhat observed (FIG. 8D). The result showed that among the bispecific antibody having monovalent binding ability to IL-4Rα×IL-5Rα, the BsIgG format had better physical properties.

Example 16: Construction of IL-4Rα×IL-5Rα Bispecific Antibodies of 4R-IgG-5R-$_{HL}$scFv and 4R-IgG-5R-$_{LH}$scFv Formats that Simultaneously Bind to IL-4Rα and IL-5Rα

Subsequently, an IL-4Rα×IL-5Rα bispecific antibody having bivalent binding to IL-4Rα and IL-5Rα antigens was constructed in an IgG-scFv format. scFv is a building block that is widely used to construct bispecific antibodies. The scFv may have different antigen-binding ability or physical properties depending on the order in which variable regions are connected, more specifically, heavy-chain (VH)-light-chain (VL) or light-chain (VL)-heavy-chain (VH). In addition, the stability of scFv can be increased by introducing a disulfide bond into the interface between VL and VH. In particular, it was reported that the residue 44 of VH and residue 100 of VL are far from CDRs, thus having no effect on antigen-binding ability, and the distance between the two residues is close to 5.36 Å, thus reducing formation of aggregates when mutation is introduced into Cys (Zhao et al., 2010).

As shown in the schematic diagram of FIG. 9, the format in which the variable region of anti-IL-5Rα was linked in the order of VH-VL to the C-terminus of the anti-IL-4Rα antibody was named "4R-IgG-5R-$_{HL}$scFv" (FIG. 9A), and the format in which the variable region of anti-IL-5Rα was linked in the order of VH-VL to the C-terminus of the anti-IL-4Rα antibody was named "4R-IgG-5R-$_{LH}$scFv" (FIG. 9C). The scFv was connected to the C-terminus of the anti-IL-4Rα antibody via an LGGGGSGGGGSGGGGS (16 amino acid residues) linker, and a GGGGSGGGGSGGGGSGGGGS (20 amino acid residues) linker was connected between VH-VL or VL-VH. The IL-4Rα×IL-5Rα bispecific antibodies were introduced into the pcDNA3.4 vector encoding the heavy-chains (CH1, CH2, CH3) and light-chain (CL) of IgG1. FIG. 9B is a schematic diagram of a vector encoding the light- and heavy-chains of 4R-IgG-5R-$_{HL}$scFv, and FIG. 9D is a schematic diagram of a vector encoding the light- and heavy-chains of 4R-IgG-5R-$_{LH}$scFv. In the variable region of anti-IL-5Rα, glycine residue 44 of VH was mutated to cysteine and serine residue 100 of VL was mutated to cysteine.

Tables 13 and 14 respectively show the amino acid sequences of 4R-IgG-5R-$_{HL}$scFv and 4R-IgG-5R-$_{LH}$scFv. The anti-IL-4Rα antibody light-chain variable region of SEQ ID NO: 21 includes SEQ ID NOS: 22 to 26. The anti-IL-4Rα antibody heavy-chain variable region of SEQ ID NO: 9 includes SEQ ID NOS: 10 to 14. The anti-IL-5Rα antibody heavy-chain variable region of SEQ ID NO: 58 includes a cysteine mutation introduced at residue 44 in SEQ ID NOS: 37 to 42.

TABLE 13

| | |
|---|---|
| **4R-IgG-5R$_{HL}$-scFv light-chain** | |
| anti-IL-4Rα VL (SEQ ID No: 21) | QSVLTQPPSASGTPGQRVTISCSGSPLFPDSGSFNWYQQLPGTAPKLLIYADSHRPSGVPDRFSQSKSGTSA SLAISGLRSEDEADYYCGTWDYSLSGYVLGGGTKLTVLG |
| CL (SEQ ID NO: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| **4R-1gG-5R$_{HL}$-scFv heavy-chain** | |
| anti-IL-4Rα VH (SEQ ID No: 9) | EVQLLESGGGLVQPGGSLALSCAASGFTFSRHAMAWVRQAPGKGLEWVSAITSSGRSIYYADSVKGRFTISR DNSKNTLYLQMNSLRAEDTAVYYCARVHRAFDYWGQGTLVTVSS |
| CH1 (SEQ ID No: 49) | ASTKGPSVFPLAPSSKSTSGGTAALGCLVKDYFPEPVTVSWMSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |
| Linker (16 amino acid) (SEQ ID No: 57) | LGGGGSGGGGSGGGGS |
| anti-IL-5Rα VH (G44C) (SEQ ID No: 58) | QVQLVQSGAEVKKPGSSVKVSCKASGYTFTSYWINWVRQAPGQCLEWIGHIYPNKNENYYNHKFKDKATLTV DKSTNTAYMELSSLRSEDTAVYYCTRDYYGRSYYYAMDYWGQGTTLTVSS |
| Linker (20 amino acid) (SEQ ID No: 59) | GGGGSGGGGSGGGGSGGGGS |
| anti-IL-5Rα VL (S100C) (SEQ ID No: 60) | DIQMTQSPSTLSASVGDRVTITCKASQNVGTAVAWYQQKPGKAPKLLIYWASTRHTGVPDRFSGCGSGTDFT LTISSLQPDDFATYYCQQFGRYPYTFGSGTKVEVK |

TABLE 14

| | |
|---|---|
| **4R-IgG-5R$_{LH}$-scFv light-chain** | |
| anti-IL-4Rα VL (SEQ ID No: 21) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGGGTKLTVLG |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| **4R-IgG-5R$_{LH}$-scFv heavy-chain** | |
| anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISR DNSKNTLYLQMNSLRAEDTAVYYCARVHRAFDYWGQGTLVTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |

TABLE 14-continued

| | |
|---|---|
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |
| Linker (16 amino acid) (SEQ ID No: 57) | LGGGGGGGGGSGGGGS |
| anti-IL-5Rα VL (S100C) (SEQ ID No: 60) | DIQMTQSPSTLSASVGDRVTITCKASQNVGTAVAWYQQKPGKAPKLLIYWASTRHTGVPDRFSGCGSGTDFT LTISSLQPDDFATYYCQQFGRYPYTFGSGTKVEVK |
| Linker (20 amino acid) (SEQ ID No: 59) | GGGGSGGGGSGGGGSGGQGS |
| anti-IL-5Rα VH (G44C) (SEQ ID No: 58) | QVQLVQSGAEVKKPGSSVKVSCKASGYTFTSYWINWVRQAPGQCLEWIGHIYPNKNENYYNHKFKDKATLTV DKSTNTAYMELSSLRSEDTAVYYCTRDYYGRSYYYAMDYWGQGTTLTVSS |

Example 17: Expression and Purification of IL-4Rα×IL-5Rα Bispecific Antibodies of 4R-IgG-5R-$_{HL}$scFv and 4R-IgG-5R-$_{LH}$scFv Formats that Simultaneously Bind to IL-4Rα and IL-5Rα

To express and purify the IL-4Rα×IL-5Rα bispecific antibody, HEK293F (Invitrogen) cells were transiently transfected. For transfection of 200 mL of the cells in a shake flask (Corning), HEK293F cells were seeded at a density of $2.0\times10^6$ cells/ml in 190 mL of a medium and incubated at 120 rpm, 8% $CO_2$ and 37° C. A total of 250 μg of light- and heavy-chains at a ratio of 1:1 in HEK293F cells was diluted in 5 ml serum-free Freestyle 293 expression medium (Invitrogen), filtered, mixed with 5 ml of a medium diluted with 750 μg of polyethylenimine (PEI) and then was reacted for 10 minutes at room temperature. Then, the reacted mixed medium was injected into the 190 ml previously seeded cells, followed by incubation at 120 rpm and 8% $CO_2$ and further incubation for 6 days. Proteins were purified from the cell incubation supernatant collected with reference to standard protocols. The antibody was applied to a protein A Sepharose column and washed with PBS (pH 7.4). After the antibody was eluted at pH 3.0 using 0.1 M glycine and 0.5 M NaCl buffer, the sample was immediately neutralized using 1 M Tris buffer. The eluted protein was concentrated using a Vivaspin 30,000 MWCO (Sartorius) centrifugal concentrator after buffer exchange with storage buffer (25 mM Tris-HCl, 150 mM NaCl, 2 mM KCl, 1 mM EDTA, pH 7.2). The purified protein was measured for absorbance at a wavelength of 562 nm using a solution in the BCA protein assay kit (Thermo), and the amount thereof was quantified according to the standard curve. As a result, 90 ug of 4R-IgG-5R-$_{HL}$scFv and 94 ug of 4R-IgG-5R-$_{LH}$scFv were purified.

Example 18: SDS-PAGE and SEC Analysis of IL-4Rα×IL-5Rα Bispecific Antibodies of 4R-IgG-5R-$_{HL}$scFv and 4R-IgG-5R-$_{LH}$scFv Formats that Simultaneously Bind to IL-4Rα and IL-5Rα

3 μg of the 4R-IgG-5R-$_{HL}$scFv bispecific antibody purified in Example 17 was analyzed through SDS-PAGE under 12% non-reducing conditions (FIG. 10A). 4R-IgG-5R-$_{HL}$scFv has two light-chains of about 25 kDa and two units of heavy-chain-linker-scFv of about 77 kDa, and thus has a total molar mass of 204 kDa. The portion indicated by the arrow in FIG. 8 is 4R-IgG-5R-$_{HL}$scFV, and a band expected to correspond to an aggregate was observed in the upper portion. In addition, 4R-IgG-5R-$_{HL}$scFV was analyzed by size-exclusion chromatography (SEC). Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer and the elution of the protein at a wavelength of 280 nm was determined. Elution times of β-amylase (200 kDa, sigma; A8781) and Herceptin (150 kDa) were compared to compare the molar mass of the proteins. Similar to the result of SDS-PAGE, 4R-IgG-5R-$_{HL}$scFV was observed at about 150 kDa, and peaks expected to correspond to the aggregate and EDTA contained in the storage buffer were also observed (FIG. 10B).

Likewise, 3 μg of the 4R-IgG-5R-$_{LH}$scFV bispecific antibody purified in Example 17 was analyzed through SDS-PAGE under 12% non-reducing conditions (FIG. 10C). 4R-IgG-5R-$_{LH}$scFV has two light-chains of about 25 kDa and two units of heavy-chain-linker-scFv of about 77 kDa, and thus has a total molar mass of 204 kDa. The portion indicated by the arrow in FIG. 8C is 4R-IgG-5R-$_{LH}$scFV and a band expected to correspond to an aggregate was observed in the upper portion. 4R-IgG-5R-$_{LH}$scFV was also analyzed by size exclusion chromatography. Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer. The elution of the protein at a wavelength of 280 nm was determined. Elution times of β-Amylase (200 kDa, sigma; A8781) and Herceptin (150 kDa) were compared to compare the molar mass of the proteins. 4R-IgG-5R-$_{LH}$scFV was observed around 200 kDa, a peak expected to correspond to an aggregate was observed in an amount of less than 4R-IgG-5R-$_{HL}$scFv, and a tailing peak was also observed due to poor formation of 4R-IgG-5R-$_{LH}$scFv. A peak corresponding to EDTA contained in the storage buffer was also observed (FIG. 10B). The result showed that the 4R-IgG-5R-$_{HL}$scFv and 4R-IgG-5R-$_{LH}$scFv had poor expression and physical properties.

Example 19: Construction of IL-4Rα×IL-5Rα Bispecific Antibodies of 5R-IgG-4R-$_{HL}$scFv and 5R-IgG-4R-$_{LH}$scFv Formats that Simultaneously Bind to IL-4Rα and IL-5Rα

Subsequently, an IL-4Rα×IL-5Rα bispecific antibody having bivalent binding to IL-4Rα and IL-5Rα antigens was constructed in an IgG-scFv format. Contrary to Example 16, the variable region of the anti-IL-4Rα antibody in the form of scFv and the anti-IL-5Rα antibody in the form of IgG were constructed. In addition, cysteine mutations to form disulfide bonds were introduced at residue 44 of VH and residue 100 of VL, and comparison between heavy-chain (VH)-light-chain (VL) and light-chain (VL)-heavy-chain (VH) variable regions depending on the linking order of the VH and VL variable regions was performed.

As shown in the schematic diagram of FIG. 11, the format in which the variable region of anti-IL-4Rα was linked in the order of VH-VL to the C-terminus of the anti-IL-5Rα antibody was named "5R-IgG-4R-$_{HL}$scFv" (FIG. 11A), and the format in which the variable region of anti-IL-4Rα was linked in the order of VH-VL to the C-terminus of the anti-IL-5Rα antibody was named "5R-IgG-4R-$_{LH}$scFv" (FIG. 11C). The scFv was connected to the C-terminus of the anti-IL-5Rα antibody via an LGGGGSGGGGSGGGGS (16 amino acid residues) linker, and a GGGGSGGGGSGGGGSGGGGS (20 amino acid residues) linker was connected between VH-VL or VL-VH. The IL-4Rα×IL-5Rα bispecific antibodies were introduced into the pcDNA3.4 vector encoding the heavy-chains (CH1, CH2, CH3) and light-chain (CL) of IgG1. FIG. 11B is a schematic diagram of a vector encoding the light- and heavy-chains of 5R-IgG-4R-$_{HL}$scFv, and FIG. 11D is a schematic diagram of a vector encoding the light- and heavy-chains of 5R-IgG-4R-$_{LH}$scFv. In the variable region of anti-IL-4Rα, glycine residue 44 of VH was mutated to cysteine and glycine residue 100 of VL was mutated to cysteine.

Tables 15 and 16 respectively show the amino acid sequences of 5R-IgG-4R-$_{HL}$scFv and 5R-IgG-4R-$_{LH}$scFv. The anti-IL-5Rα antibody light-chain variable region of SEQ ID NO: 36 includes SEQ ID NOS: 37 to 48. The anti-IL-4Rα antibody heavy-chain variable region of SEQ ID NO: 61 includes a cysteine mutation introduced at residue 100 in SEQ ID NOS: 10 to 14. The anti-IL-4Rα antibody heavy-chain variable region of SEQ ID NO: 62 includes a cysteine mutation introduced at residue 46 in SEQ ID NOS: 22 to 24.

TABLE 15

| | |
|---|---|
| **4R-IgG-4R$_{HL}$scFv Light-chain** | |
| anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFT LTISSLQPDDFATYYCQQFGRYPYTFGSGTKVEVK |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| **SR-IgG-4R$_{HL}$scFv Heavy-chain** | |
| anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTV DKSTNTAYMELSSLRSEDTAVYYCTRDYYGRSYYYAMDYWGQGTTLTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |
| Linker (16 amino acid) (SEQ ID No: 57) | LGGGGSGGGGSGGGGS |
| anti-IL-4Rα VH (G100C) (SEQ ID No: 81) | EVQLLESGGGLVQPGGSLRLSCAASGFTFSRHAMAWVRQAPGKCLEWVSAITSSGRSIYYADSVKGRFTISR DNSKNTLYLQMNSLRAEDTAVYYCARVHRAFDYWGQGTLVTVSS |
| Linker (20 amino acid) (SEQ ID No: 59) | GGGGSGGGGSGGGGSGGGGS |
| anti-IL-4Rα VL (G44C) (SEQ ID No: 62) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGCGTKLTVLG |

TABLE 16

| | |
|---|---|
| **5R-IgG-4R$_{LH}$scFv Light-chain** | |
| anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFT LTISSLQPDDFATYYCQQFGRYPYTFGSGTKVEVK |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |

TABLE 16-continued

| SR-IgG-4R$_{LH}$scFv Heavy-chain | |
|---|---|
| anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTV DKSTNTAYMELSSLRSEDTAVYYCTRDYYGRSYYYAMDYWGQGTTLTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |
| Linker (16 amino acid) (SEQ ID No: 57) | LGGGGGGGGGSGGGGS |
| anti-IL-4Rα VL (G44C) (SEQ ID No: 62) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGCGTKLTVLG |
| Linker (20 amino acid) (SEQ ID No: 59) | GGGGSGGGGGGGGGSGGGGS |
| anti-IL-4Rα VH (G100C) (SEQ ID No: 61) | EVQLLESGGGLVQPGGSLRLSCAASGFTFSRHAMAWVRQAPGKCLEWVSAITSSGRSIYYADSVKGRFTISR DNSKNTLYLQMNSLRAEDTAVYYCARVHRAFDYWGQGTLVTVSS |

Example 20: Expression and Purification of IL-4Rα×IL-5Rα Bispecific Antibodies of 5R-IgG-4R-BscFv and 5R-IgG-4R-$_{LH}$scFv Formats that Simultaneously Bind to IL-4Rα and IL-5Rα

To express and purify the IL-4Rα×IL-5Rα bispecific antibody, HEK293F (Invitrogen) cells were transiently transfected. For transfection of 200 mL in a shake flask (Corning), HEK293F cells were seeded at a density of $2.0\times10^6$ cells/ml in 190 mL of a medium and incubated at 120 rpm, 8% $CO_2$ and 37° C. A total of 250 μg of light- and heavy-chains at a ratio of 1:1 in HEK293F cells was diluted in 5 ml serum-free Freestyle 293 expression medium (Invitrogen), filtered, mixed with 5 ml of a medium diluted with 750 μg of polyethylenimine (PEI) and then reacted for 10 minutes at room temperature. Then, the reacted mixed medium was injected into the 190 ml previously seeded cells, followed by incubation at 120 rpm and 8% $CO_2$ and further incubation for 6 days. Proteins were purified from the cell incubation supernatant collected with reference to standard protocols. The antibody was applied to a protein A Sepharose column and washed with PBS (pH 7.4). After the antibody was eluted at pH 3.0 using 0.1 M glycine and 0.5 M NaCl buffer, the sample was immediately neutralized using 1 M Tris buffer. The eluted protein was concentrated using a Vivaspin 30,000 MWCO (Sartorius) centrifugal concentrator after buffer exchange with storage buffer (PBS, pH 7.4). The purified protein was measured for absorbance at a wavelength of 562 nm using a solution in the BCA protein assay kit (Thermo), and the amount thereof was quantified according to the standard curve. As a result, 163 ug of 5R-IgG-4R-$_{HL}$scFv and 1.22 mg of 5R-IgG-4R-$_{LH}$-scFv were purified.

Example 21: SDS-PAGE and SEC Analysis of IL-4Rα×IL-5Rα Bispecific Antibodies of 5R-IgG-4R-$_{HL}$scFv and 5R-IgG-4R-$_{LH}$scFv Formats that Simultaneously Bind to IL-4Rα and IL-5Rα

3 μg of the 5R-IgG-4R-$_{HL}$scFv bispecific antibody purified in Example 20 was analyzed on SDS-PAGE under 12% non-reducing conditions (FIG. 12A). 5R-IgG-4R-$_{HL}$scFv has two light-chains of about 25 kDa and two units of heavy-chain-linker-scFv of about 77 kDa, and thus has a total molar mass of 204 kDa. The portion indicated by the arrow in FIG. 12 is 5R-IgG-4R-$_{HL}$scFV, and a band expected to correspond to an aggregate was rarely observed. In addition, 5R-IgG-4R-$_{HL}$scFV was analyzed by size-exclusion chromatography (SEC). Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer and the elution of the protein at a wavelength of 280 nm was determined. Elution times of β-amylase (200 kDa, sigma; A8781) and Herceptin (150 kDa) were compared to compare the molar mass of the proteins. 5R-IgG-4R-$_{HL}$scFV was observed at about 150 kDa and a peak expected to correspond to the aggregate was also observed (FIG. 12B).

Likewise, 3 μg of the 5R-IgG-4R-$_{LH}$scFV bispecific antibody purified in Example 20 was analyzed through SDS-PAGE under 12% non-reducing conditions (FIG. 12C). 5R-IgG-4R-$_{LH}$scFV has two light-chains of about 25 kDa and two units of heavy-chain-linker-scFv of about 77 kDa, and thus has a total molar mass of 204 kDa. The portion indicated by the arrow in FIG. 10C is 5R-IgG-4R-$_{LH}$scFV and a band expected to correspond to an aggregate was slightly observed in the upper portion. 5R-IgG-4R-$_{LH}$scFV was also analyzed by size exclusion chromatography. Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer. The elution of the protein at a wavelength of 280 nm was determined (FIG. 12D). Elution times of β-Amylase (200 kDa, sigma; A8781) and Herceptin (150 kDa) were compared to compare the molar masses of the proteins. 5R-IgG-4R-$_{LH}$scFV was observed around 200 kDa, and a peak expected to correspond to an aggregate was slightly observed. The result showed that the 5R-IgG-4R-$_{LH}$scFv had high expression and better physical properties (FIG. 12D).

Example 22: Comparison of Difference in Physical Properties Depending on Format Sequence of 5R-IgG-4R-$_{LH}$scFv Bispecific Antibody The IL-4Rα×IL-5Rα bispecific antibody sequence of the 5R-IgG-4R-$_{LH}$scFv format constructed in Example 21 was changed and additional expression levels and physical properties were compared. Specifically, the anti-IL-5Rα antibody is the heavy-chain variable region sequence of 5R65.7 (SEQ ID NO: 37), and the light-chain variable region (SEQ ID NO: 62) in the scFv constructed using the anti-IL-4Rα variable region was constructed by mutating glycine of residue 44 to cysteine in SEQ ID NOS: 22, 23, 24, 25, and 26, and the heavy-chain variable region (SEQ ID NO: 61) was constructed by mutating glycine of residue 100 in SEQ ID NOS: 10, 12, and 13 to cysteine. As a result, the constructed IL-4Rα×IL-5Rα bispecific antibodies can be grouped into 5R-IgG-4R-$_{LH}$scFv in common, but were named "5R65-IgG-4R34.1.19-$_{LH}$scFv", "5R65.7-IgG-4R.N3-$_{LH}$scFv", "5R65.7 IgG-4R.N4-$_{LH}$scFv", "5R65.7-IgG-4R.N6G-$_{LH}$scFv", "5R65.7-IgG-4R.N7-$_{LH}$scFv", and "5R65.7-IgG-4R.N8-$_{LH}$scFv" depending on each antibody sequence. The constructed antibodies were expressed and purified in the same manner as in Example 20 above. As a result, 5R65-IgG-4R34.1.19-$_{LH}$scFv (2.6 mg), 5R65.7-IgG-4R.N-$_{LH}$scFv (4.07 mg), 5R65.-IgG-4R.N4-$_{LH}$scFv (3.67 mg), 5R65.7-IgG-4R.N6-$_{LH}$scFv (4.98 mg), 5R65.7-IgG-4R.N7-$_{LH}$ scFv (3.91 mg), and 5R65.7-IgG-4R.N8-$_{LH}$scFv (4.48 mg) were purified.

The purified IL-4Rα×IL-5Rα bispecific antibodies were compared in physical properties through SDS-PAGE (FIG. 13) and SEC (FIG. 14) analysis. The result showed that 5R65.7-IgG-4R.N3-$_{LH}$scFv and 5R65.7-IgG-4R.N8-$_{LH}$scFv bispecific antibodies had almost no aggregates, which means that they exhibited improved physical properties and high expression levels.

Example 23: Construction of IL-4Rα×IL-5Rα Bispecific Antibodies of 4R-LL-5R and 4R-SL-5R Formats that Simultaneously Bind to IL-4Rα and IL-5Rα

Following the IgG-scFv format, an IL-4Rα×IL-5Rα bispecific antibody having bivalent binding to IL-4Rα and IL-5Rα antigens was further constructed in DVD-IgG (dual variable domain-IgG) format. IgG-scFv is different from DVD-IgG in that IgG-scFv has IL-4Rα and IL-5Rα antigen-binding sites constructed in opposite directions, whereas DVD-IgG has antigen-binding sites constructed in one direction. In DVD-IgG, the first variable region and the second variable region are juxtaposed via a linker. Since the second variable region disposed inside is covered by the first variable region, it may have reduced antigen-binding ability. Therefore, linker combinations were compared. A long linker ASTKGPSVFPLAP (13 amino acids) and a short linker ASTKGP (6 amino acids) were used as linkers between VH1 and VH2, and a long linker TVAAPSVFIFPP (12 amino acids) and a short linker TVAAP (5 amino acids) were used as linkers between VL1 and VL2.

As can be seen from the schematic diagram of FIG. 15, the anti-IL-4Rα antibody variable region is located in the first variable region, and the anti-IL-5Rα variable region is located in the second variable region. The format in which long linkers were connected to each other was named "4R-LL-5R" (FIG. 15A) and the format in which short linkers were connected to each other was named "4R-SL-5R" (FIG. 15C). The IL-4Rα×IL-5Rα bispecific antibodies were introduced into the pcDNA3.4 vector encoding the heavy-chains (CH1, CH2, CH3) and light-chain (CL) of IgG1. FIG. 15B is a schematic diagram of a vector encoding the light and heavy-chains of 4R-LL-5R, and FIG. 15D is a schematic diagram of a vector encoding the light and heavy-chains of 4R-SL-5R.

Tables 17 and 18 show the amino acid sequences of 4R-LL-5R and 4R-SL-5R, respectively. The anti-IL-4Rα antibody light-chain variable region of SEQ ID NO: 21 includes SEQ ID NOS: 22 to 26. The anti-IL-4Rα antibody heavy-chain variable region of SEQ ID NO: 7 includes SEQ ID NOS: 10 to 14. The anti-IL-5Rα antibody heavy-chain variable region of SEQ ID NO: 36 includes SEQ ID NOS: 37 to 42.

TABLE 17

| | |
|---|---|
| **4R-LL-5R Light-chain** | |
| anti-IL-4Rα VL (SEQ ID No: 21) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGGGTKLTVLG |
| VL Long linker (SEQ ID No: 63) | TVAAPSVFIFPP |
| anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFT LTISSLQPDDFATYYCQQFGRYPYTFGSGTKVEVK |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| **4R-LL-5R Heavy-chain** | |
| anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISR DNSKNTLYLQMNSLRAEDTAVYYCARVHRAFDYWGQGTLVTVSS |
| VH Long linker (SEQ ID No: 64) | ASTKGPSVFPLAP |
| anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTV DKSTNTAYMELSSLRSEDTAVYYCTRDYYGRSYYYAMDYWGQGTTLTVSS |

TABLE 17-continued

| | |
|---|---|
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |

TABLE 18

| | |
|---|---|
| | 4R-SL-5R Light-chain |
| anti-IL-4Rα VL (SEQ ID No: 21) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGGGTKLTVLG |
| VL short linker (SEQ ID No: 69) | TVAAP |
| anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFT LTISSLQPDDFATYYCQQFGRYPYTFGSGTKVEVK |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| | 4R-SL-5R Heavy-chain |
| anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISR DNSKNTLYLQMNSLRAEDTAVYYCARVHRAFDYWGQGTLVTVSS |
| VH short linker (SEQ ID No: 70) | ASTKGP |
| anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTV DKSTNTAYMELSSLRSEDTAVYYCTRDYYGRSYYYAMDYWGQGTTLTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |

Example 24: Expression and Purification of IL-4Rα×IL-5Rα Bispecific Antibodies of 4R-LL-5R and 4R-SL-5R Formats that Simultaneously Bind to IL-4Rα and IL-5Rα

To express and purify the IL-4Rα×IL-5Rα bispecific antibody, HEK293F (Invitrogen) cells were transiently transfected. For transfection of 200 mL of the cells in a shake flask (Corning), HEK293F cells were seeded at a density of $2.0\times10^6$ cells/ml in 190 mL of a medium and incubated at 120 rpm, 8% $CO_2$ and 37° C. A total of 250 μg of light- and heavy-chains at a ratio of 1:1 in HEK293F cells was diluted in 5 ml serum-free Freestyle 293 expression medium (Invitrogen), filtered, mixed with 5 ml of a medium diluted with 750 μg of polyethylenimine (PEI) and then reacted for 10 minutes at room temperature. Then, the reacted mixed medium was injected into the 190 ml previously seeded cells, followed by incubation at 120 rpm and 8% $CO_2$ and further incubation for 6 days. Proteins were purified from the cell incubation supernatant collected with reference to standard protocols. The antibody was applied to a protein A Sepharose column and washed with PBS (pH 7.4). After the antibody was eluted at pH 3.0 using 0.1 M glycine and 0.5 M NaCl buffer, the sample was immediately neutralized using 1 M Tris buffer. The eluted protein was concentrated using a Vivaspin 30,000 MWCO (Sartorius) centrifugal concentrator after buffer exchange with storage buffer (PBS, pH 7.4). The purified protein was measured for absorbance at a wavelength of 562 nm using a solution in the BCA protein assay kit (Thermo), and the amount thereof was quantified according to the standard curve. As a result, 71 μg of 4R-LL-5R and 240 μg of 4R-SL-5R were purified.

Example 25: SDS-PAGE and SEC Analysis of IL-4Rα×IL-5Rα Bispecific Antibodies of 4R-LL-5R and 4R-SL-5R Formats that Simultaneously Bind to IL-4Rα and IL-5Rα

The 4R-LL-5R bispecific antibody purified in Example 24 has two light-chains of about 36 kDa and two units of heavy-chains of about 64 kDa, and thus has a total molar mass of 200 kDa. 4R-LL-5R was analyzed by size-exclusion chromatography (SEC). Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer and the elution of the protein at a wavelength of 280 nm was determined. Elution times of β-amylase (200 kDa, sigma; A8781) and Herceptin (150 kDa) were compared to compare the molar mass of the proteins. 4R-LL-5R was observed at about 200 kDa and a peak expected to correspond to a monomer having no bispecific antibody was also observed (FIG. 16A).

Likewise, 3 μg of the 4R-LL-5R bispecific antibody purified in Example 24 was analyzed through SDS-PAGE under 12% non-reducing conditions (FIG. 16B). The 4R-LL-5R bispecific antibody has two light-chains of about 35 kDa and two units of heavy-chain-linker-scFv of about 63 kDa, and thus has a total molar mass of 196 kDa. The portion indicated by the arrow in FIG. 16B is 4R-SL-5R and a band expected to correspond to an aggregate was slightly observed in the upper portion. 4R-SL-5R was also analyzed by size exclusion chromatography. Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer. The elution of the protein at a wavelength of 280 nm was determined. Elution times of β-Amylase (200 kDa, Sigma; A8781) and Herceptin (150 kDa) were compared to compare the molar mass of the proteins. 4R-LL-5R was observed around 200 kDa, and a peak expected to correspond to an aggregate was slightly observed (FIG. 16C). The result showed that the 4R-LL-5R had low expression and better physical properties than long linkers.

Example 26: Construction of IL-4Rα×IL-5Rα Bispecific Antibodies of 5R-LL-4R and 5R-SL-4R Formats that Simultaneously Bind to IL-4Rα and IL-5Rα

Whether or not the physical properties of DVD-IgG were changed depending on the position of the anti-IL-4Rα antibody and the anti-IL-5Rα antibody, like the IgG-scFv format, was determined. Linker combinations were also compared. A long linker ASTKGPSVFPLAP (13 amino acids) and a short linker ASTKGP (6 amino acids) were used as linkers between VH1 and VH2, and a long linker TVAAPSVFIFPP (12 amino acids) and a short linker (5 amino acids) were used as linkers between VL1 and VL2.

As can be seen from the schematic diagram of FIG. 17, the anti-IL-5Rα antibody variable region is located in the first variable region and the anti-IL-4Rα variable region is located in the second variable region. The format in which long linkers were connected to each other was named "5R-LL-4R" (FIG. 17A), and the format in which short linkers were connected to each other was named "5R-SL-4R" (FIG. 17C). The IL-4Rα×IL-5Rα bispecific antibodies were introduced into the pcDNA3.4 vector encoding the heavy-chain (CH1, CH2, CH3) and light-chain (CL) of IgG1. FIG. 15B is a schematic diagram of a vector encoding the light- and heavy-chains of 5R-LL-4R, and FIG. 17D is a schematic diagram of a vector encoding the light- and heavy-chains of 5R-SL-4R.

Tables 19 and 20 show the amino acid sequences of 5R-LL-4R and 5R-SL-4R, respectively. The anti-IL-4Rα antibody light-chain variable region of SEQ ID NO: 21 includes SEQ ID NOS: 22 to 26. The anti-IL-4Rα antibody heavy-chain variable region of SEQ ID NO: 9 includes SEQ ID NOS: 10 to 14. The anti-IL-5Rα antibody heavy-chain variable region of SEQ ID NO: 36 includes SEQ ID NOS: 37 to 42.

TABLE 19

| | |
|---|---|
| | 5R-LL-4R Light-chain |
| anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFT LTISSLQPDDFATYYCQQFGRYPYTFGSGTKVEVK |
| VL Long linker (SEQ ID No: 63) | TVAAPSVFIFPP |
| anti-IL-4Rα VL (SEQ ID No: 21) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGGGTKLTVLG |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| | 5R-LL-4R Heavy-chain |
| anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTV DKSTNTAYMELSSLRSEDTAVYYCTRDYYGRSYYYAMDYWGQGTTLTVSS |
| VH Long linker (SEQ ID No: 64) | ASTKGPSVFPLAP |
| anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISR DNSKNTLYLQMNSLRAEDTAVYYCARVHRAFDYWGQGTLVTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |

TABLE 19-continued

| | |
|---|---|
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |

TABLE 20

| 5R-SL-4R Light-chain | |
|---|---|
| anti-IL-5Rα VL (SEQ ID No: 46) | DIQMTQSPSTLSASVGDRVTITCKASQNVGTAVAWYQQKPGKAPKLLIYWASTRHTGVPDRFSGSGSGTDFT LTISSLQPDDFATYYCQQFGRYPYTFGSGTKVEVK |
| VL short linker (SEQ ID No: 69) | TVAAP |
| anti-IL-4Rα VL (SEQ ID No: 21) | QSVLTQPPSASGTPGQRVTISCSGSPLFPDSGSFNWYQQLPGTAPKLLIYADSHRPSGVPDRFSGSKSGTSA SLAISGLRSEDEADYYCGTWDYSLSGYVLGGGTKLTVLG |
| CL (SEQ ID No: 47) | RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 5R-SL-4R Heavy-chain | |
| anti-IL-5Rα VH (SEQ ID No: 36) | QVQLVQSGAEVKKPGSSVKVSCKASGYTFTSYWINWVRQAPGQGLEWIGHIYPNKNENYYNHKFKDKATLTV DKSTNTAYMELSSLRSEDTAVYYCTRDYYGRSYYYAMDYWGQGTTLTVSS |
| VH short linker (SEQ ID No: 70) | ASTKGP |
| anti-IL-4Rα VH (SEQ ID No: 9) | EVQLLESGGGLVQPGGSLRLSCAASGFTFSRHAMAWVRQAPGKGLEWVSAITSSGRSIYYADSVKGRFTISR DNSKNTLYLQMNSLRAEDTAVYYCARVHRAFDYWGQGTLVTVSS |
| CH1 (SEQ ID No: 49) | ASTKGPSVFPLAPSSKSTSGGTAALGCLVKDYFPEPVTVSWNSGALTSGVHTFPAVLQSSGLYSLSSVVTVPS SSLGTQTYICNVNHKPSNTKVDKKV |
| Hinge (SEQ ID No: 50) | EPKSCDKTHTCPPCP |
| CH2 (SEQ ID No: 51) | APELLGGPSVFLFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAK |
| CH3 (SEQ ID No: 56) | GQPREPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |

Example 27: Expression and Purification of IL-4Rα×IL-5Rα Bispecific Antibodies of 5R-LL-4R and 5R-SL-4R Formats that Simultaneously Bind to IL-4Rα and IL-5Rα

To express and purify the IL-4Rα×IL-5Rα bispecific antibody, HEK293F (Invitrogen) cells were transiently transfected. For transfection of 200 mL of the cells in a shake flask (Corning), HEK293F cells were seeded at a density of $2.0\times10^6$ cells/ml in 190 mL of a medium and incubated at 120 rpm, 8% $CO_2$ and 37° C. A total of 250 μg of light- and heavy-chains at a ratio of 1:1 in HEK293F cells was diluted in 5 ml serum-free Freestyle 293 expression medium (Invitrogen), filtered, mixed with 5 ml of a medium diluted with 750 μg of polyethylenimine (PEI) and then reacted for 10 minutes at room temperature. Then, the reacted mixed medium was injected into the 190 ml previously seeded cells, followed by incubation at 120 rpm and 8% $CO_2$ and further incubation for 6 days. Proteins were purified from the cell incubation supernatant collected with reference to standard protocols. The antibody was applied to a protein A Sepharose column and washed with PBS (pH 7.4). After the antibody was eluted at pH 3.0 using 0.1 M glycine and 0.5 M NaCl buffer, the sample was immediately neutralized using 1 M Tris buffer. The eluted protein was concentrated using a Vivaspin 30,000 MWCO (Sartorius) centrifugal concentrator after buffer exchange with storage buffer (PBS, pH 7.4). The purified protein was measured for absorbance at a wavelength of 562 nm using a solution in the BCA protein assay kit (Thermo), and the amount thereof was quantified according to the standard curve. As a result, 22 μg of 5R-LL-4R and 12.6 μg of 5R-SL-4R were purified.

Example 28: SEC Analysis of IL-4Rα×IL-5Rα Bispecific Antibodies of 5R-LL-4R and 5R-SL-4R Formats that Simultaneously Bind to IL-4Rα and IL-5Rα

The 5R-LL-4R bispecific antibody purified in Example 27 has two light-chains of about 36 kDa and two units of heavy-chains of about 64 kDa, and thus has a total molar mass of 200 kDa. 5R-LL-4R was analyzed by size-exclusion chromatography (SEC). Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer and the elution of the protein at a wavelength of 280 nm was determined. Elution times of β-amylase (200 kDa, Sigma;

A8781) and Herceptin (150 kDa) were compared to compare the molar masses of the proteins. For 5R-LL-4R, a low peak was observed around 200 kDa, which indicates that the bispecific antibody was not formed well (FIG. 18A).

Likewise, 3 μg of the 5R-SL-4R bispecific antibody purified in Example 27 was analyzed by size exclusion chromatography. Specifically, 10 μg of protein was injected into a Superdex 200 Increase 10/300 GL column using PBS (12 mM phosphate, 0.5 M NaCl, 2.7 mM KCl, pH 7.4) with high salt concentration as a running buffer. The elution of the protein at a wavelength of 280 nm was determined (FIG. 12D). Elution times of β-Amylase (200 kDa, sigma; A8781) and Herceptin (150 kDa) were compared to compare the molar mass of the proteins. 5R-LL-4R was observed around 200 kDa, and a peak expected to correspond to an aggregate was observed, followed by peaks with lower heights (FIG. 18B). As a result, both 5R-LL-4R and 5R-SL-4R, in which the variable region of the anti-IL-5Rα antibody was disposed in the first variable region, had poor physical properties.

Example 29: Comparison of Difference in Physical Properties Depending on Format Sequence of 4R-LL-5R Bispecific Antibody The antibody sequences of the 4R-LL-5R format constructed in Example above were changed and additional expression levels and physical properties were compared. Specifically, the anti-IL-5Rα antibody was constructed to have the heavy-chain variable region sequence of 5R65.7 (SEQ ID NO: 37), and the anti-IL-4Rα antibody was constructed to have the light-chain variable regions of the sequences of SEQ ID NOS: 22, 23, 24, 25, and 26, and heavy-chain variable regions of the sequences of SEQ ID NOS: 10, 12, and 13. The constructed IL-4Rα×IL-5Rα bispecific antibodies can be grouped into a 4R-LL-5R format, but was named "4R34.1.19-SL-5R65", "4R.N3-SL-5R65.7", "4R.N4-SL-5R65.7", "4R.N6-SL-5R65.7", "4R.N7-SL-5R65.7", and "4R.N8-SL-5R65.7" depending on the antibody sequence. The constructed antibodies were expressed and purified in the same manner as in Example 24 above. As a result, 4R34.1.19-SL-5R65 (0.21 mg), 4R.N3-SL-5R65.7 (3.26 mg), 4R.N4-SL-5R65.7 (0.52 mg), 4R.N6-SL-5R65.7 (1.8 mg), 4R.N7-SL-5R65.7 (0.7 mg), and 4R.N8-SL-5R65.7 (1.52 mg) were purified.

The purified IL-4Rα×IL-5Rα bispecific antibodies were compared in physical properties through SDS-PAGE (FIG. 19) and SEC (FIG. 20) analysis. The result showed that 4R.N3-SL-5R65.7, 4R.N6-SL-5R65.7, and 4R.N8-SL-5R65.7 bispecific antibodies had improved physical properties and high expression levels.

Example 30: Confirmation of Antigen Binding Ability Depending on Format of IL-4Rα×IL-5Rα Bispecific Antibody The antigen-binding capacity was compared by indirect ELISA depending on the format of BsIgG (monovalent binding capacity, IgG form), IgG-scFv (bivalent antigen-binding sites located in opposite directions), and DVD-IgG (bivalent antigen-binding sites in juxtaposition) constructed in the previous examples. IL-4Rα×IL-5Rα bispecific antibodies were constructed based on 4R34.1.19 and 5R65 antibodies.

Specifically, sIL-4Rα antigen protein (50 ng/well, Sinobio; 10402-H08H) and sIL-5Rα antigen protein (50 ng/well, Sinobio; 10392-H08H) were immobilized on a 96-well plate at room temperature for 1 hour, and blocked using 2% skim milk containing 0.1% PBST (0.1% Tween20, pH 7.4, 137 mM NaCl, 10 mM phosphate, 2.7 mM KCl) at room temperature for 2 hours. After discarding the solution and then washing the same three times with 0.1% PBST, the antibody was diluted to 100 nM, 10 nM and 1 nM, added to the blocked plate in an amount of 25 μl/well, and allowed to react at room temperature for 1 hour. After discarding the solution and washing the same three times with 0.1% PBST, an anti-human Fc-HRP antibody (1:8000) as a secondary antibody was added in an amount of 25 μl/well and reacted at room temperature for 1 hour. After discarding the solution and washing three times with PBST, a TMB solution was added in an amount of 25 μl/well, color development was induced at room temperature for 2 minutes, the reaction was stopped using $H_2SO_4$ (2N), and the absorbance at 450 nm was measured.

BsIgG has monovalent binding ability to sIL-4Rα and sIL-5Rα antigens. It can be confirmed that the monoclonal antibody of 4R34.1.19 has a decreased binding ability to sIL-4Rα compared to the binding ability to sIL-4Rα. The binding ability of BsIgG to sIL-5Rα was reduced less compared to 5R65, which is considered to be due to the cross-binding ability of the 4R34.1.19 antibody to sIL-5Rα (FIG. 21). The 5R65-IgG-4R34.1.19-$_{LH}$scFv format has a reduced binding ability to sIL-4Rα and had no reduction in the binding ability to sIL-5Rα since the antigen-binding site for sIL-4Rα is constructed with scFv (FIG. 21). In the 4R34.1.19-SL-5R65 format, 5R65 located in the second variable region is highly likely to have low binding ability to sIL-5Rα. As expected, it was confirmed that the high binding capacity for sIL-4Rα was maintained and the binding capacity for sIL-5Rα was decreased (FIG. 21).

Example 31: Confirmation of IL-4Rα and IL-5Rα Expression in Human Eosinophils from Healthy Controls (Donors)

Prior to evaluating the bioactivity of IL-4Rα×IL-5Rα bispecific antibodies using eosinophils, the expression of IL-4Rα and IL-5Rα in eosinophils in the granulocyte layer was observed in peripheral blood from healthy controls. Specifically, 20 ml of Ficoll-Paque solution (GE Healthcare, 17-5442-03) was dispensed into each 50 ml polypropylene centrifuge tube, and 20 ml of the heparinized patient blood was layered on each tube. The result was centrifuged at 879×g at room temperature for 25 minutes to separate and collect the lowest layer. 2% dextran solution was dispensed to separate the red blood cells (lower layer) and the granulocyte layer (upper layer) from each other, and the granulocyte layer was recovered and 27 ml of sterilized water and 3 ml of 10×HBSS were added thereto to remove red blood cells mixed therewith. Concentrated granulocytes (eosinophils and neutrophils) from which red blood cells were removed were separated and collected by centrifugation at 300×g and 4° C. for 10 minutes.

The enriched granulocytes can be classified into eosinophils and neutrophils depending on the expression of siglec 8 (sialic acid-binding immunoglobulin-like lectin). Eosinophils express siglec-8 and do not express neutrophils. Specifically, granulosa cells concentrated at a density of $1\times10^6$/donor sample, 5 μl of APC anti-human Siglec-8 Ab (Biolegen; 347105), and 5 μl of PE anti-human IL-4Rα Ab (Biolegend; 355004) or 0.5 μl of PE anti-human IL-5Rα Ab (BD Pharmingen; 555902) were mixed, reacted at 4° C. for 30 minutes, washed with PBSM (Miltenyli biotec; 130-091-

221), and then analyzed using a FACS Calibur (BD Bioscience) flow cytometer. After analysis, a dot graph of each sample was obtained.

Table 22 shows the gating strategy in which eosinophils were classified depending on the presence or absence of siglec-8 expression in enriched granulocytes derived from healthy donors and the result of confirming the expression of IL-4Rα and IL-5Rα. Eosinophils express a relatively low proportion of IL-4Rα and a higher proportion of IL-5Rα. However, it was confirmed that both IL-4Rα and IL-5Rα were expressed.

Example 32: Evaluation of Ability of IL-4Rα×IL-5Rα Bispecific Antibodies to Inhibit Proliferation of Human Eosinophils Derived from Healthy Controls IL-5 is well known to contribute to the proliferation of eosinophils, but the proliferation of eosinophils by IL-4 has little known. The present inventors identified the proliferative ability of eosinophils by IL-4 and IL-5, and determined whether or not the proliferative ability of eosinophils increased more when treated with both IL-4 and IL-5 than when treated with either IL-4 or IL-5. In addition, the present inventors also determined whether or not the IL-4Rα×IL-5Rα bispecific antibody inhibited the proliferation of eosinophils by the two cytokines.

Specifically, 20 ml of Ficoll-Paque solution (GE Healthcare, 17-5442-03) was dispensed into each 50 ml polypropylene centrifuge tube, and 20 ml of the heparinized patient blood was layered on each tube. The result was centrifuged at 879×g at room temperature for 25 minutes to separate and collect the lowest layer. 2% dextran solution was dispensed to separate the red blood cells (lower layer) and the granulocyte layer (upper layer) from each other, the granulocyte layer was recovered and 27 ml of sterilized water and 3 ml of 10×HBSS were added thereto to remove red blood cells mixed therewith. Concentrated granulocytes (eosinophils and neutrophils) from which red blood cells were removed were separated and collected by centrifugation at 300×g and 4° C. for 10 minutes. Finally, only eosinophils were purified from granulocytes using a commercially available eosinophil Cell Isolation Kit (Miltenyi Biotec; 130-092-010) according to the manufacturer's protocol.

Eosinophils were seeded at $5\times10^4$ cells/well into a 96-well cell culture plate, and human IL-5 having a final concentration of 100 pM and human IL-4 having a final concentration of 100 pM were added thereto to induce proliferation of eosinophils. In addition, anti-IL-4Rα antibody (4R34.1.19), anti-IL-5Rα antibody (5R65), and bispecific antibodies (BsIgG, 4R34.1.19-SL-5R65) having a final concentration of 500 nM were added thereto. Each antibody was cultured in 2 to 3 wells and the final capacity of each well was adjusted to 200 μl. After culturing for 2 days at 37° C. in a $CO_2$ incubator, 100 μl of cell suspension was recovered from each well, and 100 μl of Cellliter-Glo® Promega sample was added to the culture medium and incubated at room temperature for 20 minutes. The proliferative ability of eosinophils was analyzed by measuring luminescence with a microplate meter.

The result of the analysis showed that IL-4 can also induce the proliferation of eosinophils and treatment with both IL-4 and IL-5 provides a higher proliferation ability of eosinophils than treatment with either IL-4 or IL-5. Since 4R34.1.19 has a binding ability to IL-5Rα, it exhibited similar eosinophil proliferation inhibitory activity to IL-4Rα×IL-5Rα bispecific antibodies. Among the IL-4Rα×IL-5Rα bispecific antibodies, 4R34.1.19-SL-5R65 exhibited a higher ability to inhibit eosinophil proliferation than BsIgG. This is considered because 4R34.1.19-SL-5R65 has a bivalent antigen-binding site and has a higher binding ability to each antigen (FIG. 23).

Example 33: Evaluation of Ability of IL-4Rα×IL-5Rα Bispecific Antibodies to Induce Antibody-Dependent Cytotoxicity of Human Eosinophils Derived from Healthy Donors An increase in the number of eosinophils is closely related to allergic diseases. In order to reduce the number of eosinophils, it is also important to inhibit the proliferation of eosinophils, but it is more effective to induce more directly antibody-dependent cellular cytotoxicity (ADCC) using effector cells such as NK cells. Benralizumab was approved as an antibody against IL-5Rα by the FDA and is known to inhibit the activity of IL-5 and eliminate eosinophils caused by ADCC. In addition, benralizumab has an afucosylated Fc and thus has higher ADCC activity due to the higher affinity for Fcγ expressed in NK cells than IgG1 Fc (Kolbeck et al., 2010). The present inventors prepared benralizumab analogues having the same variable region (Accession Number: DB12023) and IgG1 Fc as benralizumab and determined whether or not the bispecific antibody that binds to both IL-4Rα and IL-5Rα has higher ability to induce ADCC than the monoclonal antibody that targets IL-5Rα by comparing the activity between anti-IL-5Rα antibody (5R65) and IL-4Rα×IL-5Rα bispecific antibodies having the same IgG1 Fc (BsIgG, 4R34.1.19-SL-5R65).

Specifically, 20 ml of Ficoll-Paque solution (GE Healthcare, 17-5442-03) was seeded into each 50 ml polypropylene centrifuge tube, and 20 ml of the heparinized patient blood was layered on each tube. The result was centrifuged at 879×g at room temperature for 25 minutes to separate and collect a buffy coat layer. The buffy coat layer was treated with IL-2 and incubated for 10 days to expand peripheral blood mononuclear cells (PBMCs). After 10 days, NK cells were purified using a NK cell isolation kit (Miltenyi Biotec; 130-092-657) according to the manufacturer's protocol.

Again, the peripheral blood of the same healthy donor was layered with Ficoll-Paque and then the lowest layer was separated and collected to isolate eosinophils. The eosinophils were purified using the eosinophil cell isolation kit (Miltenyi Biotec; 130-092-010) according to the manufacturer's protocol. The purified NK cells and eosinophils were used as effectors and target cells at a ratio of 10:1. First, eosinophils as target cells were incubated with CellTrace™ CFSE (Invitrogen) having a final concentration of 10 μM at 37° C. in the absence of light for 30 minutes. After addition of a cell culture medium, the result was incubated at room temperature for 5 minutes, the supernatant was removed by centrifugation at 300×g for 10 minutes at room temperature, and then the eosinophils were released into the cell culture medium. Eosinophils and NK cells are seeded at densities of $2\times10^4$ cells/well and $2\times10^5$ cells/well, respectively, into a 96-well U-shaped cell culture plate, and human IL-5 at a final concentration of 100 pM was added thereto. In addition, an anti-IL-5Rα antibody (benralizumab analogue, 5R65) and IL-4Rα×IL-5Rα bispecific antibody (BsIgG, 4R34.1.19-SL-5R65), each having a final concentration of 250 nM were added thereto. Each antibody was cultured in two wells and the final volume of each well was adjusted to 200 μl. The antibody was incubated for 6 hours at 37° C. in a $CO_2$ incubator. After the culture, the cell suspension was recovered from each well and the fluorescence of the calcein-AM released was detected by a fluorescence plate meter. Antibody-dependent cytotoxicity inducing ability was calculated using the following equation.

$$\text{Cytotoxicity }(\%)=(A-B)/(C-B)\times 100$$

A: Release value upon antibody treatment

B: Spontaneous cell release value

C: Maximum cell release value (Triton X-100 treatment group)

The result of the analysis showed that the bispecific antibody (IL-4Rα×IL-5Rα) that targets both IL-4Rα and IL-5Rα (BsIgG, 4R34.1.19-SL-5R65) exhibited higher cytotoxicity inducing ability for eosinophils derived from healthy donors, compared to a monoclonal antibody targeting IL-5Rα (benralizumab analogue, 5R65). In particular, 4R34.1.19-SL-5R65 exhibited the strongest induction ability. This can be confirmed by a quantified graph (FIG. 24).

INDUSTRIAL APPLICABILITY

Currently, clinical results of monoclonal antibodies for allergic/inflammatory diseases are limited in that they have effects only in some patients or have little effect. The reason for this limitation is that the phenotype is different for each patient. In particular, since allergic diseases occur in combination with several cytokines and immune cells, neutralizing two or more cytokines at the same time is a much more efficient strategy than neutralizing a single cytokine.

Therefore, a bispecific antibody that simultaneously neutralizes major cytokines that induce an inflammatory response can suppress inflammation more comprehensively and have a synergistic effect. In addition, the bispecific antibody simultaneously targets two receptors expressed on one cell and provides stronger and specific targeting, thereby eliminating inflammatory immune cells based on increased cell growth inhibition and/or ADCC. Based thereon, IL-4Rα×IL-5Rα bispecific antibodies that simultaneously bind to and target IL-4Rα and IL-4Rα can be used for treatment of allergic diseases, inflammatory diseases, and/or diseases caused by an increase in eosinophils, but are not limited thereto.

Examples of such diseases include, but are not limited to, hypereosinophilic syndrome (HES), hypereosinophilia, asthma including eosinophilic asthma, eosinophilic bronchial asthma (ABA) and severe eosinophilic bronchial asthma (ABA), chronic obstructive pulmonary disease (COPD), Churg-Strauss syndrome, eosinophilic esophagitis, eosinophilic gastroenteritis, eosinophilic gastrointestinal disease (EGID), atopic diseases such as atopic dermatitis, allergic diseases such as allergic rhinitis, immunoglobulin (IgE)-mediated food allergy, inflammatory bowel disease, allergic colitis, gastroesophageal reflux, endocardial myocardial fibrosis, Loeffler endocarditis, Davis disease, intermittent angioedema associated with eosinophilia, eosinophilia-myalgia syndrome/Spanish toxic oil syndrome, liver cirrhosis, dermatitis impetigo, bullous pemphigoid, Churg-Strauss syndrome, acute myelogenous eosinophilic leukemia, acute lymphocytic eosinophilic leukemia, systemic mast cell disease with eosinophilia, eczema, Wegner's granulomatosis, polyarteritis nodosa, eosinophilic vasculitis, rheumatoid arthritis, and the like.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

SEQUENCE LISTING FREE TEXT

An electronic file is attached.

The invention claimed is:

1. A bispecific antibody or antigen-binding fragment thereof binding to both IL-4Rα and IL-5Rα comprising:

an antibody or an antigen-binding fragment thereof binding to interleukin (IL)-4 receptor α (IL-4Rα, CD124) comprising:

a heavy-chain CDR1 of SEQ ID NO: 1, a heavy-chain CDR2 of SEQ ID NO: 5, a heavy-chain CDR3 of SEQ ID NO: 8, a light-chain CDR1 of SEQ ID NO: 13, a light-chain CDR2 of SEQ ID NO: 14, and a light-chain CDR3 of SEQ ID NO: 16;

a heavy-chain CDR1 of SEQ ID NO: 1, a heavy-chain CDR2 of SEQ ID NO: 6, a heavy-chain CDR3 of SEQ ID NO: 8, a light-chain CDR1 of SEQ ID NO: 13, a light-chain CDR2 of SEQ ID NO: 14, and a light-chain CDR3 of SEQ ID NO: 17;

a heavy-chain CDR1 of SEQ ID NO: 1, a heavy-chain CDR2 of SEQ ID NO: 5, a heavy-chain CDR3 of SEQ ID NO: 8, a light-chain CDR1 of SEQ ID NO: 13, a light-chain CDR2 of SEQ ID NO: 14, and a light-chain CDR3 of SEQ ID NO: 18;

a heavy-chain CDR1 of SEQ ID NO: 1, a heavy-chain CDR2 of SEQ ID NO: 3, a heavy-chain CDR3 of SEQ ID NO: 8, a light-chain CDR1 of SEQ ID NO: 13, a light-chain CDR2 of SEQ ID NO: 14, and a light-chain CDR3 of SEQ ID NO: 19; or a heavy-chain CDR1 of SEQ ID NO: 1, a heavy-chain CDR2 of SEQ ID NO: 5, a heavy-chain CDR3 of SEQ ID NO: 8, a light-chain CDR1 of SEQ ID NO: 13, a light-chain CDR2 of SEQ ID NO: 14, and a light-chain CDR3 of SEQ ID NO: 20; and an antibody or an antigen-binding fragment thereof binding to interleukin (IL)-5 receptor α(IL-5Rα, CD125) comprising:

a heavy-chain CDR1 of SEQ ID NO: 27, a heavy-chain CDR2 selected of SEQ ID NO: 28, a heavy-chain CDR3 of SEQ ID NO: 30, a light-chain CDR1 of SEQ ID NO: 43, a light-chain CDR2 of SEQ ID NO: 44, and a light-chain CDR3 of SEQ ID NO: 45;

a heavy-chain CDR1 of SEQ ID NO: 27, a heavy-chain CDR2 of SEQ ID NO: 28, a heavy-chain CDR3 of SEQ ID NO: 31, a light-chain CDR1 of SEQ ID NO: 43, a light-chain CDR2 of SEQ ID NO: 44, and a light-chain CDR3 of SEQ ID NO: 45;

a heavy-chain CDR1 of SEQ ID NO: 27, a heavy-chain CDR2 of SEQ ID NO: 28, a heavy-chain CDR3 of SEQ ID NO: 32, a light-chain CDR1 of SEQ ID NO: 43, a light-chain CDR2 of SEQ ID NO: 44, and a light-chain CDR3 of SEQ ID NO: 45;

a heavy-chain CDR1 of SEQ ID NO: 27, a heavy-chain CDR2 of SEQ ID NO: 28, a heavy-chain CDR3 of SEQ ID NO: 33, a light-chain CDR1 of SEQ ID NO: 43, a light-chain CDR2 of SEQ ID NO: 44, and a light-chain CDR3 of SEQ ID NO: 45;

a heavy-chain CDR1 of SEQ ID NO: 27, a heavy-chain CDR2 of SEQ ID NO: 28, a heavy-chain CDR3 of SEQ ID NO: 34, a light-chain CDR1 of SEQ ID NO: 43, a light-chain CDR2 of SEQ ID NO: 44, and a light-chain CDR3 of SEQ ID NO: 45; or a heavy-chain CDR1 of SEQ ID NO: 27, a heavy-chain CDR2 of SEQ ID NO: 28, a heavy-chain CDR3 of SEQ ID NO: 30, a light-chain CDR1 of SEQ ID NO: 43, a light-chain CDR2 of SEQ ID NO: 44, and a light-chain CDR3 of SEQ ID NO: 35.

2. The antibody or antigen-binding fragment thereof according to claim 1, wherein the antibody or antigen-binding fragment thereof binding to IL-4Rα comprises:

a heavy-chain variable region of SEQ ID NO: 12 and a light-chain variable region of SEQ ID NO: 22;

a heavy-chain variable region of SEQ ID NO: 67 and a light-chain variable region of SEQ ID NO: 23;

a heavy-chain variable region of SEQ ID NO: 12 and a light-chain variable region of SEQ ID NO: 24;

a heavy-chain variable region of SEQ ID NO: 10 and a light-chain variable region of SEQ ID NO: 25; or a heavy-chain variable region of SEQ ID NO: 12 and a light-chain variable region of SEQ ID NO: 26.

3. The antibody or antigen-binding fragment thereof according to claim 1, wherein the antibody or antigen-binding fragment thereof binding to IL-5Rα comprises:

a heavy-chain variable region of SEQ ID NO: 37 and a light-chain variable region of SEQ ID NO: 46; a heavy-chain variable region of SEQ ID NO: 38 and a light-chain variable region of SEQ ID NO: 46;

a heavy-chain variable region of SEQ ID NO: 39 and a light-chain variable region of SEQ ID NO: 46;

a heavy-chain variable region of SEQ ID NO: 40 and a light-chain variable region of SEQ ID NO: 46;

a heavy-chain variable region of SEQ ID NO: 41 and a light-chain variable region of SEQ ID NO: 46; or a heavy-chain variable region of SEQ ID NO: 37 and a light-chain variable region of SEQ ID NO: 42.

4. The antibody or antigen-binding fragment thereof according to claim 1, wherein the bispecific antibody or antigen-binding fragment thereof comprises:

a bispecific antibody having an scIgG or BsIgG format in which a heavy-chain variable region and a light-chain variable region of the antibody binding to IL-4Rα or of the antibody binding to IL-5Rα are linked to a heterodimeric Fc;

a bispecific antibody having an IgG-scFv format in which scFv including the heavy-chain variable region and the light-chain variable region of the antibody binding to IL-4Rα or of the antibody binding to IL-5Rα is linked to a C-terminus of IgG including the heavy-chain variable region and the light-chain variable region of the antibody binding to IL-4Rα or of the antibody binding to IL-5Rα; or a bispecific antibody having a DVD (dual variable domain) IgG format including a format in which heavy-chain and light-chain variable regions of the antibody binding to IL-4Rα or of the antibody binding to IL-5Rα are juxtaposed (tandemly repeated) at an N-terminus of the IgG including the heavy-chain variable region and the light-chain variable region of the antibody binding to IL-4Rα or of the antibody binding to IL-5Rα.

5. A multispecific antibody or antigen-binding fragment thereof comprising the bispecific antibody binding to both IL-4Rα and IL-5Rα according to claim 1.

6. A nucleic acid encoding the bispecific antibody or antigen-binding fragment thereof binding to both IL-4Rα and IL-5Rα according to claim 1.

7. An expression vector comprising the nucleic acid according to claim 6.

8. A cell transformed with the expression vector according to claim 7.

9. A method of producing a bispecific antibody or antigen-binding fragment thereof binding to both IL-4Rα and IL-5Rα comprising:

(a) culturing the cell according to claim 8 to produce a bispecific antibody or antigen-binding fragment thereof binding to both IL-4Rα and IL-5Rα; and (b) recovering the bispecific antibody or antigen-binding fragment thereof.

10. A method for treating allergic diseases, inflammatory diseases, and/or diseases caused by an increase in eosinophils comprising administering to a subject the bispecific antibody or antigen-binding fragment thereof binding to both IL-4Rα and IL-5Rα according to claim 1.

11. The method according to claim 10, wherein the allergic diseases, inflammatory diseases, and/or diseases caused by an increase in eosinophils are selected from the group consisting of hypereosinophilic syndrome (HES), hypereosinophilia, asthma, eosinophilic asthma, eosinophilic bronchial asthma (ABA), severe ABA, chronic obstructive pulmonary disease (COPD), Churg-Strauss syndrome, eosinophilic esophagitis, eosinophilic gastroenteritis, eosinophilic gastrointestinal disease (EGID), an atopic disease, atopic dermatitis, an allergic disease, allergic rhinitis, food allergy, immunoglobulin (IgE)-mediated food allergy, inflammatory bowel disease, allergic colitis, gastroesophageal reflux, endocardial myocardial fibrosis, Loeffler endocarditis, Davis disease, intermittent angioedema associated with eosinophilia, eosinophilia-myalgia syndrome/Spanish toxic oil syndrome, liver cirrhosis, dermatitis impetigo, bullous pemphigoid, acute myelogenous eosinophilic leukemia, acute lymphocytic eosinophilic leukemia, systemic mast cell disease with eosinophilia, eczema, Wegner's granulomatosis, polyarteritis nodosa, eosinophilic vasculitis, rheumatoid arthritis, Kawasaki disease, sickle cell disease, Grave's disease, pre-eclampsia, Sjogren's syndrome, autoimmune lymphoproliferative syndrome, autoimmune hemolytic anemia, Barrett's esophagus, autoimmune uveitis, tuberculosis, nephritis, herpes, chronic idiopathic urticarial, scleroderma, hypertrophic scarring, Whipple's disease, benign prostatic hyperplasia, an inflammatory disorder, and inflammatory bowel disease.

* * * * *

```
                              SEQUENCE LISTING

<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: Synthetic CDR1 Sequence

<400> SEQUENCE: 1

Arg His Ala Met Ala
1               5


<210> SEQ ID NO 2
<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 2

Ala Ile Thr Ser Ser Gly Arg Ser Ile Tyr Tyr Ala Asp Ser Val Lys
1               5                   10                  15

Gly


<210> SEQ ID NO 3
```

<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 3

Ala Ile Thr Ala Ser Gly Arg Ser Ile Tyr Tyr Ala Asp Ser Val Lys
1 5 10 15

Gly

<210> SEQ ID NO 4
<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 4

Ala Ile Thr Ala Ser Gly Arg Gly Ile Tyr Tyr Gly Asp Ser Val Lys
1 5 10 15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 5

Ala Ile Thr Met Ser Gly Arg Ser Ile Tyr Tyr Ala Asp Ser Val Lys
1 5 10 15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 6

Ala Ile Thr Met Ser Gly Arg Gly Ile Tyr Tyr Ala Asp Ser Val Lys
1 5 10 15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 7

Ala Ile Thr Ala Ser Gly Met Ser Ile Tyr Tyr Ala Asp Phe Ala Lys
1 5 10 15

Gly

<210> SEQ ID NO 8
<211> LENGTH: 7
<212> TYPE: PRT
<213> ORGANISM: Artificial Sequence
<220> FEATURE:

<223> OTHER INFORMATION: Synthetic CDR3 Sequence

<400> SEQUENCE: 8

```
Val His Arg Ala Phe Asp Tyr
1               5
```

<210> SEQ ID NO 9
<211> LENGTH: 116
<212> TYPE: PRT
<213> ORGANISM: Artificial Sequence
<220> FEATURE:
<223> OTHER INFORMATION: Synthetic VH Sequence

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Ala Trp Val Arg Gln Ala Pro Gly Lys Gly Leu Glu Trp Val
        35                  40                  45

Ser Ala Ile Thr Ser Ser Gly Arg Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115
```

<210> SEQ ID NO 10
<211> LENGTH: 116
<212> TYPE: PRT
<213> ORGANISM: Artificial Sequence
<220> FEATURE:
<223> OTHER INFORMATION: Synthetic VH Sequence

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Ala Trp Val Arg Gln Ala Pro Gly Lys Gly Leu Glu Trp Val
        35                  40                  45

Ser Ala Ile Thr Ala Ser Gly Arg Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115
```

<210> SEQ ID NO 11
<211> LENGTH: 116
<212> TYPE: PRT

<213> ORGANISM: Artificial Sequence
<220> FEATURE:
<223> OTHER INFORMATION: Synthetic VH Sequence

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Ala Trp Val Arg Gln Ala Pro Gly Lys Gly Leu Glu Trp Val
        35                  40                  45

Ser Ala Ile Thr Ala Ser Gly Arg Ser Ile Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115
```

<210> SEQ ID NO 12
<211> LENGTH: 116
<212> TYPE: PRT
<213> ORGANISM: Artificial Sequence
<220> FEATURE:
<223> OTHER INFORMATION: Synthetic VH Sequence

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Ala Trp Val Arg Gln Ala Pro Gly Lys Gly Leu Glu Trp Val
        35                  40                  45

Ser Ala Ile Thr Met Ser Gly Arg Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115
```

<210> SEQ ID NO 13
<211> LENGTH: 13
<212> TYPE: PRT
<213> ORGANISM: Artificial Sequence
<220> FEATURE:
<223> OTHER INFORMATION: Synthetic CDR1 Sequence

<400> SEQUENCE: 13

```
Ser Gly Ser Pro Leu Phe Pro Asp Ser Gly Ser Phe Asn
1               5                   10
```

<210> SEQ ID NO 14

<211> LENGTH: 7
<212> TYPE: PRT
<213> ORGANISM: Artificial Sequence
<220> FEATURE:
<223> OTHER INFORMATION: Synthetic CDR2 Sequence

<400> SEQUENCE: 14

Ala Asp Ser His Arg Pro Ser
1 5

<210> SEQ ID NO 15
<211> LENGTH: 11
<212> TYPE: PRT
<213> ORGANISM: Artificial Sequence
<220> FEATURE:
<223> OTHER INFORMATION: Synthetic CDR3 Sequence

<400> SEQUENCE: 15

Gly Thr Trp Asp Tyr Ser Leu Ser Gly Tyr Val
1 5 10

<210> SEQ ID NO 16
<211> LENGTH: 11
<212> TYPE: PRT
<213> ORGANISM: Artificial Sequence
<220> FEATURE:
<223> OTHER INFORMATION: Synthetic CDR3 Sequence

<400> SEQUENCE: 16

Gly Thr Trp Asp Tyr Ser Leu Asn Arg Tyr Val
1 5 10

<210> SEQ ID NO 17
<211> LENGTH: 11
<212> TYPE: PRT
<213> ORGANISM: Artificial Sequence
<220> FEATURE:
<223> OTHER INFORMATION: Synthetic CDR3 Sequence

<400> SEQUENCE: 17

Gly Thr Trp Asp Tyr Ser Leu Ser Ala Tyr Val
1 5 10

<210> SEQ ID NO 18
<211> LENGTH: 11
<212> TYPE: PRT
<213> ORGANISM: Artificial Sequence
<220> FEATURE:
<223> OTHER INFORMATION: Synthetic CDR3 Sequence

<400> SEQUENCE: 18

Gly Thr Trp Asp Tyr Ser Leu Asn Ser Tyr Val
1 5 10

<210> SEQ ID NO 19
<211> LENGTH: 11
<212> TYPE: PRT
<213> ORGANISM: Artificial Sequence
<220> FEATURE:
<223> OTHER INFORMATION: Synthetic CDR3 Sequence

<400> SEQUENCE: 19

Gly Thr Trp Asp Tyr Ser Leu Ser Ser Tyr Val
1 5 10

<210> SEQ ID NO 20
<211> LENGTH: 11

<212> TYPE: PRT
<213> ORGANISM: Artificial Sequence
<220> FEATURE:
<223> OTHER INFORMATION: Synthetic CDR3 Sequence

<400> SEQUENCE: 20

```
Gly Ser Trp Asp Tyr Ser Leu Ser Arg Tyr Val
1               5                   10
```

<210> SEQ ID NO 21
<211> LENGTH: 111
<212> TYPE: PRT
<213> ORGANISM: Artificial Sequence
<220> FEATURE:
<223> OTHER INFORMATION: Synthetic VL Sequence

<400> SEQUENCE: 21

```
Gln Ser Val Leu Thr Gln Pro Pro Ser Ala Ser Gly Thr Pro Gly Gln
1               5                   10                  15

Arg Val Thr Ile Ser Cys Ser Gly Ser Pro Leu Phe Pro Asp Ser Gly
            20                  25                  30

Ser Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu Gly
            100                 105                 110
```

<210> SEQ ID NO 22
<211> LENGTH: 111
<212> TYPE: PRT
<213> ORGANISM: Artificial Sequence
<220> FEATURE:
<223> OTHER INFORMATION: Synthetic VL Sequence

<400> SEQUENCE: 22

```
Gln Ser Val Leu Thr Gln Pro Pro Ser Ala Ser Gly Thr Pro Gly Gln
1               5                   10                  15

Arg Val Thr Ile Ser Cys Ser Gly Ser Pro Leu Phe Pro Asp Ser Gly
            20                  25                  30

Ser Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Asn Arg Tyr Val Leu Gly Gly Gly Thr Lys Leu Thr Val Leu Gly
            100                 105                 110
```

<210> SEQ ID NO 23
<211> LENGTH: 111
<212> TYPE: PRT
<213> ORGANISM: Artificial Sequence
<220> FEATURE:
<223> OTHER INFORMATION: Synthetic VL Sequence

<400> SEQUENCE: 23

Gln Ser Val Leu Thr Gln Pro Pro Ser Ala Ser Gly Thr Pro Gly Gln
1 5 10 15

Arg Val Thr Ile Ser Cys Ser Gly Ser Pro Leu Phe Pro Asp Ser Gly
20 25 30

Ser Phe Asn Trp Tyr Gln Gln Leu Pro Gly Thr Ala Pro Lys Leu Leu
35 40 45

Ile Tyr Ala Asp Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Asp Tyr Ser Leu
85 90 95

Ser Ala Tyr Val Leu Gly Gly Gly Thr Lys Leu Thr Val Leu Gly
100 105 110

<210> SEQ ID NO 24
<211> LENGTH: 111
<212> TYPE: PRT
<213> ORGANISM: Artificial Sequence
<220> FEATURE:
<223> OTHER INFORMATION: Synthetic VL Sequence

<400> SEQUENCE: 24

Gln Ser Val Leu Thr Gln Pro Pro Ser Ala Ser Gly Thr Pro Gly Gln
1 5 10 15

Arg Val Thr Ile Ser Cys Ser Gly Ser Pro Leu Phe Pro Asp Ser Gly
20 25 30

Ser Phe Asn Trp Tyr Gln Gln Leu Pro Gly Thr Ala Pro Lys Leu Leu
35 40 45

Ile Tyr Ala Asp Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Asp Tyr Ser Leu
85 90 95

Asn Ser Tyr Val Leu Gly Gly Gly Thr Lys Leu Thr Val Leu Gly
100 105 110

<210> SEQ ID NO 25
<211> LENGTH: 111
<212> TYPE: PRT
<213> ORGANISM: Artificial Sequence
<220> FEATURE:
<223> OTHER INFORMATION: Synthetic VL Sequence

<400> SEQUENCE: 25

Gln Ser Val Leu Thr Gln Pro Pro Ser Ala Ser Gly Thr Pro Gly Gln
1 5 10 15

Arg Val Thr Ile Ser Cys Ser Gly Ser Pro Leu Phe Pro Asp Ser Gly
20 25 30

Ser Phe Asn Trp Tyr Gln Gln Leu Pro Gly Thr Ala Pro Lys Leu Leu
35 40 45

Ile Tyr Ala Asp Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Asp Tyr Ser Leu
85 90 95

Ser Ser Tyr Val Leu Gly Gly Gly Thr Lys Leu Thr Val Leu Gly
100 105 110

<210> SEQ ID NO 26
<211> LENGTH: 111
<212> TYPE: PRT
<213> ORGANISM: Artificial Sequence
<220> FEATURE:
<223> OTHER INFORMATION: Synthetic VL Sequence

<400> SEQUENCE: 26

Gln Ser Val Leu Thr Gln Pro Pro Ser Ala Ser Gly Thr Pro Gly Gln
1 5 10 15

Arg Val Thr Ile Ser Cys Ser Gly Ser Pro Leu Phe Pro Asp Ser Gly
20 25 30

Ser Phe Asn Trp Tyr Gln Gln Leu Pro Gly Thr Ala Pro Lys Leu Leu
35 40 45

Ile Tyr Ala Asp Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Asp Tyr Ser Leu
85 90 95

Ser Arg Tyr Val Leu Gly Gly Gly Thr Lys Leu Thr Val Leu Gly
100 105 110

<210> SEQ ID NO 27
<211> LENGTH: 5
<212> TYPE: PRT
<213> ORGANISM: Artificial Sequence
<220> FEATURE:
<223> OTHER INFORMATION: Synthetic CDR1 Sequence

<400> SEQUENCE: 27

Ser Tyr Trp Ile Asn
1 5

<210> SEQ ID NO 28
<211> LENGTH: 17
<212> TYPE: PRT
<213> ORGANISM: Artificial Sequence
<220> FEATURE:
<223> OTHER INFORMATION: Synthetic CDR2 Sequence

<400> SEQUENCE: 28

His Ile Tyr Pro Asn Lys Asn Glu Asn Tyr Tyr Asn His Lys Phe Lys
1 5 10 15

Asp

<210> SEQ ID NO 29
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 29

Asp Tyr Tyr Gly Arg Ser Tyr Tyr Tyr Ala Met Asp Tyr
1 5 10

```
<210> SEQ ID NO 30
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 30

Glu Phe Tyr Gly Arg Gln Tyr Tyr Gln Ala Met Asp Tyr
1               5                   10


<210> SEQ ID NO 31
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 31

Glu Tyr Tyr Gly Arg Ser Tyr Tyr Ala Ala Met Asp Tyr
1               5                   10


<210> SEQ ID NO 32
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 32

Glu His Tyr Gly Arg Pro Tyr Tyr Asn Ala Met Asp Tyr
1               5                   10


<210> SEQ ID NO 33
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 33

Glu Tyr Tyr Gly Arg Thr Tyr Tyr Ser Ala Met Asp Tyr
1               5                   10


<210> SEQ ID NO 34
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 34

Glu Phe Tyr Gly Arg Ser Arg Tyr Ser Ala Met Asp Tyr
1               5                   10


<210> SEQ ID NO 35
<211> LENGTH: 13
<212> TYPE: PRT
<213> ORGANISM: Artificial Sequence
<220> FEATURE:
<223> OTHER INFORMATION: Synthetic CDR3 Sequence

<400> SEQUENCE: 35

Glu Tyr Tyr Gly Arg Ser Tyr Tyr Asn Ala Met Asp Tyr
1               5                   10
```

<210> SEQ ID NO 36
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly His Ile Tyr Pro Asn Lys Asn Glu Asn Tyr Tyr Asn His Lys Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Tyr Gly Arg Ser Tyr Tyr Tyr Ala Met Asp Tyr Trp
            100                 105                 110

Gly Gln Gly Thr Thr Leu Thr Val Ser Ser
        115                 120
```

<210> SEQ ID NO 37
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly His Ile Tyr Pro Asn Lys Asn Glu Asn Tyr Tyr Asn His Lys Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Phe Tyr Gly Arg Gln Tyr Tyr Gln Ala Met Asp Tyr Trp
            100                 105                 110

Gly Gln Gly Thr Thr Leu Thr Val Ser Ser
        115                 120
```

<210> SEQ ID NO 38
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 38

```
Gln Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Ile
35 40 45

Gly His Ile Tyr Pro Asn Lys Asn Glu Asn Tyr Tyr Asn His Lys Phe
50 55 60

Lys Asp Lys Ala Thr Leu Thr Val Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Thr Arg Glu Tyr Tyr Gly Arg Ser Tyr Tyr Ala Ala Met Asp Tyr Trp
100 105 110

Gly Gln Gly Thr Thr Leu Thr Val Ser Ser
115 120

<210> SEQ ID NO 39
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 39

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Ile
35 40 45

Gly His Ile Tyr Pro Asn Lys Asn Glu Asn Tyr Tyr Asn His Lys Phe
50 55 60

Lys Asp Lys Ala Thr Leu Thr Val Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Thr Arg Glu His Tyr Gly Arg Pro Tyr Tyr Asn Ala Met Asp Tyr Trp
100 105 110

Gly Gln Gly Thr Thr Leu Thr Val Ser Ser
115 120

<210> SEQ ID NO 40
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 40

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Arg Gln Ala Pro Gly Gln Gly Leu Glu Trp Ile
35 40 45

Gly His Ile Tyr Pro Asn Lys Asn Glu Asn Tyr Tyr Asn His Lys Phe
50 55 60

Lys Asp Lys Ala Thr Leu Thr Val Asp Lys Ser Thr Asn Thr Ala Tyr

```
65                  70                  75                  80

Met Glu Leu Ser Ser Leu Arg Ser Glu Asp Thr Ala Val Tyr Tyr Cys
                85                  90                  95

Thr Arg Glu Tyr Tyr Gly Arg Thr Tyr Tyr Ser Ala Met Asp Tyr Trp
            100                 105                 110

Gly Gln Gly Thr Thr Leu Thr Val Ser Ser
        115                 120


<210> SEQ ID NO 41
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly His Ile Tyr Pro Asn Lys Asn Glu Asn Tyr Tyr Asn His Lys Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Phe Tyr Gly Arg Ser Arg Tyr Ser Ala Met Asp Tyr Trp
            100                 105                 110

Gly Gln Gly Thr Thr Leu Thr Val Ser Ser
        115                 120


<210> SEQ ID NO 42
<211> LENGTH: 122
<212> TYPE: PRT
<213> ORGANISM: Artificial Sequence
<220> FEATURE:
<223> OTHER INFORMATION: Synthetic VH Sequence

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly His Ile Tyr Pro Asn Lys Asn Glu Asn Tyr Tyr Asn His Lys Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Tyr Tyr Gly Arg Ser Tyr Tyr Asn Ala Met Asp Tyr Trp
            100                 105                 110

Gly Gln Gly Thr Thr Leu Thr Val Ser Ser
        115                 120
```

<210> SEQ ID NO 43
<211> LENGTH: 27
<212> TYPE: PRT
<213> ORGANISM: Artificial Sequence
<220> FEATURE:
<223> OTHER INFORMATION: Synthetic CDR1 Sequence

<400> SEQUENCE: 43

```
Lys Ala Ser Gln Asn Val Gly Thr Ala Val Ala Trp Ala Ser Thr Arg
1               5                   10                  15

His Thr Gln Gln Phe Gly Arg Tyr Pro Tyr Thr
            20                  25
```

<210> SEQ ID NO 44
<211> LENGTH: 7
<212> TYPE: PRT
<213> ORGANISM: Artificial Sequence
<220> FEATURE:
<223> OTHER INFORMATION: Synthetic CDR2 Sequence

<400> SEQUENCE: 44

```
Trp Ala Ser Thr Arg His Thr
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic CDR3 Sequence

<400> SEQUENCE: 45

```
Gln Gln Phe Gly Arg Tyr Pro Tyr Thr
1               5
```

<210> SEQ ID NO 46
<211> LENGTH: 107
<212> TYPE: PRT
<213> ORGANISM: Artificial Sequence
<220> FEATURE:
<223> OTHER INFORMATION: Synthetic VL Sequence

<400> SEQUENCE: 46

```
Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Phe Gly Arg Tyr Pro Tyr
                85                  90                  95

Thr Phe Gly Ser Gly Thr Lys Val Glu Val Lys
            100                 105
```

<210> SEQ ID NO 47
<211> LENGTH: 107
<212> TYPE: PRT
<213> ORGANISM: Artificial Sequence
<220> FEATURE:

<223> OTHER INFORMATION: Synthetic CL Sequence

<400> SEQUENCE: 47

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 48
<211> LENGTH: 59
<212> TYPE: PRT
<213> ORGANISM: Artificial Sequence
<220> FEATURE:
<223> OTHER INFORMATION: Synthetic Linker Sequence

<400> SEQUENCE: 48

Gly Ser Ser Gly Ser Gly Ser Gly Ser Thr Gly Thr Ser Ser Ser Gly
1 5 10 15

Thr Gly Thr Ser Ala Gly Thr Thr Gly Thr Ser Ala Ser Thr Ser Gly
20 25 30

Ser Gly Ser Gly Gly Gly Gly Gly Ser Gly Gly Gly Gly Ser Ala Gly
35 40 45

Gly Thr Ala Thr Ala Gly Ala Ser Ser Gly Ser
50 55

<210> SEQ ID NO 49
<211> LENGTH: 98
<212> TYPE: PRT
<213> ORGANISM: Artificial Sequence
<220> FEATURE:
<223> OTHER INFORMATION: CH1

<400> SEQUENCE: 49

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 50

<211> LENGTH: 15
<212> TYPE: PRT
<213> ORGANISM: Artificial Sequence
<220> FEATURE:
<223> OTHER INFORMATION: Hinge

<400> SEQUENCE: 50

```
Glu Pro Lys Ser Cys Asp Lys Thr His Thr Cys Pro Pro Cys Pro
1               5                   10                  15
```

<210> SEQ ID NO 51
<211> LENGTH: 110
<212> TYPE: PRT
<213> ORGANISM: Artificial Sequence
<220> FEATURE:
<223> OTHER INFORMATION: CH2

<400> SEQUENCE: 51

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 52
<211> LENGTH: 107
<212> TYPE: PRT
<213> ORGANISM: Artificial Sequence
<220> FEATURE:
<223> OTHER INFORMATION: CH3A

<400> SEQUENCE: 52

```
Gly Gln Pro Arg Glu Pro Gln Val Tyr Thr Leu Pro Pro Ser Arg Asp
1               5                   10                  15

Glu Leu Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 53
<211> LENGTH: 107
<212> TYPE: PRT
<213> ORGANISM: Artificial Sequence
<220> FEATURE:

<223> OTHER INFORMATION: CH3B

<400> SEQUENCE: 53

Gly Gln Pro Arg Glu Pro Arg Val Tyr Thr Leu Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Val Ser Asp Gly Ser Phe
50 55 60

Thr Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly Lys
100 105

<210> SEQ ID NO 54
<211> LENGTH: 107
<212> TYPE: PRT
<213> ORGANISM: Artificial Sequence
<220> FEATURE:
<223> OTHER INFORMATION: CL_V133E

<400> SEQUENCE: 54

Arg Thr Val Ala Ala Pro Ser Val Phe Ile Phe Pro Pro Ser Asp Glu
1 5 10 15

Gln Leu Lys Ser Gly Thr Ala Ser Val Glu Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 55
<211> LENGTH: 107
<212> TYPE: PRT
<213> ORGANISM: Artificial Sequence
<220> FEATURE:
<223> OTHER INFORMATION: CL_V133K

<400> SEQUENCE: 55

Arg Thr Val Ala Ala Pro Ser Val Phe Ile Phe Pro Pro Ser Asp Glu
1 5 10 15

Gln Leu Lys Ser Gly Thr Ala Ser Val Lys Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu

```
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 56
<211> LENGTH: 107
<212> TYPE: PRT
<213> ORGANISM: Artificial Sequence
<220> FEATURE:
<223> OTHER INFORMATION: CH3

<400> SEQUENCE: 56

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 57
<211> LENGTH: 16
<212> TYPE: PRT
<213> ORGANISM: Artificial Sequence
<220> FEATURE:
<223> OTHER INFORMATION: Linker

<400> SEQUENCE: 57

Leu Gly Gly Gly Gly Ser Gly Gly Gly Gly Ser Gly Gly Gly Gly Ser
1               5                   10                  15


<210> SEQ ID NO 58
<211> LENGTH: 122
<212> TYPE: PRT
<213> ORGANISM: Artificial Sequence
<220> FEATURE:
<223> OTHER INFORMATION: anti-IL-5Ralpha VH G44C

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Cys Leu Glu Trp Ile
        35                  40                  45

Gly His Ile Tyr Pro Asn Lys Asn Glu Asn Tyr Tyr Asn His Lys Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Asp Tyr Tyr Gly Arg Ser Tyr Tyr Tyr Ala Met Asp Tyr Trp
            100                 105                 110

Gly Gln Gly Thr Thr Leu Thr Val Ser Ser
        115                 120


<210> SEQ ID NO 59
<211> LENGTH: 20
<212> TYPE: PRT
<213> ORGANISM: Artificial Sequence
<220> FEATURE:
<223> OTHER INFORMATION: Linker

<400> SEQUENCE: 59

Gly Gly Gly Gly Ser Gly Gly Gly Gly Ser Gly Gly Gly Gly Ser Gly
1               5                   10                  15

Gly Gly Gly Ser
            20


<210> SEQ ID NO 60
<211> LENGTH: 107
<212> TYPE: PRT
<213> ORGANISM: Artificial Sequence
<220> FEATURE:
<223> OTHER INFORMATION: anti-IL-5Ralpha VL S100C

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Cys Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Phe Gly Arg Tyr Pro Tyr
                85                  90                  95

Thr Phe Gly Ser Gly Thr Lys Val Glu Val Lys
            100                 105


<210> SEQ ID NO 61
<211> LENGTH: 116
<212> TYPE: PRT
<213> ORGANISM: Artificial Sequence
<220> FEATURE:
<223> OTHER INFORMATION: anti-IL-4Ralpha VH G100C

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Ala Trp Val Arg Gln Ala Pro Gly Lys Cys Leu Glu Trp Val
        35                  40                  45

Ser Ala Ile Thr Ser Ser Gly Arg Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115


<210> SEQ ID NO 62
<211> LENGTH: 111
<212> TYPE: PRT
<213> ORGANISM: Artificial Sequence
<220> FEATURE:
<223> OTHER INFORMATION: anti-IL-4Ralpha VL G44C

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Pro Leu Phe Pro Asp Ser Gly
            20                  25                  30

Ser Phe Asn Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Cys Gly Thr Lys Leu Thr Val Leu Gly
            100                 105                 110


<210> SEQ ID NO 63
<211> LENGTH: 12
<212> TYPE: PRT
<213> ORGANISM: Artificial Sequence
<220> FEATURE:
<223> OTHER INFORMATION: VL Long linker

<400> SEQUENCE: 63

Thr Val Ala Ala Pro Ser Val Phe Ile Phe Pro Pro
1               5                   10


<210> SEQ ID NO 64
<211> LENGTH: 13
<212> TYPE: PRT
<213> ORGANISM: Artificial Sequence
<220> FEATURE:
<223> OTHER INFORMATION: VH Long linker

<400> SEQUENCE: 64

Ala Ser Thr Lys Gly Pro Ser Val Phe Pro Leu Ala Pro
1               5                   10


<210> SEQ ID NO 65
<211> LENGTH: 207
<212> TYPE: PRT
<213> ORGANISM: Artificial Sequence
<220> FEATURE:
<223> OTHER INFORMATION: IL-4Ralpha

<400> SEQUENCE: 65

Met Lys Val Leu Gln Glu Pro Thr Cys Val Ser Asp Tyr Met Ser Ile
1               5                   10                  15
```

```
Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205


<210> SEQ ID NO 66
<211> LENGTH: 322
<212> TYPE: PRT
<213> ORGANISM: Artificial Sequence
<220> FEATURE:
<223> OTHER INFORMATION: IL-5Ralpha

<400> SEQUENCE: 66

Asp Leu Leu Pro Asp Glu Lys Ile Ser Leu Leu Pro Pro Val Asn Phe
1               5                   10                  15

Thr Ile Lys Val Thr Gly Leu Ala Gln Val Leu Leu Gln Trp Lys Pro
            20                  25                  30

Asn Pro Asp Gln Glu Gln Arg Asn Val Asn Leu Glu Tyr Gln Val Lys
        35                  40                  45

Ile Asn Ala Pro Lys Glu Asp Asp Tyr Glu Thr Arg Ile Thr Glu Ser
    50                  55                  60

Lys Cys Val Thr Ile Leu His Lys Gly Phe Ser Ala Ser Val Arg Thr
65                  70                  75                  80

Ile Leu Gln Asn Asp His Ser Leu Leu Ala Ser Ser Trp Ala Ser Ala
                85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
        115                 120                 125

Tyr Gln Val Ser Leu His Cys Thr Trp Leu Val Gly Thr Asp Ala Pro
    130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175
```

```
Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
        195                 200                 205

Gln Leu Phe Ala Leu His Ala Ile Asp Gln Ile Asn Pro Pro Leu Asn
    210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
    290                 295                 300

Trp Ser Gln Pro Ile Tyr Val Gly Asn Asp Glu His Lys Pro Leu Arg
305                 310                 315                 320

Glu Trp


<210> SEQ ID NO 67
<211> LENGTH: 116
<212> TYPE: PRT
<213> ORGANISM: Artificial Sequence
<220> FEATURE:
<223> OTHER INFORMATION: Synthetic VH Sequence

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Ala Trp Val Arg Gln Ala Pro Gly Lys Gly Leu Glu Trp Val
        35                  40                  45

Ser Ala Ile Thr Met Ser Gly Arg Gly Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115


<210> SEQ ID NO 68
<211> LENGTH: 116
<212> TYPE: PRT
<213> ORGANISM: Artificial Sequence
<220> FEATURE:
<223> OTHER INFORMATION: Synthetic VH Sequence

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30
```

-continued

```
Ala Met Ala Trp Val Arg Gln Ala Pro Gly Lys Gly Leu Glu Trp Val
        35                  40                  45

Ser Ala Ile Thr Ala Ser Gly Met Ser Ile Tyr Tyr Ala Asp Phe Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Arg Ala Phe Asp Tyr Trp Gly Gln Gly Thr Leu Val
            100                 105                 110

Thr Val Ser Ser
        115


<210> SEQ ID NO 69
<211> LENGTH: 5
<212> TYPE: PRT
<213> ORGANISM: Artificial Sequence
<220> FEATURE:
<223> OTHER INFORMATION: Linker

<400> SEQUENCE: 69

Thr Val Ala Ala Pro
1               5


<210> SEQ ID NO 70
<211> LENGTH: 6
<212> TYPE: PRT
<213> ORGANISM: Artificial Sequence
<220> FEATURE:
<223> OTHER INFORMATION: Linker

<400> SEQUENCE: 70

Ala Ser Thr Lys Gly Pro
1               5
```